(12) United States Patent
Chojkier et al.

(10) Patent No.: US 7,402,567 B2
(45) Date of Patent: Jul. 22, 2008

(54) TREATMENT OF DISEASE BY INDUCING CELL APOPTOSIS

(75) Inventors: Mario Chojkier, San Diego, CA (US); Martina Buck, San Diego, CA (US)

(73) Assignees: The Regents of the University of California, Oakland, CA (US); The United States of America as represented by the Department of Veterans Affairs, Office of the General Counsel (024), Washington, DC (US)

(*) Notice: Subject to any disclaimer, the term of this patent is extended or adjusted under 35 U.S.C. 154(b) by 441 days.

(21) Appl. No.: 10/415,325

(22) PCT Filed: Oct. 26, 2001

(86) PCT No.: PCT/US01/51123
§ 371 (c)(1),
(2), (4) Date: Sep. 8, 2003

(87) PCT Pub. No.: WO02/46218
PCT Pub. Date: Jun. 13, 2002

(65) Prior Publication Data
US 2004/0141976 A1      Jul. 22, 2004

Related U.S. Application Data

(60) Provisional application No. 60/244,018, filed on Oct. 27, 2000.

(51) Int. Cl.
*A61K 38/00* (2006.01)
*A61K 38/43* (2006.01)
*C07K 14/00* (2006.01)

(52) U.S. Cl. .............................. 514/18; 514/2; 530/300; 530/350; 424/94.1

(58) Field of Classification Search ................... 514/18, 514/2; 530/300, 350; 424/94.1
See application file for complete search history.

(56) References Cited

U.S. PATENT DOCUMENTS 5,215,892 A    6/1993  Kishimoto et al.

FOREIGN PATENT DOCUMENTS

JP            5192152      3/1993

WO        WO 95/03326        2/1995

OTHER PUBLICATIONS

Hutt et al., Signal Transducer and Activator of Transcription 3 Activates CCAAT Enhancer-binding Protein Gene Transcription in Go Growth-arrested Mouse Mammary Epithelial Cells and in Involuting Mouse Mammary Gland, 2000, vol. 275, pp. 29123-29131.*
Akira et al. (1990) "A nuclear factor for IL-6 expression (NF-IL6) is a member of a C/EBP family," EMBO J. 9:1897-1906.
Alley et al. (1988) "Feasibility of Drug Screening with Panels of Human Tumor Cell Lines Using a Microculture Tetrazolium Assay," Cancer Res. 48:589-601.
Andrade et al. (1998) "Granzyme B Directly and Efficiently Cleaves Several Downstream Caspase Substrates: Implications for CTL-Induced Apoptosis," Immunity 8:451-460.
Ankoma-Sey and Friedman, "Hepatic stellate cells," in *Liver Growth and Repair*, Strain and Diehl (eds.), Chapman & Hall, London, pp. 512-537, 1998.
Ashkenazi et al. (1998) "Death Receptors: Signaling and Modulation," Science 281:1305-1308.
Beg et al. (1996) "An Essential Role for NF-B in Preventing TNF-Induced Cell Death," Science 274:782-784.
Bhatt et al. (1999) "The Protein Kinase p90 Rsk as an Essential Mediator of Cytostatic Factor Activity," Science 286:1362-1365.
Blanchard et al. (2000) "Caspase-8 Specificity Probed at Subsite $S_4$: Crystal Structure of the caspase-8-Z-DEVD-cho Complex," J. Mol. Biol. 302:9-16.
Bonni et al. (1999) "Cell Survival Promoted by the Ras-MAPK Signaling Pathway by Transcription-Dependent and -Independent Mechanisms," Science 286:1358-1362.
Boshart et al. (1985) "A Very Strong Enhancer is Located Upstream of an Immediate Early Gene of Human Cytomegalovirus," Cell 41:521-530.
Boyle et al. (1991) "Phosphopeptide Mapping and Phosphoamino Acid Analysis by Two-Dimensional Separation of Thin-Layer Cellulose Plates," Meth. Enzymol. 201:110-149.

(Continued)

*Primary Examiner*—Jon P Weber
*Assistant Examiner*—Rita Mitra
(74) *Attorney, Agent, or Firm*—Medlen & Carroll, LLP

(57) ABSTRACT

The present invention relates generally to the treatment and prevention of diseases characterized by excess cell proliferation and/or activation. In particular, the present invention provides compositions and methods to suppress the activation and/or proliferation of various cells. In preferred embodiments, the present invention provides compositions and methods to suppress the activation and/or proliferation of mesenchymally derived cells (including, but not limited to hepatic stellate cells), as well as cells with abnormal growth characteristics. In particularly preferred embodiments, the present invention provides compositions and methods to induce fibrosis.

9 Claims, 18 Drawing Sheets

OTHER PUBLICATIONS

Bravo et al. (1987) "Cyclin/PCNA is the auxiliary protein of DNA polymerase-δ," Nature 326:515-517.

Buck et al. (1999) "Phosphorylation of Rat Serine 105 or Mouse Threonine 217 in C/EBPβ Is Required for Hepatocyte Proliferation Induced by TGFα," Mol. Cell. 4:1087-1092.

Buck et al. (1994) "LAP (NF-IL-6), a tissue-specific transcriptional activator, is an inhibitor of hepatoma cell proliferation," EMBO J. 13:851-860.

Buck and Chojkier (1996) "Muscle wasting and dedifferentiation induced by oxidative stress in a murine model of cachexia is prevented by inhibitors of nitric oxide synthesis and antioxidants," EMBO J. 15:1753-1765.

Cao (1991) "Regulated expression of three C/EBP isoforms during adipose conversion of 3T3-L1 cells," Genes Dev. 5:1538-1552.

Caruthers et al. (1980) "New chemical methods for synthesizing polynucleotides," Nuc. Acids Res. Symp. Ser. 215-223.

Chen et al. (1995) "Signal-induced site-specific phosphorylation targets IκBα to the ubiquitin-proteasome pathway," Genes Dev. 9:1586-1597.

Chen et al. (1995) "Separate domains of p21 involved in the inhibition of Cdk kinase and PCNA," Nature 374:386-388.

Chinery et al. (1997) "Antioxidants enhance the cytotoxicity of chemotherapeutic agents in colorectal cancer: A p53-independent induction of $p21^{WAF1/CIP1}$ via C/EBPβ," Nat. Med. 3:1233-1241.

Chojkier, "Pathogenesis of Hepatic Fibrosis," in *Pathogenesis of Hepatic Fibrosis In Extracellular Matrix*, Marcel Dekker Inc., NY, NY, pp. 541-557, 1993.

Chojkier, "Regulation of collagen gene expression," in *Liver Growth and Repair*, Strain and Diehl (eds.), Chapman & Hall, London, pp. 430-450, 1998.

Descombes et al. (1990) "LAP, a novel member of the C/EBP gene family, encodes a liver-enriched transcriptional activator protein," Genes Dev. 4:1541-1551.

Dijkema et al. (1985) "Cloning and Expression of the Chromosomal Immune Interferon Gene of the Rat," EMBO J. 4:761-767.

Earnshaw et al. (1999) "Mammalian Caspases: Structure, Activation, Substrates, and Functions During Apoptosis," Ann. Rev. Biochem. 68:383-424.

Friedman et al. (1989) Maintenance of Differentiated Phenotype of Cultured Rat Hepatic Lipocytes by Basement Membrane Matrix, J. Biol. Chem. 264:10756-10762.

Friedman et al. (1985) "Hepatic lipocytes: The principal collagen-producing cells of normal rat liver," Proc. Natl. Acad. Sci. USA 82:8681-8685.

Garcia-Calvo et al. (1998) "Inhibition of Human Caspases by Peptide-based and Macromolecular Inhibitors," J. Biol. Chem. 273:32608-32613.

Gorman et al., "The Rous Sarcoma Virus Long Terminal Repeat is a Strong Promoter when Introduced into a Variety of Eukaryotic Cells by DNA-Mediated Transfection," Proc. Natl. Acad. Sci. USA 79:6777-6781 (1982).

Graves et al. (2000) "Regulation of carbamoyl phosphate synthetase by MAP kinase," Nature 403:328-332.

Green et al. (1998) "Mitochondria and Apoptosis," Science 281:1309-1312.

Gross et al. (1999) "Induction of Metaphase Arrest in Cleaving *Xenopus* Embryos by the Protein Kinase $p90^{Rsk}$," Science 286:1365-1367.

Harris et al. (1998) "Definition and Redesign of the Extended Substrate Specificity of Granzyme B," J. Biol. Chem. 273:27364-27373.

Horn et al. (1980) "Synthesis of oligonucleotides on cellulose. Part II: design and synthetic strategy to the synthesis of 22 oligodeoxynucleotides coding for Gastric Inhibitory Polypeptide (GIP)[1]," Nuc. Acids Res. Symp. Ser. 225-232.

Houglum et al. (1995) "Two Different *cis*-acting Regulatory Regions Direct Cell-specific Transcription of the Collagen $\alpha_1$(I) Gene in Hepatic Stellate Cells and in Skin and Tendon Fibroblasts," J. Clin. Invest. 96:2269-2276.

Houglum et al. (1995) "LAP (NF-IL6) Transactivates the Collage $\alpha_1$(I) Gene from a 5' Regulatory Region," J. Clin Invest. 94:808-814.

Joza et al. (2001) "Essential role of the mitochrondrial apoptosis-inducing factor in programmed cell death," Nature 410:549-554.

Kim et al. (1990) "Use of the Human Elogation Factor 1α Promoter as a Versatile and Efficient Expression System," Gene 91:217-223.

Lavoie et al. (1996) "Cyclin D1 Expression is Regulated Positively by the p42/44*MAPK* and Negatively by the p38/HOG*MAPK* Pathway," J. Biol. Chem. 271:20608-20616.

Lee et al. (1995) "Activation of Hepatic Stellate Cells by TGFα Collagen Type I is Mediated by Oxidative Stress Through c-*myb* Expression," J. Clin. Invest. 96:2461-2468.

Lee et al. (1997) "Activation of the IκBα Kinase Complex by MEKK1, a Kinase of the JNK Pathway," Cell 88:213-222.

Maher et al. (1990) "Extracellular Matrix Gene Expression Increases Preferentially in Rat Lipocytes and Sinusoidal Endothelial Cells during Hepatic Fibrosis In Vivo," J. Clin. Invest. 86:1641-48.

Maniatis et al. (1987) "Regulation of Inducible and Tissue-Specific Gene Expression," Science 236:1237-1245.

Mao et al. (1998) "Activation of Caspase-1 in the Nucleus Requires Nuclear Translocation of Pro-caspase-1 Mediated by its Prodomain," J. Biol. Chem. 273:23621-23624.

Margolin et al. (1997) "Substrate and Inhibitor Specificity of Interleukin-1β-converting Enzyme and Related Caspases," J. Biol. Chem. 272:7223-7228.

Merrifield (1963) "Solid Phase Peptide Synthesis. I. The Synthesis of a Tetrapeptide," J. Am. Chem. Soc. 85:2149-2154.

Kinoshita et al. (1992) "A member of the C/EBP family, NF-IL6β, forms a heterodimer and transcriptionally synergizes with NF-IL6," Proc. Natl. Acad. Sci. USA 89:1473-1476.

Akira et al. (1990) "A nuclear factor for IL-6 expression (NF-IL6) is a member of a C/EBP family," EMBO J. 9:1897-1906.

Buck et al. (2001) "C/EMPβ phosphorylation by RSK creates a functional XEXD caspase inhibory box critical for cell survival," Mol. Cell 8:807-816.

Whitemarsh et al. (1996) "A central control for cell growth," Nature 403:255-256.

Mizushima et al., "pEF-BOS, a Powerful Mammalian Expression Vector," Nuc. Acids. Res. 18:5322 (1990).

Morris (1999) "A New Potent HIV-1 Reverse Transcriptase Inhibitor," J. Biol. Chem. 274:24942-24946.

Nakajima et al. (1996) "The Signal-Dependent Coactivator CBP Is a Nuclear Target for $pp90_{RSK}$," Cell 86:465-474.

Nebreda et al. (1999) "Cell Survival Demands Some Rsk," Science 286:1309-1310.

Pyronnet (1999) "Human eukaryotic translation initiation factor 4G (eIF4G) recruits Mnk1 to phosphorylate eIF4E," EMBO J. 18:270-279.

Ritter et al. (2000) "Nuclear localization of procaspase-9 and processing by a caspase-3-like activity in mammary epithelial cells," Eur. J. Cell Biol. 79:358-364.

Roberge et al. (1995) "A Strategy for a Convergent Synthesis of N-Linked Glycopeptides on a Solid Support," Science 269:202-204.

Rothwell et al. (1997) "The Role of Interleukin 1 in Acute Neurodegeneration and Stroke: Pathophysiological and Therapeutic Implications," J. Clin. Invest. 100:2648-2652.

Rudel et al. (1997) "Membrane and Morphological Changes in Apoptotic Cells Regulated by Caspase-Mediated Activation of PAK2," Science 276:1571-574.

Rudolph et al. (2000) "Inhibition of Experimental Liver Cirrhosis in Mice by Telomerase Gene Delivery," Science 287:1253-1258.

Sassone-Corsi et al. (1999) "Requirement of Rsk-2 for Epidermal Growth Factor-Activated Phosphorylation of Histone H3," Science 285:886-891.

Scudiero et al. (1988) "Evaluation of a Soluble Tetrazolium/ Formazan Assay for Cell Growth and Drug Sensitivity in Culture Using Human and Other Tumor Cell Lines," Cancer Res. 48:4827.

Stennicke et al. (1997) "Caspase Assays," Meth. Enzymol. 322:91-100.

Thomson et al. (1999) "The nucleosomal responose associated with immediate-early gene induction is mediated via alternative MAP kinase cascades: MSKI as a potential histone H3/HMG-14 kinase," EMBO J. 17:4779-4793.

Thornberry et al. (1997) "A Combinatorial Approach Defines Specifities of Members of the Caspase Family and Granzyme B," J. Biol. Chem. 272:17907-17911.

Thornberry et al. (1998) "Caspases: Enemies Within," Science 281:1312-1316.

Trautwein et al. (1993) "Transactivation by NF-IL6/LAP is enhanced by phosphorylation of its activation domain," Nature 364:544-547.

Uetsuki et al. (1989) "Isolation and Characterization of the Human Chromosomal Gene for Polypeptide Chain Elongation Factor-1α," J. Biol. Chem. 264:5791-5798.

Voss et al. (1986) "The Role of Enhancers in the Regulation of Cell-Type-Specific Transcriptional Control," Trends Biochem. Sci. 11:287-289.

Wang et al. (1996) "TNF- and Cancer Therapy-Induced Apoptosis: Potentiation by Inhibition of NF-B," Science 274:784-787.

Whitmarsh et al. (2000) "Transcription factor AP-1 regulation by mitogen-activated protein kinase signal transduction pathways," J. Mol. Med. 74:589-607.

Wilson et al. (1994) "Structure and mechanism of interleukinp1β converting enzyme," Nature 370:270-275.

Zhou et al. (1997) "Target Protease Specificity of the Viral Serpin CrmA," J. Biol. Chem. 272:7797-7800.

Müller et al. (1995) "NF-M (chicken C/EBPβ) induces eosinophilic differentiation and apoptosis in a hematopoietic progenitor cell line," EMBO J. 14:6127-6135.

Zhu et al. (1997) "Expression of exogenous NF-IL6 induces apoptosis in Sp2/0-Ag14 myeloma cells," DNA and Cell Biology 16:127-135.

Descombes et al. (1990) "LAP, a novel member of the C/EBP gene family, encodes a liver-enriched transcriptional activator protein," Genes and Devel. 4:1541-1551.

Cao et al. (1991) "Regulated expression of three C/EBP isoforms during adipose conversion of 3T3-L1 cells," Genes and Devel. 5:1538-1552.

Genbank accession No. AAR40801 (2003).

* cited by examiner

FIGURE 8

SEQ ID NO:1

```
   1 gcccgttgcc aggcgccgcc ttataaacct cccgctcggc cgccgccgcg ccgagtccga
  61 gccgcgcacg ggaccgggac gcagcggagc ccgcgggccc cgcgttcatg caccgcctgc
 121 tggcctggga cgcagcatgc ctcccgccgc cgcccgccgc ctttagaccc atggaagtgg
 181 ccaacttcta ctacgagccc gactgcctgg cctacggggc caaggcggcc cgcgccgcgc
 241 cgcgcgcccc cgccgccgag ccggccattg gcgagcacga gcgcgccatc gacttcagcc
 301 cctacctgga gccgctcgcg cccgccgcgg acttcgccgc gcccgcgccc gcgcaccacg
 361 acttcctctc cgacctcttc gccgacgact acggcgccaa gccgagcaag aagccggccg
 421 actacggtta cgtgagcctc ggccgcgcgg gcgccaaggc cgcgccgccc gcctgcttcc
 481 cgccgccgcc tcccgcggcg ctcaaggcgg agccgggctt cgaacccgcg gactgcaagc
 541 gcgcggacga cgcgcccgcc atggcggccg gtttcccgtt cgccctgcgc gcctacctgg
 601 gctaccaggc gacgccgagc ggcagcagcg gcagcctgtc cacgtcgtcg tcgtccagcc
 661 cgcccggcac gccgagcccc gccgacgcca aggccgcgcc cgccgcctgc ttcgcggggc
 721 cgccggccgc gccgccaag gccaaggcca agaagacggt ggacaagctg agcgacgagt
 781 acaagatgcg gcgcgagcgc aacaacatcg cggtgcgcaa gagccgcgac aaggccaaga
 841 tgcgcaacct ggagacgcag cacaaggtgc tggagctgac ggcggagaac gagcggctgc
 901 agaagaaggt ggagcagctg tcgcgagagc tcagcaccct gcggaacttg ttcaagcagc
 961 tgcccgagcc gctgctggcc tcggcgggcc actgctagcg cggcgcggtg gcgtggggga
1021 cgccgcggcc accgtgcgcc ctgccccgcg cgctccggcc ccgcgcgcgc gcccggacca
1081 ccgtgcgtgc cctgcgcgca cctgcacctg caccgagggg acatccgcgg cacaccgcgg
1141 gcacgcgcgg cgcacgcacc tgcacagcgc accgggtttc gggacttgat gcaatccgga
1201 tcaaacgtgg ctgagcgcgt gtggacacgg gactacgcaa cacacgtgta actgtctagc
1261 cgggccctga gtaatcacct taaagatgtt cctgcggggt tgttgatgtt tttggttttg
1321 tttttgtttt ttgttttgtt ttgttttttt tttggtctt attatttttt ttgtattata
1381 taaaaaagtt ctatttctat gagaaaagag gcgtatgtat atttgagaac ctttccgtt
1441 tcgagcatta aagtgaagac attttaataa actttttttgg gagaatgttt aaaagccaaa
```

SEQ ID NO:2

MHRLLAWDAACLPPPPAAFRPMEVANFYYEPDCLAYGAKAARAAPRAPAAEPA
IGEHERAIDFSPYLEPLAPAADFAAPAPAHHDFLSDLFADDYGAKPSKKPADYGY
VSLGRAGAKAAPPACFPPPPPAALKAEPGFEPADCKRADDAPAMAAGFPFALRA
YLGYQATPSGSSGSLSTSSSSSPPGTPSPADAKAAPAACFAGPPAAPAKAKAKKT
VDKLSDEYKMRRERNNIAVRKSRDKAKMRNLETQHKVLELTAENERLQKKVEQ
LSRELSTLRNLFKQLPEPLLASAGHC

FIGURE 9

SEQ ID NO:3

MHRLLAWDAACLPPPPAAFRPMEVANFYYEPDCLAYGAKAARAAPRAPAAEPA
IGEHERAIDFSPYLEPLAPAADFAAPAPAHHDFLSDLFADDYGAKPSKKPADYGY
VSLGRAGAKAAPPACFPPPPPAALKAEPGFEPADCKRADDAPAMAAGFPFALRA
YLGYQATPSGSSGSLSTSSSSSPPGTPSPADAKAAPAACFAGPPAAPAKAKAKKA
VDKLSDEYKMRRERNNIAVRKSRDKAKMRNLETQHKVLELTAENERLQKKVEQ
LSRELSTLRNLFKQLPEPLLASAGHC

SEQ ID NO:4

MHRLLAWDAACLPPPPAAFRPMEVANFYYEPDCLAYGAKAARAAPRAPAAEPA
IGEHERAIDFSPYLEPLAPAADFAAPAPAHHDFLSDLFADDYGAKPSKKPADYGY
VSLGRAGAKAAPPACFPPPPPAALKAEPGFEPADCKRADDAPAMAAGFPFALRA
YLGYQATPSGSSGSLSTSSSSSPPGTPSPADAKAAPAACFAGPPAAPAKAKAKKE
VDKLSDEYKMRRERNNIAVRKSRDKAKMRNLETQHKVLELTAENERLQKKVEQ
LSRELSTLRNLFKQLPEPLLASAGHC

FIGURE 10

SEQ ID NO:5

```
   1 cacgtcagcc ggggctagaa aaggcggcgg ggctgggccc agcgaggtga cagcctcgct
  61 tggacgcaga gcccggcccg acgccgccat gacggccgcg ctcttcagcc tggacggccc
 121 ggccggcggc gcgccctggc ctgcggagcc tgcgcccttc tacgaaccgg gccggcggg
 181 caagccgggc cgcggggccg agccaggggc cctaggcgag ccaggcgccg ccgccccgc
 241 catgtacgac gacgagagcg ccatcgactt cagcgcctac atcgactcca tggccgccgt
 301 gcccaccctg gagctgtgcc acgacgagct cttcgccgac ctcttcaaca gcaatcacaa
 361 ggcgggcggc gcggggcccc tggagcttct tcccggcggc cccgcgcgcc ccttgggccc
 421 gggccctgcc gctccccgcc tgctcaagcg cgagcccgac tggggcgacg gcgacgcgcc
 481 cggctcgctg ttgccgcgc aggtgggccc gtgcgcacag accgtggtga gcttggcggc
 541 cgcagggcag cccacccgc ccacgtcgcc ggagccgccg cgcagcagcc caggcagac
 601 ccccgcgccc ggccccgccc gggagaagag cgccggcaag aggggcccgg accgcggcag
 661 ccccgagtac cggcagcggc gcgagcgcaa caacatcgcc gtgcgcaaga gccgcgacaa
 721 ggccaagcgg cgcaaccagg agatgcagca gaagttggtg gagctgtcgg ctgagaacga
 781 gaagctgcac cagcgcgtgg agcagctcac gcgggacctg gccggcctcc ggcagttctt
 841 caagcagctg cccagcccgc ccttcctgcc ggccgccggg acagcagact gccggtaacg
 901 cgcggccggg gcgggagaga ctcagcaacg acccatacct cagacccgac ggcccggagc
 961 ggacgccctg ctgccgacgc cagagccgcc gcgtgcccgc tgcagtttct tggacataga
1021 ccaaagaagc tacagcctgg acttaccacc actaaactgc gagagaagct aaacgtgttt
1081 attttcctt aaattatttt tgtaatggta gctttttcta catcttactc ctgttgatgc
1141 agctaaggta catttgtaaa aagaaaaaaa accagacttt tcagacaaac cctttgtatt
1201 gtagataaga ggaaaagact gagcatgctc acttttttat attaattttt aggacagtat
1261 ttgtaagaat aaagcagcat ttgaaatgcc cct
```

SEQ ID NO:6

MTAALFSLDGPAGGAPWPAEPAPFYEPGRAGKPGRGAEPGALGEPGAAAPAMY
DDESAIDFSAYIDSMAAVPTLELCHDELFADLFNSNHKAGGAGPLELLPGGPARP
LGPGPAAPRLLKREPDWGDGDAPGSLLPAQVGPCAQTVVSLAAAGQPTPPTSPE
PPRSSPRQTPAPGPAREKSAGKRGPDRGSPEYRQRRERNNIAVRKSRDKAKRRNQ
EMQQKLVELSAENEKLHQRVEQLTRDLAGLRQFFKQLPSPPFLPAAGTADCR

FIGURE 11

SEQ ID NO:7

MTAALFSLDG PAGGAPWPAE PAPFYEPGRA GKPGRGAEPG ALGEPGAAAP
AMYDDESAID FSAYIDSMAA VPTLELCHDE LFADLFNSNH KAGGAGPLEL
LPGGPARPLG PGPAAPRLLK REPDWGDGDA PGSLLPAQVG PCAQTVVSLA
AAGQPTPPTS PEPPRSSPRQ TPAPGPAREK SAGKRGPDRG SPEYRQRRER
NNIAVRKSRD KAKRRNQEMQ QKLVELSAEN EKLHQRVEQL TRDLAGLRQF
FKQLPSPPFL PAAGAADCR

SEQ ID NO:8

MTAALFSLDGPAGGAPWPAEPAPFYEPGRAGKPGRGAEPGALGEPGAAAPAMY
DDESAIDFSAYIDSMAAVPTLELCHDELFADLFNSNHKAGGAGPLELLPGGPARP
LGPGPAAPRLLKREPDWGDGDAPGSLLPAQVGPCAQTVVSLAAAGQPTPPTSPE
PPRSSPRQTPAPGPAREKSAGKRGPDRGSPEYRQRRERNNIAVRKSRDKAKRRNQ
EMQQKLVELSAENEKLHQRVEQLTRDLAGLRQFFKQLPSPPFLPAAGEADCR

FIGURE 12

SEQ ID NO:9

MQRLVAWDPA CLPLPPPPPA FKSMEVANFY YEADCLAAAY GGKAAPAAPP
AARPGPRPPA GELGSIGDHE RAIDFSPYLE PLGAPQAPAP ATATDTFEAA
PPAPAPAPAS SGQHHDFLSD LFSDDYGGKN CKKPAEYGYV SLGRLGAAKG
ALHPGCFAPL HPPPPPPPPP AELKAEPGFE PADCKRKEEA GAPGGGAGMA
AGFPYALRAY LGYQAVPSGS SGSLSTSSSS SPPGTPSPAD AKAPPTACYA
GAGPAPSQVK SKAKKTVDKH SDEYKIRRER NNIAVRKSRD KAKMRNLETQ
HKVLELTAEN ERLQKKVEQL SRELSTLRNL FKQLPEPLLA SSGHC

SEQ ID NO:10

MQRLVAWDPA CLPLPPPPPA FKSMEVANFY YEADCLAAAY GGKAAPAAPP
AARPGPRPPA GELGSIGDHE RAIDFSPYLE PLGAPQAPAP ATATDTFEAA
PPAPAPAPAS SGQHHDFLSD LFSDDYGGKN CKKPAEYGYV SLGRLGAAKG
ALHPGCFAPL HPPPPPPPPP AELKAEPGFE PADCKRKEEA GAPGGGAGMA
AGFPYALRAY LGYQAVPSGS SGSLSTSSSS SPPGTPSPAD AKAPPTACYA
GAGPAPSQVK SKAKKAVDKH SDEYKIRRER NNIAVRKSRD KAKMRNLETQ
HKVLELTAEN ERLQKKVEQL SRELSTLRNL FKQLPEPLLA SSGHC

SEQ ID NO:11

MQRLVAWDPA CLPLPPPPPA FKSMEVANFY YEADCLAAAY GGKAAPAAPP
AARPGPRPPA GELGSIGDHE RAIDFSPYLE PLGAPQAPAP ATATDTFEAA
PPAPAPAPAS SGQHHDFLSD LFSDDYGGKN CKKPAEYGYV SLGRLGAAKG
ALHPGCFAPL HPPPPPPPPP AELKAEPGFE PADCKRKEEA GAPGGGAGMA
AGFPYALRAY LGYQAVPSGS SGSLSTSSSS SPPGTPSPAD AKAPPTACYA
GAGPAPSQVK SKAKKEVDKH SDEYKIRRER NNIAVRKSRD KAKMRNLETQ
HKVLELTAEN ERLQKKVEQL SRELSTLRNL FKQLPEPLLA SSGHC

FIGURE 13

SEQ ID NO:18

```
   1 gtccttcgcg tcccggcggc gcggcggagg ggccggcgtg acgcagcggt tgctacgggc
  61 cgcccttata aataaccggg ctcaggagaa actttagcga gtcagagccg cgcacgggac
 121 tgggaagggg acccacccga gggtccagcc accagccccc tcactaatag cggccacccc
 181 ggcagcggcg gcagcagcag cagcgacgca gcggcgacag ctcagagcag ggaggccgcg
 241 cacctgcggg ccggccggag cgggcagccc caggcccccct ccccgggcac ccgcgttcat
 301 gcaacgcctg gtggcctggg acccagcatg tctcccctg ccgccgccgc cgcctgcctt
 361 taaatccatg gaagtggcca acttctacta cgaggcggac tgcttggctg ctgcgtacgg
 421 cggcaaggcg gcccccgcgg cgcccccgcg ggccagaccc gggccgcgcc ccccgccgg
 481 cgagctgggc agcatcggcg accacgagcg cgccatcgac ttcagcccgt acctggagcc
 541 gctgggcgcg ccgcaggccc cggcgcccgc cacggccacg gacaccttcg aggcggctcc
 601 gcccgcgccc gccccgcgc ccgcctcctc cgggcagcac cacgacttcc tctccgacct
 661 cttctccgac gactacgggg gcaagaactg caagaagccg ccgagtacg ctacgtgag
 721 cctgggcgc ctgggggctg ccaagggcgc gctgcacccc ggctgcttcg cgccctgca
 781 cccaccgccc ccgccgccgc cgccgccgcc cgagctcaag gcggagccgg gcttcgagcc
 841 cgcggactgc aagcggaagg aggaggccgg ggcgccgggc ggcggcgcag gcatggcggc
 901 gggcttcccg tacgcgctgc gcgcttacct cggctaccag gcggtgccga gcggcagcag
 961 cgggagcctc tccacgtcct cctcgtccag cccgcccggc acgccgagcc ccgctgacgc
1021 caaggccccc ccgaccgcct gctacgcggg ggccgggccg gcgccctcgc aggtcaagag
1081 caaggccaag aagaccgtgg acaagcacag cgacgagtac aagatccggc gcgagcgcaa
1141 caacatcgcc gtgcgcaaga gccgcgacaa ggccaagatg cgcaacctgg agacgcagca
1201 caaggtcctg gagctcacgg ccgagaacga gcggctgcag aagaaggtgg agcagctgtc
1261 gcgcgagctc agcacccgtc ggaacttgtt caagcagctg cccgagcccc tgctcgcctc
1321 ctccggccac tgctagcgcg gcccccgcgg cgtccccctg cggccgccg gggctgagac
1381 tccggggagc gcccgcgccc gcgccctcgc cccncccccc nnnnccgcaa aactttggca
1441 ctggggcact tggcagcngg ggagcccgtc ggtaatttta atattttatt atatatatat
1501 atctatattt tgccaaccaa ccgtacatgc agatggctcc cgccgtggt gtataaagaa
1561 gaaatgtcta tgtgtacaga tgaatgataa actctctgct ctccctctgc ccctctccag
1621 gcccgcgggg cggggccggt ttcgaagttg atgcaatcgg tttaaacatg gctgaacgcg
1681 tgtgtacacg ggactgacgc aacccacgtg taactgtcag ccgggccctg agtaatcgct
1741 taaagatgtt ctagggcttg ttgctgttga tgttttgttt tgttttgttt tttggtcttt
1801 ttttgtatta taaaaaataa tctatttcta tgagaaaaga ggcgtctgta tattttggga
1861 atcttttccg tttcaagcaa ttaagaacac ttttaataaa ctttttttg
```

SEQ ID NO:19

MQRLVAWDPACLPLPPPPPAFKSMEVANFYYEADCLAAAYGGKAAPAAPPAAR
PGPRPPAGELGSIGDHERAIDFSPYLEPLGAPQAPAPATATDTFEAAPPAPAPAPA
SSGQHHDFLSDLFSDDYGGKNCKKPAEYGYVSLGRLGAAKGALHPGCFAPLHPP
PPPPPPAELKAEPGFEPADCKRKEEAGAPGGGAGMAAGFPYALRAYLGYQAVP
SGSSGSLSTSSSSSPPGTPSPADAKAPPTACYAGAGPAPSQVKSKAKKTVDKHSD
EYKIRRERNNIAVRKSRDKAKMRNLETQHKVLELTAENERLQKKVEQLSRELST
LRNLFKQLPEPLLASSGHC

FIGURE 14

SEQ ID NO:20

MQRLVAWDPACLPLPPPPPAFKSMEVANFYYEADCLAAAYGGKAAPAAPPAAR
PGPRPPAGELGSIGDHERAIDFSPYLEPLGAPQAPAPATATDTFEAAPPAPAPAPA
SSGQHHDFLSDLFSDDYGGKNCKKPAEYGYVSLGRLGAAKGALHPGCFAPLHPP
PPPPPPPAELKAEPGFEPADCKRKEEAGAPGGGAGMAAGFPYALRAYLGYQAVP
SGSSGSLSTSSSSSPPGTPSPADAKAPPTACYAGAGPAPSQVKSKAKKAVDKHSD
EYKIRRERNNIAVRKSRDKAKMRNLETQHKVLELTAENERLQKKVEQLSRELST
LRNLFKQLPEPLLASSGHC

SEQ ID NO:21

MQRLVAWDPACLPLPPPPPAFKSMEVANFYYEADCLAAAYGGKAAPAAPPAAR
PGPRPPAGELGSIGDHERAIDFSPYLEPLGAPQAPAPATATDTFEAAPPAPAPAPA
SSGQHHDFLSDLFSDDYGGKNCKKPAEYGYVSLGRLGAAKGALHPGCFAPLHPP
PPPPPPPAELKAEPGFEPADCKRKEEAGAPGGGAGMAAGFPYALRAYLGYQAVP
SGSSGSLSTSSSSSPPGTPSPADAKAPPTACYAGAGPAPSQVKSKAKKEVDKHSD
EYKIRRERNNIAVRKSRDKAKMRNLETQHKVLELTAENERLQKKVEQLSRELST
LRNLFKQLPEPLLASSGHC

FIGURE 15

SEQ ID NO:22

```
   1 atgcaacgcc tggtggcctg ggacccagca tgtctccccc tgccgccgcc gccgcctgcc
  61 tttaaatcca tggaagtggc caacttctac tacgaggcgg actgcttggc tgctgcgtac
 121 ggcggcaagg cggcccccgc ggcgccccc  gcggccagac ccgggccgcg cccccccgcc
 181 ggcgagctgg gcagcatcgg cgaccacgag cgcgccatcg acttcagccc gtacctggag
 241 ccgctgggcg cgccgcaggc cccggcgccc gccacggcca cggacacctt cgaggcggct
 301 ccgccgcgc  ccgcccccgc gcccgcctcc tccgggcagc accacgactt cctctccgac
 361 ctcttctccg acgactacgg gggcaagaac tgcaagaagc cggccgagta cggctacgtg
 421 agcctggggc gcctgggggc tgccaagggc gcgctgcacc ccggctgctt cgcgcccctg
 481 cacccaccgc cccgccgcc  gccgccgccc gccgagctca aggcggagcc gggcttcgag
 541 cccgcggact gcaagcggaa ggaggaggcc ggggcgccgg gcggcggcgc aggcatggcg
 601 gcgggcttcc cgtacgcgct gcgcgcttac ctcggctacc aggcggtgcc gagcggcagc
 661 agcgggagcc tctccacgtc ctcctcgtcc agcccgcccg gcacgccgag cccgctgac
 721 gccaaggccc ccccgaccgc ctgctacgcg ggggccgggc cggcgccctc gcaggtcaag
 781 agcaaggcca agaagaccgt ggacaagcac agcgacgagt acaagatccg gcgcgagcgc
 841 aacaacatcg ccgtgcgcaa gagccgcgac aaggccaaga tgcgcaacct ggagacgcag
 901 cacaaggtcc tggagctcac ggccgagaac gagcggctgc agaagaaggt ggagcagctg
 961 tcgcgcgagc tcagcaccct gcggaacttg ttcaagcagc tgcccgagcc cctgctcgcc
1021 tcctccggcc actgctag
```

SEQ ID NO:23

MQRLVAWDPACLPLPPPPPAFKSMEVANFYYEADCLAAAYGGKAAPAAPPAAR
PGPRPPAGELGSIGDHERAIDFSPYLEPLGAPQAPAPATATDTFEAAPPAPAPAPA
SSGQHHDFLSDLFSDDYGGKNCKKPAEYGYVSLGRLGAAKGALHPGCFAPLHPP
PPPPPPPAELKAEPGFEPADCKRKEEAGAPGGGAGMAAGFPYALRAYLGYQAVP
SGSSGSLSTSSSSSPPGTPSPADAKAPPTACYAGAGPAPSQVKSKAKKTVDKHSD
EYKIRRERNNIAVRKSRDKAKMRNLETQHKVLELTAENERLQKKVEQLSRELST
LRNLFKQLPEPLLASSGHC

FIGURE 16

SEQ ID NO:24

MQRLVAWDPACLPLPPPPPAFKSMEVANFYYEADCLAAAYGGKAAPAAPPAAR
PGPRPPAGELGSIGDHERAIDFSPYLEPLGAPQAPAPATATDTFEAAPPAPAPAPA
SSGQHHDFLSDLFSDDYGGKNCKKPAEYGYVSLGRLGAAKGALHPGCFAPLHPP
PPPPPPPAELKAEPGFEPADCKRKEEAGAPGGGAGMAAGFPYALRAYLGYQAVP
SGSSGSLSTSSSSSPPGTPSPADAKAPPTACYAGAGPAPSQVKSKAKKAVDKHSD
EYKIRRERNNIAVRKSRDKAKMRNLETQHKVLELTAENERLQKKVEQLSRELST
LRNLFKQLPEPLLASSGHC

SEQ ID NO:25

MQRLVAWDPACLPLPPPPPAFKSMEVANFYYEADCLAAAYGGKAAPAAPPAAR
PGPRPPAGELGSIGDHERAIDFSPYLEPLGAPQAPAPATATDTFEAAPPAPAPAPA
SSGQHHDFLSDLFSDDYGGKNCKKPAEYGYVSLGRLGAAKGALHPGCFAPLHPP
PPPPPPPAELKAEPGFEPADCKRKEEAGAPGGGAGMAAGFPYALRAYLGYQAVP
SGSSGSLSTSSSSSPPGTPSPADAKAPPTACYAGAGPAPSQVKSKAKKEVDKHSD
EYKIRRERNNIAVRKSRDKAKMRNLETQHKVLELTAENERLQKKVEQLSRELST
LRNLFKQLPEPLLASSGHC

FIGURE 17

SEQ ID NO:12

```
   1 aggggcccccg gcgtgacgca gcccgttgcc aggcgccgcc ttataaacct ccgctcggcc
  61 gccgccgagc cgagtccgag ccgcgcacgg gaccgggacg cagcggagcc cgcgggcccc
 121 gcgttcatgc accgcctgct ggcctgggac gcagcatgcc tcccgccgcc gcccgccgcc
 181 tttagaccca tggaagtggc caacttctac tacgagcccg actgcctggc ctacgggcc
 241 aaggcggccc gcgccgcgcc gcgcgccccc gccgccgagc cggccatcgg cgagcacgag
 301 cgcgccatcg acttcagccc ctacctggag ccgctcgcgc ccgccgccgc ggacttcgcc
 361 gcgcccgcgc ccgccgcacca cgacttcctt tccgacctct tcgccgacga ctacggcgcc
 421 aagccgagca agaagccgtc cgactacggt tacgtgagcc tcggccgcgc gggcgccaag
 481 gccgcaccgc ccgcctgctt cccgccgccg cctcccgccg cactcaaggc cgagccgggc
 541 ttcgaacccg cggactgcaa gcgcgcggac gacgcgcccg ccatggcggc cggcttcccg
 601 ttcgccctgc gcgcctacct gggctaccag gcgacgccga gcggcagcag cggcagcctg
 661 tccacgtcgt cgtcgtccag cccgccgggg acgccgagcc ccgccgacgc caaggccgcg
 721 cccgccgcct gcttcgcggg gccgccggcc gcgcccgcca aggccaaggc caagaaggcg
 781 gtggacaagc tgagcgacga gtacaagatg cggcgcgagc gcaacaacat cgcggtgcgc
 841 aagagccgcg acaaggccaa gatgcgcaac ctgagacg agcacaaggt gctggagctg
 901 acggcggaga acgagcggct gcagaagaag gtggagcagc tgtcgcgaga gctcagcacg
 961 ctgcggaact tgttcaagca gctgccgag ccgctgctgg cctcggcggg tcactgctag
1021 cccggcgggg gtggcgtggg ggcgccgcgg ccaccctggg caccgtgcgc cctgcccgc
1081 gcgctccgtc cccgcgcgcg cccgggcacc gtgcgtgcac cgcgcgcacc tgcacctgca
1141 ccgaggggac accgtgggca ccgcgcgcac gcacctgcac cgcgcaccgg gtttcgggac
1201 ttgatgcaat ccggatcaaa cgtggctgag cgcgtgtgga cacgggactg acgcaacaca
1261 cgtgtaactg tcagccgggc cctgagtaat cacttaaaga tgttcctgcg gggttgttgc
1321 tgttgatgtt ttcttttttg tttttgttt tttgttttt ttttggtctt attattttt
1381 tgtattatat aaaaaagttc tatttctatg agaaagagg cgtatgtata ttttgagaac
1441 ctttccgtt tcgagcatta aagtgaagac attttaataa acttttttgg agaatgttta
1501 aaaaccttt gggggcagta gttggcttt gaaaaaaaat tttttttctt ccctcctgac
1561 tttggattta tgcgagattt tgttttttgt gtttctggtg tgtagggggc tgcgggttat
1621 tttggggttg tgtgtggtgg tgggtggggg tgtcgcatct gggtttttct cctccctgg
1681 cagatgggat gccag....t .........? ........... agtgccgggt caggaattc
```

SEQ ID NO:13

MHRLLAWDAACLPPPPAAFRPMEVANFYYEPDCLAYGAKAARAAPRAPAAEPA
IGEHERAIDFSPYLEPLAPAAADFAAPAPAHHDFLSDLFADDYGAKPSKKPSDYG
YVSLGRAGAKAAPPACFPPPPPAALKAEPGFEPADCKRADDAPAMAAGFPFALR
AYLGYQATPSGSSGSLSTSSSSSPPGTPSPADAKAAPAACFAGPPAAPAKAKAKK
AVDKLSDEYKMRRERNNIAVRKSRDKAKMRNLETQHKVLELTAENERLQKKVE
QLSRELSTLRNLFKQLPEPLLASAGHC

FIGURE 18

SEQ ID NO:14

MHRLLAWDAACLPPPPAAFRPMEVANFYYEPDCLAYGAKAARAAPRAPAAEPA
IGEHERAIDFSPYLEPLAPAAADFAAPAPAHHDFLSDLFADDYGAKPSKKPADYG
YVSLGRAGAKAAPPACFPPPPPAALKAEPGFEPADCKRADDAPAMAAGFPFALR
AYLGYQATPSGSSGSLSTSSSSSPPGTPSPADAKAAPAACFAGPPAAPAKAKAKK
AVDKLSDEYKMRRERNNIAVRKSRDKAKMRNLETQHKVLELTAENERLQKKVE
QLSRELSTLRNLFKQLPEPLLASAGHC

SEQ ID NO:15

MHRLLAWDAACLPPPPAAFRPMEVANFYYEPDCLAYGAKAARAAPRAPAAEPA
IGEHERAIDFSPYLEPLAPAAADFAAPAPAHHDFLSDLFADDYGAKPSKKPDDYG
YVSLGRAGAKAAPPACFPPPPPAALKAEPGFEPADCKRADDAPAMAAGFPFALR
AYLGYQATPSGSSGSLSTSSSSSPPGTPSPADAKAAPAACFAGPPAAPAKAKAKK
AVDKLSDEYKMRRERNNIAVRKSRDKAKMRNLETQHKVLELTAENERLQKKVE
QLSRELSTLRNLFKQLPEPLLASAGHC

SEQUENCE LISTING

<160> NUMBER OF SEQ ID NOS: 25

<210> SEQ ID NO 1
<211> LENGTH: 1500
<212> TYPE: DNA
<213> ORGANISM: Mus musculus

<400> SEQUENCE: 1

```
gcccgttgcc aggcgccgcc ttataaacct cccgctcggc cgccgccgcg ccgagtccga      60
gccgcgcacg ggaccgggac gcagcggagc ccgcgggccc cgcgttcatg caccgcctgc     120
tggcctggga cgcagcatgc ctcccgccgc cgcccgccgc ctttagaccc atggaagtgg     180
ccaacttcta ctacgagccc gactgcctgg cctacggggc caaggcggcc cgcgccgcgc     240
cgcgcgcccc cgccgccgag ccggccattg gcgagcacga gcgcgccatc gacttcagcc     300
cctacctgga gccgctcgcg cccgccgcgg acttcgccgc gcccgcgccc gcgcaccacg     360
acttcctctc cgacctcttc gccgacgact acggcgccaa gccgagcaag aagccggccg     420
actacggtta cgtgagcctc ggccgcgcgg gcgccaaggc cgcgccgccc gcctgcttcc     480
cgccgccgcc tcccgcggcg ctcaaggcgg agccgggctt cgaacccgcg gactgcaagc     540
gcgcggacga cgccgccgcc atggcggccg gtttcccgtt cgccctgcgc gcctacctgg     600
gctaccaggc gacgccgagc ggcagcagcg gcagcctgtc cacgtcgtcg tcgtccagcc     660
```

```
cgcccggcac gccgagcccc gccgacgcca aggccgcgcc cgccgcctgc ttcgcggggc    720
cgccggccgc gcccgccaag gccaaggcca agaagacggt ggacaagctg agcgacgagt    780
acaagatgcg gcgcgagcgc aacaacatcg cggtgcgcaa gagccgcgac aaggccaaga    840
tgcgcaacct ggagacgcag cacaaggtgc tggagctgac ggcggagaac gagcggctgc    900
agaagaaggt ggagcagctg tcgcgagagc tcagcaccct gcggaacttg ttcaagcagc    960 tgccgagcc gctgctggcc tcggcgggcc actgctagcg cggcgcggtg gcgtgggggg    1020
cgccgcggcc accgtgcgcc ctgccccgcg cgctccggcc ccgcgcgcgc gcccggacca    1080
ccgtgcgtgc cctgcgcgca cctgcacctg caccgagggg acaccgcggg cacaccgcgg    1140
gcacgcgcgg cgcacgcacc tgcacagcgc accgggtttc gggacttgat gcaatccgga    1200
tcaaacgtgg ctgagcgcgt gtggacacgg gactacgcaa cacacgtgta actgtctagc    1260
cgggccctga gtaatcacct taaagatgtt cctgcggggt tgttgatgtt tttggttttg    1320
tttttgtttt ttgttttgtt ttgtttttttt ttttggtctt attatttttt ttgtattata    1380
taaaaaagtt ctatttctat gagaaaagag gcgtatgtat atttgagaac cttttccgtt    1440
tcgagcatta aagtgaagac attttaataa actttttttgg gagaatgttt aaaagccaaa    1500
```

```
<210> SEQ ID NO 2
<211> LENGTH: 296
<212> TYPE: PRT
<213> ORGANISM: Mus musculus

<400> SEQUENCE: 2

Met His Arg Leu Leu Ala Trp Asp Ala Ala Cys Leu Pro Pro Pro
1               5                   10                  15

Ala Ala Phe Arg Pro Met Glu Val Ala Asn Phe Tyr Tyr Glu Pro Asp
            20                  25                  30

Cys Leu Ala Tyr Gly Ala Lys Ala Ala Arg Ala Ala Pro Arg Ala Pro
        35                  40                  45

Ala Ala Glu Pro Ala Ile Gly Glu His Glu Arg Ala Ile Asp Phe Ser
    50                  55                  60

Pro Tyr Leu Glu Pro Leu Ala Pro Ala Ala Asp Phe Ala Ala Pro Ala
65                  70                  75                  80

Pro Ala His His Asp Phe Leu Ser Asp Leu Phe Ala Asp Asp Tyr Gly
                85                  90                  95

Ala Lys Pro Ser Lys Lys Pro Ala Asp Tyr Gly Tyr Val Ser Leu Gly
            100                 105                 110

Arg Ala Gly Ala Lys Ala Ala Pro Pro Ala Cys Phe Pro Pro Pro
        115                 120                 125

Pro Ala Leu Lys Ala Glu Pro Gly Phe Glu Pro Ala Asp Cys Lys
    130                 135                 140

Arg Ala Asp Asp Ala Pro Ala Met Ala Ala Gly Phe Pro Phe Ala Leu
145                 150                 155                 160

Arg Ala Tyr Leu Gly Tyr Gln Ala Thr Pro Ser Gly Ser Ser Gly Ser
                165                 170                 175

Leu Ser Thr Ser Ser Ser Ser Ser Pro Pro Gly Thr Pro Ser Pro Ala
            180                 185                 190

Asp Ala Lys Ala Ala Pro Ala Ala Cys Phe Ala Gly Pro Pro Ala Ala
        195                 200                 205

Pro Ala Lys Ala Lys Ala Lys Lys Thr Val Asp Lys Leu Ser Asp Glu
    210                 215                 220
```

```
Tyr Lys Met Arg Arg Glu Arg Asn Asn Ile Ala Val Arg Lys Ser Arg
225                 230                 235                 240

Asp Lys Ala Lys Met Arg Asn Leu Glu Thr Gln His Lys Val Leu Glu
            245                 250                 255

Leu Thr Ala Glu Asn Glu Arg Leu Gln Lys Lys Val Glu Gln Leu Ser
            260                 265                 270

Arg Glu Leu Ser Thr Leu Arg Asn Leu Phe Lys Gln Leu Pro Glu Pro
        275                 280                 285

Leu Leu Ala Ser Ala Gly His Cys
    290                 295

<210> SEQ ID NO 3
<211> LENGTH: 296
212> TYPE: PRT
<213> ORGANISM: Mus musculus

<400> SEQUENCE: 3

Met His Arg Leu Leu Ala Trp Asp Ala Ala Cys Leu Pro Pro Pro Pro
1               5                   10                  15

Ala Ala Phe Arg Pro Met Glu Val Ala Asn Phe Tyr Tyr Glu Pro Asp
            20                  25                  30

Cys Leu Ala Tyr Gly Ala Lys Ala Ala Arg Ala Ala Pro Arg Ala Pro
        35                  40                  45

Ala Ala Glu Pro Ala Ile Gly Glu His Glu Arg Ala Ile Asp Phe Ser
    50                  55                  60

Pro Tyr Leu Glu Pro Leu Ala Pro Ala Ala Asp Phe Ala Ala Pro Ala
65                  70                  75                  80

Pro Ala His His Asp Phe Leu Ser Asp Leu Phe Ala Asp Asp Tyr Gly
                85                  90                  95

Ala Lys Pro Ser Lys Lys Pro Ala Asp Tyr Gly Tyr Val Ser Leu Gly
            100                 105                 110

Arg Ala Gly Ala Lys Ala Ala Pro Ala Cys Phe Pro Pro Pro Pro Pro
        115                 120                 125

Pro Ala Ala Leu Lys Ala Glu Pro Gly Phe Glu Pro Ala Asp Cys Lys
    130                 135                 140

Arg Ala Asp Asp Ala Pro Ala Met Ala Ala Gly Phe Pro Phe Ala Leu
145                 150                 155                 160

Arg Ala Tyr Leu Gly Tyr Gln Ala Thr Pro Ser Gly Ser Ser Gly Ser
                165                 170                 175

Leu Ser Thr Ser Ser Ser Ser Ser Pro Pro Gly Thr Pro Ser Pro Ala
            180                 185                 190

Asp Ala Lys Ala Ala Pro Ala Ala Cys Phe Ala Gly Pro Pro Ala Ala
        195                 200                 205

Pro Ala Lys Ala Lys Ala Lys Lys Ala Val Asp Lys Leu Ser Asp Glu
    210                 215                 220

Tyr Lys Met Arg Arg Glu Arg Asn Asn Ile Ala Val Arg Lys Ser Arg
225                 230                 235                 240

Asp Lys Ala Lys Met Arg Asn Leu Glu Thr Gln His Lys Val Leu Glu
                245                 250                 255

Leu Thr Ala Glu Asn Glu Arg Leu Gln Lys Lys Val Glu Gln Leu Ser
            260                 265                 270

Arg Glu Leu Ser Thr Leu Arg Asn Leu Phe Lys Gln Leu Pro Glu Pro
        275                 280                 285

Leu Leu Ala Ser Ala Gly His Cys
    290                 295
```

<210> SEQ ID NO 4
<211> LENGTH: 296
<212> TYPE: PRT
<213> ORGANISM: Mus musculus

<400> SEQUENCE: 4

```
Met His Arg Leu Leu Ala Trp Asp Ala Ala Cys Leu Pro Pro Pro Pro
 1               5                  10                  15

Ala Ala Phe Arg Pro Met Glu Val Ala Asn Phe Tyr Tyr Glu Pro Asp
             20                  25                  30

Cys Leu Ala Tyr Gly Ala Lys Ala Arg Ala Ala Pro Arg Ala Pro
         35                  40                  45

Ala Ala Glu Pro Ala Ile Gly Glu His Glu Arg Ala Ile Asp Phe Ser
     50                  55                  60

Pro Tyr Leu Glu Pro Leu Ala Pro Ala Ala Asp Phe Ala Ala Pro Ala
 65                  70                  75                  80

Pro Ala His His Asp Phe Leu Ser Asp Leu Phe Ala Asp Asp Tyr Gly
                 85                  90                  95

Ala Lys Pro Ser Lys Lys Pro Ala Asp Tyr Gly Tyr Val Ser Leu Gly
            100                 105                 110

Arg Ala Gly Ala Lys Ala Ala Pro Pro Ala Cys Phe Pro Pro Pro
        115                 120                 125

Pro Ala Ala Leu Lys Ala Glu Pro Gly Phe Glu Pro Ala Asp Cys Lys
    130                 135                 140

Arg Ala Asp Asp Ala Pro Ala Met Ala Ala Gly Phe Pro Phe Ala Leu
145                 150                 155                 160

Arg Ala Tyr Leu Gly Tyr Gln Ala Thr Pro Ser Gly Ser Ser Gly Ser
                165                 170                 175

Leu Ser Thr Ser Ser Ser Ser Pro Pro Gly Thr Pro Ser Pro Ala
                180                 185                 190

Asp Ala Lys Ala Ala Pro Ala Ala Cys Phe Ala Gly Pro Pro Ala Ala
            195                 200                 205

Pro Ala Lys Ala Lys Ala Lys Lys Glu Val Asp Lys Leu Ser Asp Glu
    210                 215                 220

Tyr Lys Met Arg Arg Glu Arg Asn Asn Ile Ala Val Arg Lys Ser Arg
225                 230                 235                 240

Asp Lys Ala Lys Met Arg Asn Leu Glu Thr Gln His Lys Val Leu Glu
                245                 250                 255

Leu Thr Ala Glu Asn Glu Arg Leu Gln Lys Lys Val Glu Gln Leu Ser
            260                 265                 270

Arg Glu Leu Ser Thr Leu Arg Asn Leu Phe Lys Gln Leu Pro Glu Pro
        275                 280                 285

Leu Leu Ala Ser Ala Gly His Cys
    290                 295
```

<210> SEQ ID NO 5
<211> LENGTH: 1293
<212> TYPE: DNA
<213> ORGANISM: Homo sapiens

<400> SEQUENCE: 5

```
cacgtcagcc ggggctagaa aaggcggcgg ggctgggccc agcgaggtga cagcctcgct    60
tggacgcaga gccggcccg  acgccgccat gacggccgcg ctcttcagcc tggacggccc   120
ggccggcggc gcgccctggc ctgcggagcc tgcgcccttc tacgaaccgg ccgggcggg   180
```

-continued

```
caagccgggc cgcggggccg agccaggggc cctaggcgag ccaggcgccg ccgccccgc      240 catgtacgac gacgagagcg ccatcgactt cagcgcctac atcgactcca tggccgccgt      300
gcccaccctg gagctgtgcc acgacgagct cttcgccgac ctcttcaaca gcaatcacaa      360
ggcgggcggc gcgggccccc tggagcttct tcccggcggc cccgcgcgcc ccttgggccc      420
gggccctgcc gctccccgcc tgctcaagcg cgagcccgac tggggcgacg gcgacgcgcc      480
cggctcgctg ttgcccgcgc aggtgggccc gtgcgcacag accgtggtga gcttggcggc      540
cgcagggcag cccaccccgc ccacgtcgcc ggagccgccg cgcagcagcc ccaggcagac      600
ccccgcgccc ggccccgccc gggagaagag cgccggcaag aggggcccgg accgcggcag      660
ccccgagtac cggcagcggc gcgagcgcaa caacatcgcc gtgcgcaaga gccgcgacaa      720
ggccaagcgg cgcaaccagg agatgcagca gaagttggtg gagctgtcgg ctgagaacga      780
gaagctgcac cagcgcgtgg agcagctcac gcgggacctg gccggcctcc ggcagttctt      840
caagcagctg cccagcccgc ccttcctgcc ggccgccggg acagcagact gccggtaacg      900
cgcggccggg gcgggagaga ctcagcaacg acccataacct cagacccgac ggcccggagc      960
ggacgccctg ctgccgacgc cagagccgcc gcgtgcccgc tgcagtttct tggacataga     1020
ccaaagaagc tacagcctgg acttaccacc actaaactgc gagagaagct aaacgtgttt     1080
attttccctt aaattatttt tgtaatggta gctttttcta catcttactc ctgttgatgc     1140
agctaaggta catttgtaaa agaaaaaaa accagacttt tcagacaaac cctttgtatt     1200
gtagataaga ggaaaagact gagcatgctc acttttttat attaatttttt aggacagtat     1260 ttgtaagaat aaagcagcat ttgaaatgcc cct                                  1293
```

<210> SEQ ID NO 6
<211> LENGTH: 269
<212> TYPE: PRT
<213> ORGANISM: Homo sapiens

<400> SEQUENCE: 6

```
Met Thr Ala Ala Leu Phe Ser Leu Asp Gly Pro Ala Gly Gly Ala Pro
1               5                   10                  15

Trp Pro Ala Glu Pro Ala Pro Phe Tyr Glu Pro Gly Arg Ala Gly Lys
                20                  25                  30

Pro Gly Arg Gly Ala Glu Pro Gly Ala Leu Gly Glu Pro Gly Ala Ala
            35                  40                  45

Ala Pro Ala Met Tyr Asp Asp Glu Ser Ala Ile Asp Phe Ser Ala Tyr
        50                  55                  60

Ile Asp Ser Met Ala Ala Val Pro Thr Leu Glu Leu Cys His Asp Glu
65                  70                  75                  80

Leu Phe Ala Asp Leu Phe Asn Ser Asn His Lys Ala Gly Gly Ala Gly
                85                  90                  95

Pro Leu Glu Leu Leu Pro Gly Gly Pro Ala Arg Pro Leu Gly Pro Gly
            100                 105                 110

Pro Ala Ala Pro Arg Leu Leu Lys Arg Glu Pro Asp Trp Gly Asp Gly
        115                 120                 125

Asp Ala Pro Gly Ser Leu Leu Pro Ala Gln Val Gly Pro Cys Ala Gln
    130                 135                 140

Thr Val Val Ser Leu Ala Ala Ala Gly Gln Pro Thr Pro Thr Ser
145                 150                 155                 160

Pro Glu Pro Pro Arg Ser Ser Pro Arg Gln Thr Pro Ala Pro Gly Pro
                165                 170                 175
```

```
Ala Arg Glu Lys Ser Ala Gly Lys Arg Gly Pro Asp Arg Gly Ser Pro
            180                 185                 190

Glu Tyr Arg Gln Arg Arg Glu Arg Asn Asn Ile Ala Val Arg Lys Ser
        195                 200                 205

Arg Asp Lys Ala Lys Arg Arg Asn Gln Glu Met Gln Gln Lys Leu Val
    210                 215                 220

Glu Leu Ser Ala Glu Asn Glu Lys Leu His Gln Arg Val Glu Gln Leu
225                 230                 235                 240

Thr Arg Asp Leu Ala Gly Leu Arg Gln Phe Phe Lys Gln Leu Pro Ser
                245                 250                 255

Pro Pro Phe Leu Pro Ala Ala Gly Thr Ala Asp Cys Arg
            260                 265

<210> SEQ ID NO 7
<211> LENGTH: 269
<212> TYPE: PRT
<213> ORGANISM: Homo sapiens

<400> SEQUENCE: 7

Met Thr Ala Ala Leu Phe Ser Leu Asp Gly Pro Ala Gly Gly Ala Pro
1               5                   10                  15

Trp Pro Ala Glu Pro Ala Pro Phe Tyr Glu Pro Gly Arg Ala Gly Lys
            20                  25                  30

Pro Gly Arg Gly Ala Glu Pro Gly Ala Leu Gly Glu Pro Gly Ala Ala
        35                  40                  45

Ala Pro Ala Met Tyr Asp Asp Glu Ser Ala Ile Asp Phe Ser Ala Tyr
    50                  55                  60

Ile Asp Ser Met Ala Ala Val Pro Thr Leu Glu Leu Cys His Asp Glu
65                  70                  75                  80

Leu Phe Ala Asp Leu Phe Asn Ser Asn His Lys Ala Gly Gly Ala Gly
                85                  90                  95

Pro Leu Glu Leu Leu Pro Gly Gly Pro Ala Arg Pro Leu Gly Pro Gly
            100                 105                 110

Pro Ala Ala Pro Arg Leu Leu Lys Arg Glu Pro Asp Trp Gly Asp Gly
        115                 120                 125

Asp Ala Pro Gly Ser Leu Leu Pro Ala Gln Val Gly Pro Cys Ala Gln
    130                 135                 140

Thr Val Val Ser Leu Ala Ala Ala Gly Gln Pro Thr Pro Pro Thr Ser
145                 150                 155                 160

Pro Glu Pro Pro Arg Ser Ser Pro Arg Gln Thr Pro Ala Pro Gly Pro
                165                 170                 175

Ala Arg Glu Lys Ser Ala Gly Lys Arg Gly Pro Asp Arg Gly Ser Pro
            180                 185                 190

Glu Tyr Arg Gln Arg Arg Glu Arg Asn Asn Ile Ala Val Arg Lys Ser
        195                 200                 205

Arg Asp Lys Ala Lys Arg Arg Asn Gln Glu Met Gln Gln Lys Leu Val
    210                 215                 220

Glu Leu Ser Ala Glu Asn Glu Lys Leu His Gln Arg Val Glu Gln Leu
225                 230                 235                 240

Thr Arg Asp Leu Ala Gly Leu Arg Gln Phe Phe Lys Gln Leu Pro Ser
                245                 250                 255

Pro Pro Phe Leu Pro Ala Ala Gly Ala Ala Asp Cys Arg
            260                 265
```

```
<210> SEQ ID NO 8
<211> LENGTH: 269
<212> TYPE: PRT
<213> ORGANISM: Homo sapiens

<400> SEQUENCE: 8

Met Thr Ala Ala Leu Phe Ser Leu Asp Gly Pro Ala Gly Gly Ala Pro
1               5                   10                  15

Trp Pro Ala Glu Pro Ala Pro Phe Tyr Glu Pro Gly Arg Ala Gly Lys
            20                  25                  30

Pro Gly Arg Gly Ala Glu Pro Gly Ala Leu Gly Glu Pro Gly Ala Ala
        35                  40                  45

Ala Pro Ala Met Tyr Asp Asp Glu Ser Ala Ile Asp Phe Ser Ala Tyr
    50                  55                  60

Ile Asp Ser Met Ala Ala Val Pro Thr Leu Glu Leu Cys His Asp Glu
65                  70                  75                  80

Leu Phe Ala Asp Leu Phe Asn Ser Asn His Lys Ala Gly Gly Ala Gly
                85                  90                  95

Pro Leu Glu Leu Leu Pro Gly Pro Ala Arg Pro Leu Gly Pro Gly Pro
            100                 105                 110

Pro Ala Ala Pro Arg Leu Leu Lys Arg Glu Pro Asp Trp Gly Asp Gly
        115                 120                 125

Asp Ala Pro Gly Ser Leu Leu Pro Ala Gln Val Gly Pro Cys Ala Gln
    130                 135                 140

Thr Val Val Ser Leu Ala Ala Ala Gly Gln Pro Thr Pro Pro Thr Ser
145                 150                 155                 160

Pro Glu Pro Pro Arg Ser Ser Pro Arg Gln Thr Pro Ala Pro Gly Pro
                165                 170                 175

Ala Arg Glu Lys Ser Ala Gly Lys Arg Gly Pro Asp Arg Gly Ser Pro
            180                 185                 190

Glu Tyr Arg Gln Arg Arg Glu Arg Asn Asn Ile Ala Val Arg Lys Ser
            195                 200                 205

Arg Asp Lys Ala Lys Arg Arg Asn Gln Glu Met Gln Gln Lys Leu Val
    210                 215                 220

Glu Leu Ser Ala Glu Asn Glu Lys Leu His Gln Arg Val Glu Gln Leu
225                 230                 235                 240

Thr Arg Asp Leu Ala Gly Leu Arg Gln Phe Phe Lys Gln Leu Pro Ser
                245                 250                 255

Pro Pro Phe Leu Pro Ala Ala Gly Glu Ala Asp Cys Arg
            260                 265

<210> SEQ ID NO 9
<211> LENGTH: 345
<212> TYPE: PRT
<213> ORGANISM: Homo sapiens

<400> SEQUENCE: 9

Met Gln Arg Leu Val Ala Trp Asp Pro Ala Cys Leu Pro Leu Pro Pro
1               5                   10                  15

Pro Pro Pro Ala Phe Lys Ser Met Glu Val Ala Asn Phe Tyr Tyr Glu
            20                  25                  30

Ala Asp Cys Leu Ala Ala Ala Tyr Gly Gly Lys Ala Ala Pro Ala Ala
        35                  40                  45

Pro Pro Ala Ala Arg Pro Gly Pro Arg Pro Pro Ala Gly Glu Leu Gly
    50                  55                  60

Ser Ile Gly Asp His Glu Arg Ala Ile Asp Phe Ser Pro Tyr Leu Glu
```

```
                65                  70                  75                  80
Pro Leu Gly Ala Pro Gln Ala Pro Ala Pro Ala Thr Ala Thr Asp Thr
                    85                  90                  95

Phe Glu Ala Ala Pro Pro Ala Pro Ala Pro Ala Pro Ala Ser Ser Gly
                    100                 105                 110

Gln His His Asp Phe Leu Ser Asp Leu Phe Ser Asp Asp Tyr Gly Gly
                    115                 120                 125

Lys Asn Cys Lys Lys Pro Ala Glu Tyr Gly Tyr Val Ser Leu Gly Arg
    130                 135                 140

Leu Gly Ala Ala Lys Gly Ala Leu His Pro Gly Cys Phe Ala Pro Leu
145                 150                 155                 160

His Pro Pro Pro Pro Pro Pro Pro Ala Glu Leu Lys Ala Glu
                    165                 170                 175

Pro Gly Phe Glu Pro Ala Asp Cys Lys Arg Lys Glu Glu Ala Gly Ala
                180                 185                 190

Pro Gly Gly Gly Ala Gly Met Ala Ala Gly Phe Pro Tyr Ala Leu Arg
                195                 200                 205

Ala Tyr Leu Gly Tyr Gln Ala Val Pro Ser Gly Ser Ser Gly Ser Leu
    210                 215                 220

Ser Thr Ser Ser Ser Ser Ser Pro Pro Gly Thr Pro Ser Pro Ala Asp
225                 230                 235                 240

Ala Lys Ala Pro Pro Thr Ala Cys Tyr Ala Gly Ala Gly Pro Ala Pro
                245                 250                 255

Ser Gln Val Lys Ser Lys Ala Lys Lys Thr Val Asp Lys His Ser Asp
                260                 265                 270

Glu Tyr Lys Ile Arg Arg Glu Arg Asn Asn Ile Ala Val Arg Lys Ser
                275                 280                 285

Arg Asp Lys Ala Lys Met Arg Asn Leu Glu Thr Gln His Lys Val Leu
    290                 295                 300

Glu Leu Thr Ala Glu Asn Glu Arg Leu Gln Lys Lys Val Glu Gln Leu
305                 310                 315                 320

Ser Arg Glu Leu Ser Thr Leu Arg Asn Leu Phe Lys Gln Leu Pro Glu
                325                 330                 335

Pro Leu Leu Ala Ser Ser Gly His Cys
                340                 345

<210> SEQ ID NO 10
<211> LENGTH: 345
<212> TYPE: PRT
<213> ORGANISM: Homo sapiens

<400> SEQUENCE: 10

Met Gln Arg Leu Val Ala Trp Asp Pro Ala Cys Leu Pro Leu Pro Pro
1               5                   10                  15

Pro Pro Pro Ala Phe Lys Ser Met Glu Val Ala Asn Phe Tyr Tyr Glu
                20                  25                  30

Ala Asp Cys Leu Ala Ala Ala Tyr Gly Gly Lys Ala Ala Pro Ala Ala
                35                  40                  45

Pro Pro Ala Ala Arg Pro Gly Pro Arg Pro Pro Ala Gly Glu Leu Gly
    50                  55                  60

Ser Ile Gly Asp His Glu Arg Ala Ile Asp Phe Ser Pro Tyr Leu Glu
65                  70                  75                  80

Pro Leu Gly Ala Pro Gln Ala Pro Ala Pro Ala Thr Ala Thr Asp Thr
                85                  90                  95
```

```
Phe Glu Ala Ala Pro Pro Ala Pro Ala Pro Ala Ser Ser Gly
            100                 105                 110

Gln His His Asp Phe Leu Ser Asp Leu Phe Ser Asp Asp Tyr Gly Gly
            115                 120                 125

Lys Asn Cys Lys Lys Pro Ala Glu Tyr Gly Tyr Val Ser Leu Gly Arg
130                 135                 140

Leu Gly Ala Ala Lys Gly Ala Leu His Pro Gly Cys Phe Ala Pro Leu
145                 150                 155                 160

His Pro Pro Pro Pro Pro Pro Pro Ala Glu Leu Lys Ala Glu
            165                 170                 175

Pro Gly Phe Glu Pro Ala Asp Cys Lys Arg Lys Glu Glu Ala Gly Ala
            180                 185                 190

Pro Gly Gly Gly Ala Gly Met Ala Ala Gly Phe Pro Tyr Ala Leu Arg
            195                 200                 205

Ala Tyr Leu Gly Tyr Gln Ala Val Pro Ser Gly Ser Ser Gly Ser Leu
            210                 215                 220

Ser Thr Ser Ser Ser Ser Pro Pro Gly Thr Pro Ser Pro Ala Asp
225                 230                 235                 240

Ala Lys Ala Pro Pro Thr Ala Cys Tyr Ala Gly Ala Gly Pro Ala Pro
            245                 250                 255

Ser Gln Val Lys Ser Lys Ala Lys Lys Ala Val Asp Lys His Ser Asp
            260                 265                 270

Glu Tyr Lys Ile Arg Arg Glu Arg Asn Asn Ile Ala Val Arg Lys Ser
            275                 280                 285

Arg Asp Lys Ala Lys Met Arg Asn Leu Glu Thr Gln His Lys Val Leu
            290                 295                 300

Glu Leu Thr Ala Glu Asn Glu Arg Leu Gln Lys Lys Val Glu Gln Leu
305                 310                 315                 320

Ser Arg Glu Leu Ser Thr Leu Arg Asn Leu Phe Lys Gln Leu Pro Glu
            325                 330                 335

Pro Leu Leu Ala Ser Ser Gly His Cys
            340                 345

<210> SEQ ID NO 11
<211> LENGTH: 345
<212> TYPE: PRT
<213> ORGANISM: Homo sapiens

<400> SEQUENCE: 11

Met Gln Arg Leu Val Ala Trp Asp Pro Ala Cys Leu Pro Leu Pro Pro
1               5                   10                  15

Pro Pro Pro Ala Phe Lys Ser Met Glu Val Ala Asn Phe Tyr Tyr Glu
            20                  25                  30

Ala Asp Cys Leu Ala Ala Ala Tyr Gly Gly Lys Ala Ala Pro Ala Ala
            35                  40                  45

Pro Pro Ala Ala Arg Pro Gly Pro Arg Pro Pro Ala Gly Glu Leu Gly
            50                  55                  60

Ser Ile Gly Asp His Glu Arg Ala Ile Asp Phe Ser Pro Tyr Leu Glu
65                  70                  75                  80

Pro Leu Gly Ala Pro Gln Ala Pro Ala Pro Ala Thr Ala Thr Asp Thr
            85                  90                  95

Phe Glu Ala Ala Pro Pro Ala Pro Ala Pro Ala Pro Ala Ser Ser Gly
            100                 105                 110

Gln His His Asp Phe Leu Ser Asp Leu Phe Ser Asp Asp Tyr Gly Gly
            115                 120                 125
```

-continued

```
Lys Asn Cys Lys Lys Pro Ala Glu Tyr Gly Tyr Val Ser Leu Gly Arg
    130                 135                 140

Leu Gly Ala Ala Lys Gly Ala Leu His Pro Gly Cys Phe Ala Pro Leu
145                 150                 155                 160

His Pro Pro Pro Pro Pro Pro Pro Ala Glu Leu Lys Ala Glu
                165                 170                 175

Pro Gly Phe Glu Pro Ala Asp Cys Lys Arg Lys Glu Ala Gly Ala
            180                 185                 190

Pro Gly Gly Gly Ala Gly Met Ala Ala Gly Phe Pro Tyr Ala Leu Arg
            195                 200                 205

Ala Tyr Leu Gly Tyr Gln Ala Val Pro Ser Gly Ser Ser Gly Ser Leu
    210                 215                 220

Ser Thr Ser Ser Ser Ser Ser Pro Pro Gly Thr Pro Ser Pro Ala Asp
225                 230                 235                 240

Ala Lys Ala Pro Pro Thr Ala Cys Tyr Ala Gly Ala Gly Pro Ala Pro
                245                 250                 255

Ser Gln Val Lys Ser Lys Ala Lys Lys Glu Val Asp Lys His Ser Asp
            260                 265                 270

Glu Tyr Lys Ile Arg Arg Glu Arg Asn Asn Ile Ala Val Arg Lys Ser
    275                 280                 285

Arg Asp Lys Ala Lys Met Arg Asn Leu Glu Thr Gln His Lys Val Leu
    290                 295                 300

Glu Leu Thr Ala Glu Asn Glu Arg Leu Gln Lys Lys Val Glu Gln Leu
305                 310                 315                 320

Ser Arg Glu Leu Ser Thr Leu Arg Asn Leu Phe Lys Gln Leu Pro Glu
                325                 330                 335

Pro Leu Leu Ala Ser Ser Gly His Cys
            340                 345
```

<210> SEQ ID NO 12
<211> LENGTH: 1739
<212> TYPE: DNA
<213> ORGANISM: Rattus norvegicus

<400> SEQUENCE: 12

```
aggggccccg gcgtgacgca gcccgttgcc aggcgccgcc ttataaacct ccgctcggcc      60
gccgccgagc cgagtccgag ccgcgcacgg gaccgggacg cagcggagcc cgcgggcccc     120
gcgttcatgc accgcctgct ggcctgggac gcagcatgcc tccgccgcc gcccgccgcc     180
tttagaccca tggaagtggc caacttctac tacgagcccg actgcctggc ctacggggcc     240
aaggcggccc gcgccgcgcc gcgcgccccc gccgccgagc cggccatcgg cgagcacgag     300
cgcgccatcg acttcagccc ctacctggag ccgctcgcgc ccgccgccgc ggacttcgcc     360
gcgcccgcgc ccgcgcacca cgacttcctt tccgacctct tcgccgacga ctacggcgcc     420
aagccgagca agaagccgtc cgactacggt tacgtgagcc tcggccgcgc gggcgccaag     480
gccgcaccgc cgcctgcttt cccgccgccg cctcccgccg cactcaaggc cgagccgggc     540
ttcgaacccg cggactgcaa gcgcgcggac gacgcgcccg ccatggcggc cggcttcccg     600
ttcgccctgc gcgcctacct gggctaccag gcgacgccga gcggcagcag cggcagcctg     660
tccacgtcgt cgtcgtccag cccgcccggg acgccgagcc ccgccgacgc caaggccgcg     720
cccgccgcct gcttcgcggg gccgccggcc gcgcccgcca aggccaaggc caagaaggcg     780
gtggacaagc tgagcgacga gtacaagatg cggcgcgagc gcaacaacat cgcggtgcgc     840
```

```
aagagccgcg acaaggccaa gatgcgcaac ctggagacgc agcacaaggt gctggagctg    900
acggcggaga acgagcggct gcagaagaag gtggagcagc tgtcgcgaga gctcagcacg    960
ctgcggaact tgttcaagca gctgcccgag ccgctgctgg cctcggcggg tcactgctag   1020
cccggcgggg gtggcgtggg ggcgccgcgg ccacccgtggg caccgtgcgc cctgccccgc   1080
gcgctccgtc cccgcgcgcg cccgggcacc gtgcgtgcac cgcgcgcacc tgcacctgca   1140
ccgagggac accgtgggca ccgcgcgcac gcacctgcac cgcgcaccgg gtttcgggac    1200
ttgatgcaat ccggatcaaa cgtggctgag cgcgtgtgga cacgggactg acgcaacaca   1260
cgtgtaactg tcagccgggc cctgagtaat cacttaaaga tgttcctgcg gggttgttgc   1320
tgttgatgtt tttcttttg tttttgttt tttgtttttt ttttggtctt attattttt     1380
tgtattatat aaaaaagttc tatttctatg agaaaagagg cgtatgtata ttttgagaac   1440
cttttccgtt tcgagcatta aagtgaagac attttaataa acttttttgg agaatgttta   1500
aaaaccttt gggggcagta gttggctttt gaaaaaaaat tttttttctt ccctcctgac   1560
tttggattta tgcgagattt tgttttttgt gtttctggtg tgtaggggc tgcgggttat   1620
ttttgggttg tgtgtggtgg tgggtggggg tgtcgcatct gggtttttct cctcccctgg   1680
cagatgggat gccagcccct cccccagga gaggggcag agtgccgggt caggaattc     1739
```

<210> SEQ ID NO 13
<211> LENGTH: 297
<212> TYPE: PRT
<213> ORGANISM: Rattus norvegicus

<400> SEQUENCE: 13

```
Met His Arg Leu Leu Ala Trp Asp Ala Ala Cys Leu Pro Pro Pro
1               5                   10                  15

Ala Ala Phe Arg Pro Met Glu Val Ala Asn Phe Tyr Tyr Glu Pro Asp
            20                  25                  30

Cys Leu Ala Tyr Gly Ala Lys Ala Arg Ala Ala Pro Arg Ala Pro
        35                  40                  45

Ala Ala Glu Pro Ala Ile Gly Glu His Glu Arg Ala Ile Asp Phe Ser
    50                  55                  60

Pro Tyr Leu Glu Pro Leu Ala Pro Ala Ala Asp Phe Ala Ala Pro
65                  70                  75                  80

Ala Pro Ala His His Asp Phe Leu Ser Asp Leu Phe Ala Asp Asp Tyr
                85                  90                  95

Gly Ala Lys Pro Ser Lys Lys Pro Ser Asp Tyr Gly Tyr Val Ser Leu
            100                 105                 110

Gly Arg Ala Gly Ala Lys Ala Ala Pro Pro Ala Cys Phe Pro Pro Pro
        115                 120                 125

Pro Pro Ala Ala Leu Lys Ala Glu Pro Gly Phe Glu Pro Ala Asp Cys
    130                 135                 140

Lys Arg Ala Asp Asp Ala Pro Ala Met Ala Ala Gly Phe Pro Phe Ala
145                 150                 155                 160

Leu Arg Ala Tyr Leu Gly Tyr Gln Ala Thr Pro Ser Gly Ser Ser Gly
                165                 170                 175

Ser Leu Ser Thr Ser Ser Ser Ser Pro Pro Gly Thr Pro Ser Pro
            180                 185                 190

Ala Asp Ala Lys Ala Ala Pro Ala Ala Cys Phe Ala Gly Pro Pro Ala
        195                 200                 205

Ala Pro Ala Lys Ala Lys Ala Lys Lys Ala Val Asp Lys Leu Ser Asp
    210                 215                 220
```

Glu Tyr Lys Met Arg Arg Glu Arg Asn Asn Ile Ala Val Arg Lys Ser
225                 230                 235                 240

Arg Asp Lys Ala Lys Met Arg Asn Leu Glu Thr Gln His Lys Val Leu
            245                 250                 255

Glu Leu Thr Ala Glu Asn Glu Arg Leu Gln Lys Lys Val Glu Gln Leu
        260                 265                 270

Ser Arg Glu Leu Ser Thr Leu Arg Asn Leu Phe Lys Gln Leu Pro Glu
    275                 280                 285

Pro Leu Leu Ala Ser Ala Gly His Cys
    290                 295

<210> SEQ ID NO 14
<211> LENGTH: 297
<212> TYPE: PRT
<213> ORGANISM: Rattus norvegicus

<400> SEQUENCE: 14

Met His Arg Leu Leu Ala Trp Asp Ala Ala Cys Leu Pro Pro Pro Pro
1               5                   10                  15

Ala Ala Phe Arg Pro Met Glu Val Ala Asn Phe Tyr Tyr Glu Pro Asp
            20                  25                  30

Cys Leu Ala Tyr Gly Ala Lys Ala Ala Arg Ala Ala Pro Arg Ala Pro
        35                  40                  45

Ala Ala Glu Pro Ala Ile Gly Glu His Glu Arg Ala Ile Asp Phe Ser
    50                  55                  60

Pro Tyr Leu Glu Pro Leu Ala Pro Ala Ala Asp Phe Ala Ala Pro
65                  70                  75                  80

Ala Pro Ala His His Asp Phe Leu Ser Asp Leu Phe Ala Asp Asp Tyr
            85                  90                  95

Gly Ala Lys Pro Ser Lys Lys Pro Ala Asp Tyr Gly Tyr Val Ser Leu
        100                 105                 110

Gly Arg Ala Gly Ala Lys Ala Ala Pro Pro Ala Cys Phe Pro Pro Pro
    115                 120                 125

Pro Pro Ala Ala Leu Lys Ala Glu Pro Gly Phe Glu Pro Ala Asp Cys
130                 135                 140

Lys Arg Ala Asp Asp Ala Pro Ala Met Ala Ala Gly Phe Pro Phe Ala
145                 150                 155                 160

Leu Arg Ala Tyr Leu Gly Tyr Gln Ala Thr Pro Ser Gly Ser Ser Gly
            165                 170                 175

Ser Leu Ser Thr Ser Ser Ser Ser Ser Pro Pro Gly Thr Pro Ser Pro
        180                 185                 190

Ala Asp Ala Lys Ala Ala Pro Ala Ala Cys Phe Ala Gly Pro Pro Ala
    195                 200                 205

Ala Pro Ala Lys Ala Lys Ala Lys Lys Ala Val Asp Lys Leu Ser Asp
210                 215                 220

Glu Tyr Lys Met Arg Arg Glu Arg Asn Asn Ile Ala Val Arg Lys Ser
225                 230                 235                 240

Arg Asp Lys Ala Lys Met Arg Asn Leu Glu Thr Gln His Lys Val Leu
            245                 250                 255

Glu Leu Thr Ala Glu Asn Glu Arg Leu Gln Lys Lys Val Glu Gln Leu
        260                 265                 270

Ser Arg Glu Leu Ser Thr Leu Arg Asn Leu Phe Lys Gln Leu Pro Glu
    275                 280                 285

Pro Leu Leu Ala Ser Ala Gly His Cys

<210> SEQ ID NO 15
<211> LENGTH: 297
<212> TYPE: PRT
<213> ORGANISM: Rattus norvegicus

<400> SEQUENCE: 15

```
Met His Arg Leu Leu Ala Trp Asp Ala Ala Cys Leu Pro Pro Pro Pro
1               5                   10                  15

Ala Ala Phe Arg Pro Met Glu Val Ala Asn Phe Tyr Tyr Glu Pro Asp
            20                  25                  30

Cys Leu Ala Tyr Gly Ala Lys Ala Arg Ala Ala Pro Arg Ala Pro
        35                  40                  45

Ala Ala Glu Pro Ala Ile Gly Glu His Glu Arg Ala Ile Asp Phe Ser
    50                  55                  60

Pro Tyr Leu Glu Pro Leu Ala Pro Ala Ala Asp Phe Ala Ala Pro
65                  70                  75                  80

Ala Pro Ala His His Asp Phe Leu Ser Asp Leu Phe Ala Asp Asp Tyr
                85                  90                  95

Gly Ala Lys Pro Ser Lys Lys Pro Asp Asp Tyr Gly Tyr Val Ser Leu
            100                 105                 110

Gly Arg Ala Gly Ala Lys Ala Ala Pro Pro Ala Cys Phe Pro Pro Pro
        115                 120                 125

Pro Pro Ala Ala Leu Lys Ala Glu Pro Gly Phe Glu Pro Ala Asp Cys
130                 135                 140

Lys Arg Ala Asp Asp Ala Pro Ala Met Ala Ala Gly Phe Pro Phe Ala
145                 150                 155                 160

Leu Arg Ala Tyr Leu Gly Tyr Gln Ala Thr Pro Ser Gly Ser Ser Gly
                165                 170                 175

Ser Leu Ser Thr Ser Ser Ser Ser Pro Pro Gly Thr Pro Ser Pro
            180                 185                 190

Ala Asp Ala Lys Ala Ala Pro Ala Ala Cys Phe Ala Gly Pro Pro Ala
        195                 200                 205

Ala Pro Ala Lys Ala Lys Ala Lys Lys Ala Val Asp Lys Leu Ser Asp
210                 215                 220

Glu Tyr Lys Met Arg Arg Glu Arg Asn Asn Ile Ala Val Arg Lys Ser
225                 230                 235                 240

Arg Asp Lys Ala Lys Met Arg Asn Leu Glu Thr Gln His Lys Val Leu
                245                 250                 255

Glu Leu Thr Ala Glu Asn Glu Arg Leu Gln Lys Lys Val Glu Gln Leu
            260                 265                 270

Ser Arg Glu Leu Ser Thr Leu Arg Asn Leu Phe Lys Gln Leu Pro Glu
        275                 280                 285

Pro Leu Leu Ala Ser Ala Gly His Cys
290                 295
```

<210> SEQ ID NO 16
<211> LENGTH: 13
<212> TYPE: PRT
<213> ORGANISM: Homo sapiens
<220> FEATURE:
<221> NAME/KEY: SITE
<222> LOCATION: (7)..(7)
<223> OTHER INFORMATION: The residue at this position is phosphorylated threonine.

<400> SEQUENCE: 16

Lys Ser Lys Ala Lys Lys Thr Val Asp Lys His Ser Asp
1               5                   10

<210> SEQ ID NO 17
<211> LENGTH: 13
<212> TYPE: PRT
<213> ORGANISM: Rattus norvegicus
<220> FEATURE:
<221> NAME/KEY: SITE
<222> LOCATION: (7)..(7)
<223> OTHER INFORMATION: The residue at this position is phosphorylated
      serine.

<400> SEQUENCE: 17

Lys Pro Ser Lys Lys Pro Ser Asp Tyr Gly Tyr Val Ser
1               5                   10

<210> SEQ ID NO 18
<211> LENGTH: 1910
<212> TYPE: DNA
<213> ORGANISM: Homo sapiens
<220> FEATURE:
<221> NAME/KEY: misc_feature
<222> LOCATION: (1415)..(1415)
<223> OTHER INFORMATION: n is a, c, g, or t
<220> FEATURE:
<221> NAME/KEY: misc_feature
<222> LOCATION: (1421)..(1424)
<223> OTHER INFORMATION: n is a, c, g, or t
<220> FEATURE:
<221> NAME/KEY: misc_feature
<222> LOCATION: (1458)..(1458)
<223> OTHER INFORMATION: n is a, c, g, or t

<400> SEQUENCE: 18

| | | | | |
|---|---|---|---|---|
| gtccttcgcg | tcccggcggc | gcggcggagg | ggccggcgtg | acgcagcggt | tgctacgggc | 60 |
| cgcccttata | aataaccggg | ctcaggagaa | actttagcga | gtcagagccg | cgcacgggac | 120 |
| tgggaagggg | acccacccga | gggtccagcc | accagccccc | tcactaatag | cggccacccc | 180 |
| ggcagcggcg | gcagcagcag | cagcgacgca | gcggcgacag | ctcagagcag | ggaggccgcg | 240 |
| cacctgcggg | ccggccggag | cgggcagccc | caggccccct | ccccgggcac | ccgcgttcat | 300 |
| gcaacgcctg | gtggcctggg | acccagcatg | tctccccctg | ccgccgccgc | cgcctgcctt | 360 |
| taaatccatg | gaagtggcca | acttctacta | cgaggcggac | tgcttggctg | ctgcgtacgg | 420 |
| cggcaaggcg | gccccgcgg | cgcccccgc | ggccagaccc | gggccgcgcc | ccccgccgg | 480 |
| cgagctgggc | agcatcggcg | accacgagcg | cgccatcgac | ttcagcccgt | acctggagcc | 540 |
| gctgggcgcg | ccgcaggccc | cggcgcccgc | cacggccacg | gacaccttcg | aggcggctcc | 600 |
| gccccgcgccc | gccccgcgc | ccgcctcctc | cgggcagcac | cacgacttcc | tctccgacct | 660 |
| cttctccgac | gactacgggg | gcaagaactg | caagaagccg | ccgagtacg | gctacgtgag | 720 |
| cctggggcgc | ctgggggctg | ccaagggcgc | gctgcacccc | ggctgcttcg | cgcccctgca | 780 |
| cccaccgccc | ccgccgccgc | cgccgcccgc | cgagctcaag | gcggagccgg | gcttcgagcc | 840 |
| cgcggactgc | aagcggaagg | aggaggccgg | ggcgccgggc | ggcggcgcag | gcatggcggc | 900 |
| gggcttcccg | tacgcgctgc | gcgcttacct | cggctaccag | gcggtgccga | gcggcagcag | 960 |
| cgggagcctc | tccacgtcct | cctcgtccag | cccgcccggc | acgccgagcc | ccgctgacgc | 1020 |
| caaggccccc | ccgaccgcct | gctacgcggg | ggccggccg | gcgccctcgc | aggtcaagag | 1080 |
| caaggccaag | aagaccgtgg | acaagcacag | cgacgagtac | aagatccggc | gcgagcgcaa | 1140 |
| caacatcgcc | gtgcgcaaga | gccgcgacaa | ggccaagatg | cgcaacctgg | agacgcagca | 1200 |

-continued

```
caaggtcctg gagctcacgg ccgagaacga gcggctgcag aagaaggtgg agcagctgtc    1260
gcgcgagctc agcaccctgc ggaacttgtt caagcagctg cccgagcccc tgctcgcctc    1320
ctccggccac tgctagcgcg gccccgcgg cgtccccctg gggccggccg gggctgagac     1380
tccggggagc gcccgcgccc gcgccctcgc ccccnccccc nnnnccgcaa aactttggca    1440
ctggggcact tggcagcngg ggagcccgtc ggtaatttta atattttatt atatatatat    1500
atctatattt tgccaaccaa ccgtacatgc agatggctcc cgcccgtggt gtataaagaa    1560
gaaatgtcta tgtgtacaga tgaatgataa actctctgct ctccctctgc ccctctccag    1620
gcccggcggg cggggccggt tcgaagttg atgcaatcgg tttaaacatg gctgaacgcg     1680
tgtgtacacg ggactgacgc aacccacgtg taactgtcag ccgggccctg agtaatcgct    1740
taaagatgtt ctagggcttg ttgctgttga tgttttgttt tgttttgttt tttggtctttt   1800 ttttgtatta taaaaaataa tctatttcta tgagaaaaga ggcgtctgta tattttggga    1860
atcttttccg tttcaagcaa ttaagaacac ttttaataaa cttttttttg               1910
```

<210> SEQ ID NO 19
<211> LENGTH: 345
<212> TYPE: PRT
<213> ORGANISM: Homo sapiens

<400> SEQUENCE: 19

```
Met Gln Arg Leu Val Ala Trp Asp Pro Ala Cys Leu Pro Leu Pro Pro
1               5                   10                  15

Pro Pro Pro Ala Phe Lys Ser Met Glu Val Ala Asn Phe Tyr Tyr Glu
            20                  25                  30

Ala Asp Cys Leu Ala Ala Ala Tyr Gly Gly Lys Ala Ala Pro Ala Ala
        35                  40                  45

Pro Pro Ala Ala Arg Pro Gly Pro Arg Pro Pro Ala Gly Glu Leu Gly
    50                  55                  60

Ser Ile Gly Asp His Glu Arg Ala Ile Asp Phe Ser Pro Tyr Leu Glu
65                  70                  75                  80

Pro Leu Gly Ala Pro Gln Ala Pro Ala Pro Ala Thr Ala Thr Asp Thr
                85                  90                  95

Phe Glu Ala Ala Pro Pro Ala Pro Ala Pro Ala Pro Ala Ser Ser Gly
            100                 105                 110

Gln His His Asp Phe Leu Ser Asp Leu Phe Ser Asp Asp Tyr Gly Gly
        115                 120                 125

Lys Asn Cys Lys Lys Pro Ala Glu Tyr Gly Tyr Val Ser Leu Gly Arg
    130                 135                 140

Leu Gly Ala Ala Lys Gly Ala Leu His Pro Gly Cys Phe Ala Pro Leu
145                 150                 155                 160

His Pro Pro Pro Pro Pro Pro Pro Ala Glu Leu Lys Ala Glu
                165                 170                 175

Pro Gly Phe Glu Pro Ala Asp Cys Lys Arg Lys Glu Glu Ala Gly Ala
            180                 185                 190

Pro Gly Gly Gly Ala Gly Met Ala Ala Gly Phe Pro Tyr Ala Leu Arg
        195                 200                 205

Ala Tyr Leu Gly Tyr Gln Ala Val Pro Ser Gly Ser Ser Gly Ser Leu
    210                 215                 220

Ser Thr Ser Ser Ser Ser Ser Pro Pro Gly Thr Pro Ser Pro Ala Asp
225                 230                 235                 240

Ala Lys Ala Pro Pro Thr Ala Cys Tyr Ala Gly Ala Gly Pro Ala Pro
```

-continued

```
                245                 250                 255
Ser Gln Val Lys Ser Lys Ala Lys Thr Val Asp Lys His Ser Asp
            260                 265                 270

Glu Tyr Lys Ile Arg Arg Glu Arg Asn Asn Ile Ala Val Arg Lys Ser
            275                 280                 285

Arg Asp Lys Ala Lys Met Arg Asn Leu Glu Thr Gln His Lys Val Leu
            290                 295                 300

Glu Leu Thr Ala Glu Asn Glu Arg Leu Gln Lys Lys Val Glu Gln Leu
305                 310                 315                 320

Ser Arg Glu Leu Ser Thr Leu Arg Asn Leu Phe Lys Gln Leu Pro Glu
            325                 330                 335

Pro Leu Leu Ala Ser Ser Gly His Cys
            340                 345

<210> SEQ ID NO 20
<211> LENGTH: 345
<212> TYPE: PRT
<213> ORGANISM: Homo sapiens

<400> SEQUENCE: 20

Met Gln Arg Leu Val Ala Trp Asp Pro Ala Cys Leu Pro Leu Pro Pro
1               5                   10                  15

Pro Pro Pro Ala Phe Lys Ser Met Glu Val Ala Asn Phe Tyr Tyr Glu
            20                  25                  30

Ala Asp Cys Leu Ala Ala Ala Tyr Gly Gly Lys Ala Ala Pro Ala Ala
        35                  40                  45

Pro Pro Ala Ala Arg Pro Gly Pro Arg Pro Pro Ala Gly Glu Leu Gly
    50                  55                  60

Ser Ile Gly Asp His Glu Arg Ala Ile Asp Phe Ser Pro Tyr Leu Glu
65              70                  75                  80

Pro Leu Gly Ala Pro Gln Ala Pro Ala Pro Ala Thr Ala Thr Asp Thr
            85                  90                  95

Phe Glu Ala Ala Pro Pro Ala Pro Ala Pro Ala Pro Ala Ser Ser Gly
            100                 105                 110

Gln His His Asp Phe Leu Ser Asp Leu Phe Ser Asp Asp Tyr Gly Gly
        115                 120                 125

Lys Asn Cys Lys Lys Pro Ala Glu Tyr Gly Tyr Val Ser Leu Gly Arg
    130                 135                 140

Leu Gly Ala Ala Lys Gly Ala Leu His Pro Gly Cys Phe Ala Pro Leu
145                 150                 155                 160

His Pro Pro Pro Pro Pro Pro Pro Ala Glu Leu Lys Ala Glu
            165                 170                 175

Pro Gly Phe Glu Pro Ala Asp Cys Lys Arg Lys Glu Glu Ala Gly Ala
            180                 185                 190

Pro Gly Gly Gly Ala Gly Met Ala Ala Gly Phe Pro Tyr Ala Leu Arg
            195                 200                 205

Ala Tyr Leu Gly Tyr Gln Ala Val Pro Ser Gly Ser Ser Gly Ser Leu
        210                 215                 220

Ser Thr Ser Ser Ser Ser Ser Pro Pro Gly Thr Pro Ser Pro Ala Asp
225                 230                 235                 240

Ala Lys Ala Pro Pro Thr Ala Cys Tyr Ala Gly Ala Gly Pro Ala Pro
            245                 250                 255

Ser Gln Val Lys Ser Lys Ala Lys Lys Ala Val Asp Lys His Ser Asp
            260                 265                 270
```

```
Glu Tyr Lys Ile Arg Arg Glu Arg Asn Asn Ile Ala Val Arg Lys Ser
            275                 280                 285
Arg Asp Lys Ala Lys Met Arg Asn Leu Glu Thr Gln His Lys Val Leu
        290                 295                 300
Glu Leu Thr Ala Glu Asn Glu Arg Leu Gln Lys Val Glu Gln Leu
305                 310                 315                 320
Ser Arg Glu Leu Ser Thr Leu Arg Asn Leu Phe Lys Gln Leu Pro Glu
                325                 330                 335
Pro Leu Leu Ala Ser Ser Gly His Cys
            340                 345

<210> SEQ ID NO 21
<211> LENGTH: 345
<212> TYPE: PRT
<213> ORGANISM: Homo sapiens

<400> SEQUENCE: 21

Met Gln Arg Leu Val Ala Trp Asp Pro Ala Cys Leu Pro Leu Pro Pro
1               5                   10                  15
Pro Pro Pro Ala Phe Lys Ser Met Glu Val Ala Asn Phe Tyr Tyr Glu
            20                  25                  30
Ala Asp Cys Leu Ala Ala Ala Tyr Gly Gly Lys Ala Ala Pro Ala Ala
        35                  40                  45
Pro Pro Ala Ala Arg Pro Gly Pro Arg Pro Pro Ala Gly Glu Leu Gly
    50                  55                  60
Ser Ile Gly Asp His Glu Arg Ala Ile Asp Phe Ser Pro Tyr Leu Glu
65                  70                  75                  80
Pro Leu Gly Ala Pro Gln Ala Pro Ala Pro Ala Thr Ala Thr Asp Thr
                85                  90                  95
Phe Glu Ala Ala Pro Pro Ala Pro Ala Pro Ala Ser Ser Gly
            100                 105                 110
Gln His His Asp Phe Leu Ser Asp Leu Phe Ser Asp Tyr Gly Gly
        115                 120                 125
Lys Asn Cys Lys Lys Pro Ala Glu Tyr Gly Tyr Val Ser Leu Gly Arg
    130                 135                 140
Leu Gly Ala Ala Lys Gly Ala Leu His Pro Gly Cys Phe Ala Pro Leu
145                 150                 155                 160
His Pro Pro Pro Pro Pro Pro Pro Ala Glu Leu Lys Ala Glu
                165                 170                 175
Pro Gly Phe Glu Pro Ala Asp Cys Lys Arg Lys Glu Glu Ala Gly Ala
            180                 185                 190
Pro Gly Gly Gly Ala Gly Met Ala Ala Gly Phe Pro Tyr Ala Leu Arg
        195                 200                 205
Ala Tyr Leu Gly Tyr Gln Ala Val Pro Ser Gly Ser Ser Gly Ser Leu
    210                 215                 220
Ser Thr Ser Ser Ser Ser Ser Pro Pro Gly Thr Pro Ser Pro Ala Asp
225                 230                 235                 240
Ala Lys Ala Pro Pro Thr Ala Cys Tyr Ala Gly Ala Gly Pro Ala Pro
                245                 250                 255
Ser Gln Val Lys Ser Lys Ala Lys Lys Glu Val Asp Lys His Ser Asp
            260                 265                 270
Glu Tyr Lys Ile Arg Arg Glu Arg Asn Asn Ile Ala Val Arg Lys Ser
        275                 280                 285
Arg Asp Lys Ala Lys Met Arg Asn Leu Glu Thr Gln His Lys Val Leu
    290                 295                 300
```

-continued

```
Glu Leu Thr Ala Glu Asn Glu Arg Leu Gln Lys Lys Val Glu Gln Leu
305                 310                 315                 320

Ser Arg Glu Leu Ser Thr Leu Arg Asn Leu Phe Lys Gln Leu Pro Glu
            325                 330                 335

Pro Leu Leu Ala Ser Ser Gly His Cys
        340                 345
```

<210> SEQ ID NO 22
<211> LENGTH: 1038
<212> TYPE: DNA
<213> ORGANISM: Homo sapiens

<400> SEQUENCE: 22

| | | |
|---|---|---|
| atgcaacgcc tggtggcctg ggacccagca tgtctccccc tgccgccgcc gccgcctgcc | 60 |
| tttaaatcca tggaagtggc caacttctac tacgaggcgg actgcttggc tgctgcgtac | 120 |
| ggcggcaagg cggcccccgc ggcgcccccc gcggccagac ccgggccgcg ccccccccgcc | 180 |
| ggcgagctgg gcagcatcgg cgaccacgag cgcgccatcg acttcagccc gtacctggag | 240 |
| ccgctgggcg cgccgcaggc cccggcgccc gccacggcca cggacacctt cgaggcggct | 300 |
| ccgcccgcgc cgccccccgc gcccgcctcc tccgggcagc accacgactt cctctccgac | 360 |
| ctcttctccg acgactacgg gggcaagaac tgcaagaagc cggccgagta cggctacgtg | 420 |
| agcctggggc gcctgggggc tgccaagggc gcgctgcacc ccggctgctt cgcgcccctg | 480 |
| cacccaccgc cccgccgcc gccgccgccc gccgagctca aggcggagcc gggcttcgag | 540 |
| cccgcggact gcaagcggaa ggaggaggcc ggggcgccgg cggcggcgc aggcatggcg | 600 |
| gcgggcttcc cgtacgcgct cgcgcttac ctcggctacc aggcggtgcc gagcggcagc | 660 |
| agcgggagcc tctccacgtc ctcctcgtcc agcccgcccg gcacgccgag cccgctgac | 720 |
| gccaaggccc ccccgaccgc ctgctacgcg ggggccgggc cggcgccctc gcaggtcaag | 780 |
| agcaaggcca agaagaccgt ggacaagcac agcgacgagt acaagatccg cgcgagcgc | 840 |
| aacaacatcg ccgtgcgcaa gagccgcgac aaggccaaga tgcgcaacct ggagacgcag | 900 |
| cacaaggtcc tggagctcac ggccgagaac gagcggctgc agaagaaggt ggagcagctg | 960 |
| tcgcgcgagc tcagcaccct gcggaacttg ttcaagcagc tgcccgagcc cctgctcgcc | 1020 |
| tcctccggcc actgctag | 1038 |

<210> SEQ ID NO 23
<211> LENGTH: 345
<212> TYPE: PRT
<213> ORGANISM: Homo sapiens

<400> SEQUENCE: 23

```
Met Gln Arg Leu Val Ala Trp Asp Pro Ala Cys Leu Pro Leu Pro Pro
1               5                   10                  15

Pro Pro Pro Ala Phe Lys Ser Met Glu Val Ala Asn Phe Tyr Tyr Glu
            20                  25                  30

Ala Asp Cys Leu Ala Ala Ala Tyr Gly Gly Lys Ala Ala Pro Ala Ala
        35                  40                  45

Pro Pro Ala Ala Arg Pro Gly Pro Arg Pro Ala Gly Glu Leu Gly
    50                  55                  60

Ser Ile Gly Asp His Glu Arg Ala Ile Asp Phe Ser Pro Tyr Leu Glu
65                  70                  75                  80

Pro Leu Gly Ala Pro Gln Ala Pro Ala Pro Ala Thr Ala Thr Asp Thr
                85                  90                  95
```

```
Phe Glu Ala Ala Pro Pro Ala Pro Ala Pro Ala Ser Ser Gly
            100                 105                 110

Gln His His Asp Phe Leu Ser Asp Leu Phe Ser Asp Asp Tyr Gly Gly
            115                 120                 125

Lys Asn Cys Lys Lys Pro Ala Glu Tyr Gly Tyr Val Ser Leu Gly Arg
130                 135                 140

Leu Gly Ala Ala Lys Gly Ala Leu His Pro Gly Cys Phe Ala Pro Leu
145                 150                 155                 160

His Pro Pro Pro Pro Pro Pro Pro Ala Glu Leu Lys Ala Glu
            165                 170                 175

Pro Gly Phe Glu Pro Ala Asp Cys Lys Arg Lys Glu Glu Ala Gly Ala
            180                 185                 190

Pro Gly Gly Gly Ala Gly Met Ala Ala Gly Phe Pro Tyr Ala Leu Arg
            195                 200                 205

Ala Tyr Leu Gly Tyr Gln Ala Val Pro Ser Gly Ser Ser Gly Ser Leu
            210                 215                 220

Ser Thr Ser Ser Ser Ser Ser Pro Pro Gly Thr Pro Ser Pro Ala Asp
225                 230                 235                 240

Ala Lys Ala Pro Pro Thr Ala Cys Tyr Ala Gly Ala Gly Pro Ala Pro
            245                 250                 255

Ser Gln Val Lys Ser Lys Ala Lys Lys Thr Val Asp Lys His Ser Asp
            260                 265                 270

Glu Tyr Lys Ile Arg Arg Glu Arg Asn Asn Ile Ala Val Arg Lys Ser
            275                 280                 285

Arg Asp Lys Ala Lys Met Arg Asn Leu Glu Thr Gln His Lys Val Leu
            290                 295                 300

Glu Leu Thr Ala Glu Asn Glu Arg Leu Gln Lys Lys Val Glu Gln Leu
305                 310                 315                 320

Ser Arg Glu Leu Ser Thr Leu Arg Asn Leu Phe Lys Gln Leu Pro Glu
            325                 330                 335

Pro Leu Leu Ala Ser Ser Gly His Cys
            340                 345

<210> SEQ ID NO 24
<211> LENGTH: 345
<212> TYPE: PRT
<213> ORGANISM: Homo sapiens

<400> SEQUENCE: 24

Met Gln Arg Leu Val Ala Trp Asp Pro Ala Cys Leu Pro Leu Pro Pro
1               5                   10                  15

Pro Pro Pro Ala Phe Lys Ser Met Glu Val Ala Asn Phe Tyr Tyr Glu
            20                  25                  30

Ala Asp Cys Leu Ala Ala Ala Tyr Gly Gly Lys Ala Ala Pro Ala Ala
            35                  40                  45

Pro Pro Ala Ala Arg Pro Gly Pro Arg Pro Ala Gly Glu Leu Gly
50                  55                  60

Ser Ile Gly Asp His Glu Arg Ala Ile Asp Phe Ser Pro Tyr Leu Glu
65                  70                  75                  80

Pro Leu Gly Ala Pro Gln Ala Pro Ala Pro Ala Thr Ala Thr Asp Thr
            85                  90                  95

Phe Glu Ala Ala Pro Pro Ala Pro Ala Pro Ala Pro Ala Ser Ser Gly
            100                 105                 110

Gln His His Asp Phe Leu Ser Asp Leu Phe Ser Asp Asp Tyr Gly Gly
            115                 120                 125
```

-continued

```
                115                 120                 125
Lys Asn Cys Lys Lys Pro Ala Glu Tyr Gly Tyr Val Ser Leu Gly Arg
        130                 135                 140

Leu Gly Ala Ala Lys Gly Ala Leu His Pro Gly Cys Phe Ala Pro Leu
145                 150                 155                 160

His Pro Pro Pro Pro Pro Pro Ala Glu Leu Lys Ala Glu
                165                 170                 175

Pro Gly Phe Glu Pro Ala Asp Cys Lys Arg Lys Glu Glu Ala Gly Ala
                180                 185                 190

Pro Gly Gly Gly Ala Gly Met Ala Ala Gly Phe Pro Tyr Ala Leu Arg
                195                 200                 205

Ala Tyr Leu Gly Tyr Gln Ala Val Pro Ser Gly Ser Ser Gly Ser Leu
        210                 215                 220

Ser Thr Ser Ser Ser Ser Pro Pro Gly Thr Pro Ser Pro Ala Asp
225                 230                 235                 240

Ala Lys Ala Pro Pro Thr Ala Cys Tyr Ala Gly Ala Gly Pro Ala Pro
                245                 250                 255

Ser Gln Val Lys Ser Lys Ala Lys Lys Ala Val Asp Lys His Ser Asp
                260                 265                 270

Glu Tyr Lys Ile Arg Arg Glu Arg Asn Asn Ile Ala Val Arg Lys Ser
                275                 280                 285

Arg Asp Lys Ala Lys Met Arg Asn Leu Glu Thr Gln His Lys Val Leu
        290                 295                 300

Glu Leu Thr Ala Glu Asn Glu Arg Leu Gln Lys Lys Val Glu Gln Leu
305                 310                 315                 320

Ser Arg Glu Leu Ser Thr Leu Arg Asn Leu Phe Lys Gln Leu Pro Glu
                325                 330                 335

Pro Leu Leu Ala Ser Ser Gly His Cys
                340                 345

<210> SEQ ID NO 25
<211> LENGTH: 345
<212> TYPE: PRT
<213> ORGANISM: Homo sapiens

<400> SEQUENCE: 25

Met Gln Arg Leu Val Ala Trp Asp Pro Ala Cys Leu Pro Leu Pro Pro
1               5                   10                  15

Pro Pro Pro Ala Phe Lys Ser Met Glu Val Ala Asn Phe Tyr Tyr Glu
                20                  25                  30

Ala Asp Cys Leu Ala Ala Ala Tyr Gly Gly Lys Ala Ala Pro Ala Ala
            35                  40                  45

Pro Pro Ala Ala Arg Pro Gly Pro Arg Pro Pro Ala Gly Glu Leu Gly
    50                  55                  60

Ser Ile Gly Asp His Glu Arg Ala Ile Asp Phe Ser Pro Tyr Leu Glu
65                  70                  75                  80

Pro Leu Gly Ala Pro Gln Ala Pro Ala Pro Ala Thr Ala Thr Asp Thr
                85                  90                  95

Phe Glu Ala Ala Pro Pro Ala Pro Ala Pro Ala Pro Ala Ser Ser Gly
                100                 105                 110

Gln His His Asp Phe Leu Ser Asp Leu Phe Ser Asp Asp Tyr Gly Gly
            115                 120                 125

Lys Asn Cys Lys Lys Pro Ala Glu Tyr Gly Tyr Val Ser Leu Gly Arg
        130                 135                 140
```

```
Leu Gly Ala Ala Lys Gly Ala Leu His Pro Gly Cys Phe Ala Pro Leu
145                 150                 155                 160

His Pro Pro Pro Pro Pro Pro Pro Ala Glu Leu Lys Ala Glu
            165             170             175

Pro Gly Phe Glu Pro Ala Asp Cys Lys Arg Lys Glu Glu Ala Gly Ala
            180             185             190

Pro Gly Gly Gly Ala Gly Met Ala Ala Gly Phe Pro Tyr Ala Leu Arg
        195             200             205

Ala Tyr Leu Gly Tyr Gln Ala Val Pro Ser Gly Ser Ser Gly Ser Leu
    210             215             220

Ser Thr Ser Ser Ser Ser Ser Pro Pro Gly Thr Pro Ser Pro Ala Asp
225             230             235                 240

Ala Lys Ala Pro Pro Thr Ala Cys Tyr Ala Gly Ala Gly Pro Ala Pro
            245             250             255

Ser Gln Val Lys Ser Lys Ala Lys Lys Glu Val Asp Lys His Ser Asp
            260             265             270

Glu Tyr Lys Ile Arg Arg Glu Arg Asn Asn Ile Ala Val Arg Lys Ser
        275             280             285

Arg Asp Lys Ala Lys Met Arg Asn Leu Glu Thr Gln His Lys Val Leu
        290             295             300

Glu Leu Thr Ala Glu Asn Glu Arg Leu Gln Lys Lys Val Glu Gln Leu
305             310             315             320

Ser Arg Glu Leu Ser Thr Leu Arg Asn Leu Phe Lys Gln Leu Pro Glu
            325             330             335

Pro Leu Leu Ala Ser Ser Gly His Cys
            340             345
```

TREATMENT OF DISEASE BY INDUCING CELL APOPTOSIS

The present application is a U.S. national entry of International Appln. No. PCT/US01/51123, filed Oct. 26, 2001, which claims priority benefit to U.S. Provisional Patent Appln. Ser. No. 60/244,018 filed Oct. 27, 2000.

This invention was made with government support under DK 38652 and DK 46971, awarded by the National Institutes of Health. The government has certain rights in this invention.

FIELD OF THE INVENTION

The present invention relates generally to the treatment and prevention of diseases characterized by excess cell proliferation and/or activation. In particular, the present invention provides compositions and methods to suppress the activation and/or proliferation of various cells. In preferred embodiments, the present invention provides compositions and methods to suppress the activation and/or proliferation of mesenchymally derived cells (including, but not limited to hepatic stellate cells), as well as cells with abnormal growth characteristics. In particularly preferred embodiments, the present invention provides compositions and methods to inhibit or eliminate fibrosis. In alternative preferred embodiments, the present invention provides compositions and methods to induce fibrosis.

BACKGROUND OF THE INVENTION

Abnormal cell proliferation is a hallmark of various pathological conditions. In particular, uncontrolled cell growth is associated with diseases such as fibrosis (e.g., hepatic fibrosis), and various other diseases and conditions associated with abnormal cell proliferation.

For example, chronic hepatitis is characterized as an inflammatory liver disease continuing for at least six months without improvement. Chronic hepatitis C represents one form of chronic hepatitis. Left unchecked, chronic hepatitis C can progress to cirrhosis and extensive necrosis of the liver. Although chronic hepatitis C is often associated with deposition of collagen type I leading to hepatic fibrosis, the mechanisms of fibrogenesis remain unknown. Indeed, there is no established treatment for hepatic fibrogenesis related to the over-production of collagen type I (See, e.g., Maher and McGuire, J. Clin. Invest. 86:1641-48 (1990); Chojkier *Pathogenesis of hepatic fibrosis. In Extracellular Matrix*, Marcel Dekker Inc., New York, N.Y., pp. 541-57 [1993]). However, it is known that ribosomal protein S-6 kinases (RSKs) are critical for survival of cells such as the hepatic stellate cells that overproduce the fibrous tissue that results in cirrhosis. Nonetheless, despite the tremendous research effort and funding dedicated fibrotic diseases (e.g., hepatic fibrosis), there remains a need in the art for compositions and methods that are effective in suppressing the activation and/or proliferation of abnormal cells.

SUMMARY OF THE INVENTION

The present invention relates generally to the treatment and prevention of diseases characterized by excess cell proliferation and/or activation. In particular, the present invention provides compositions and methods to suppress the activation and/or proliferation of various cells, including but not limited to mesenchymal cells. In preferred embodiments, the present invention provides compositions and methods to suppress the activation and/or proliferation of mesenchymally derived cells (including, but not limited to hepatic stellate cells), as well as cells with abnormal growth characteristics. In particularly preferred embodiments, the present invention provides compositions and methods to inhibit or eliminate fibrosis. In alternative preferred embodiments, the present invention provides compositions and methods to induce fibrosis.

The present invention also provides methods and compositions suitable for the suppression of cell activation and/or proliferation. In some preferred embodiments, the present invention also provides methods and compositions suitable for the suppression of hepatic stellate cell activation and/or proliferation. In particularly preferred embodiments, the present invention provides methods for administering C/EBPβ with a mutation of $Thr^{217}$ to Ala. In other embodiments, the endogenous phosphopeptidases associate with caspases 1 and 8 and result in the inhibition of their activation. In alternative embodiments, the mutant $Ala^{217}$ peptides compete with the wild-type peptides, allowing the activation of caspases, resulting in apoptosis.

The modified C/EBPβ peptides of the present invention find use with various tissues and cells. It is contemplated that any suitable route of administration will find use with the present invention. Thus, in some embodiments, the peptides are administered using genetic therapy methods, selective peptide delivery systems, or any other suitable method for delivery to the site of interest. In particularly preferred embodiments, the peptides are delivered to hepatic stellate cells. In alternative preferred embodiments, the peptides are administered parenterally while in still further embodiments, the peptides are administered orally or topically.

In some embodiments, the composition(s) of the present invention is/are administered to the subject in a single dose, while in other embodiments, the composition is administered to the subject in multiple doses. In preferred embodiments, the administering is selected from the group consisting of subcutaneous injection, oral administration, intravenous administration, intraarterial administration, intraperitoneal administration, rectal administration, vaginal administration, topical administration, intramuscular administration, intranasal administration, intrapulmonary administration (e.g., inhalation, insufflation, etc.), intratracheal administration, epidermal administration, transdermal administration, subconjunctival administration, intraocular administration, periocular administration, retrobulbar administration, subretinal administration, suprachoroidal administration, intramedullar administration, intracranial administration, intraventricular administration, and intrathecal administration. In alternative embodiments, the administering is administration from a source selected from the group consisting of mechanical reservoirs, devices, implants, and patches. In still further embodiments, the composition is in a form selected from the group consisting of pills, capsules, liquids, gels, powders, suppositories, suspensions, creams, jellies, aerosol sprays, and dietary supplements. Additionally, the peptides may be administered as an ointment, lotion or gel (i.e., for the treatment of skin and mucosal areas). In some embodiments, it is expected that cells in several tissues will contain an expression vector and express the gene of interest (i.e., such that the peptide(s) of interest are expressed in the tissue(s)).

In alternative embodiments, once the peptides are incorporated into cells, the peptides compete with endogenous C/EBP wild-type protein. In still further embodiments, the presence of mutant C/EBPβ peptide(s) results in the induction of stellate cells apoptosis. In other embodiments, the activation and proliferation of hepatic stellate cells is prevented. In particularly preferred embodiments, this prevention of activation and proliferation of hepatic stellate cells results in decreased or complete cessation of fibrous tissue production in the liver. In some embodiments, the methods are used to treat subjects suffering from or suspected of suffering from chronic liver disease (e.g., including but not limited to hepatitis C, hepatitis B, alcoholism, toxic and genetic liver diseases). Furthermore, it is contemplated that the methods of the present invention will find use in the prevention of liver fibrosis associated with liver rejection following liver transplantation.

The present invention provides modified C/EBPβ peptides from various species. In some preferred embodiments, the murine C/EBPβ peptide comprises a mutation at amino acid 217. In some embodiments, the threonine present in wild-type murine C/EBPβ at position 217 (SEQ ID NO:2) is replaced with alanine (SEQ ID NO:3), while in other embodiments, it is replaced with glutamic acid (SEQ ID NO:4). In alternative preferred embodiments, the rat C/EBPβ peptide comprises a mutation at amino acid 105. In some embodiments, the serine at position 105 of the wild-type rat C/EBPβ (SEQ ID NO:10) is replaced with alanine (SEQ ID NO:11), while in other embodiments, it is replaced with aspartic acid (SEQ ID NO:12). In still further preferred embodiments, the human C/EBPβ comprises a mutation at amino acid 266. In some embodiments, the threonine at position 266 of the wild-type human C/EBPβ (SEQ ID NO:6, SEQ ID NO:9, SEQ ID NO:19, and SEQ ID NO:23) is replaced with alanine (SEQ ID NO:7, SEQ ID NO:10, SEQ ID NO:20, and SEQ ID NO:24), while in other embodiments, it is replaced with glutamic acid (SEQ ID NO:8, SEQ ID NO:11, SEQ ID NO:21, and SEQ ID NO:25). Other mutations in C/EBPβ peptides from various species are contemplated by the present invention. The only requirement of these modified C/EBPβ peptides is that they are capable of inducing or prevent apoptosis in a cell or tissue of interest. In particularly preferred embodiments, the induction of apoptosis results in the reduction (i.e., diminution), elimination, and/or prevention of fibrosis in a cell or tissue of interest. In alternative preferred embodiments, the modified C/EBPβ peptides induce fibrosis (e.g., to promote wound healing).

In some preferred embodiments, the present invention provides modified CCAAT/Enhancer binding proteins capable of inducing apoptosis. In some preferred embodiments, the modified CCAAT/Enhancer binding protein is selected from the group consisting of modified human CCAAT/Enhancer binding proteins, and modified mouse CCAAT/Enhancer binding proteins. In further preferred embodiments, the protein is encoded by an amino acid sequence selected from the group consisting of SEQ ID NO:3, SEQ ID NO:4, SEQ ID NO:7, SEQ ID NO:8, SEQ ID NO: 10, SEQ ID NO:11, SEQ ID NO:20, SEQ ID NO:21, SEQ ID NO:24, and SEQ ID NO:25.

The present invention also provides methods for inducing apoptosis comprising the steps of administering at least one modified CCAAT/Enhancer binding protein to at least one cell. In some preferred embodiments, the cell is a mesenchymal cell. In further embodiments, the cell is selected from the group consisting of hepatic cells, lung cells, kidney cells, skin cells, muscle cells, heart cells, glial cells, ocular cells, and vascular cells. In some particularly preferred embodiments, the administration prevents fibrosis. In alternative preferred embodiments, the administration ameliorates fibrosis.

The present invention also provides methods for inducing apoptosis comprising administering the CCAAT/Enhancer binding protein to a subject under conditions such that the endogenous phosphopeptides of the subject inhibit the activation of at least one caspase of the subject. In some preferred embodiments, the administration results in the apoptosis of selected cells within the subject.

The present invention further provides methods for inducing apoptosis comprising administering at least a portion of a modified CCAAT/Enhancer binding protein to at least one cell, wherein the modified CCAAT/Enhancer binding protein is selected from the group consisting of modified murine, modified rat, and modified human CCAAT/Enhancer binding proteins. In some preferred embodiments, the modified murine CCAAT/Enhancer binding protein comprises a mutation at amino acid position 217, wherein the amino acid at position 217 is selected from the group consisting of alanine and glutamic acid. In other preferred embodiments, the modified murine CCAAT/Enhancer binding protein comprises an amino acid sequence selected from the group consisting of SEQ ID NO:3 and SEQ ID NO:4. In additional embodiments, the modified human CCAAT/Enhancer binding protein comprises a mutation at amino acid position 266, wherein the amino acid at position 266 is selected from the group consisting of alanine and glutamic acid. In further embodiments, the modified human CCAAT/Enhancer binding protein comprises an amino acid sequence selected from the group consisting of SEQ ID NO:7, SEQ ID NO:8, SEQ ID NO:10, and SEQ ID NO:11. In yet additional embodiments, the modified rat CCAAT/Enhancer binding protein comprises a mutation at amino acid position 105, wherein the amino acid at position 105 is selected from the group consisting of alanine and aspartic acid. In further embodiments, the modified rat CCAAT/Enhancer binding protein comprises an amino acid sequence selected from the group consisting of SEQ ID NO:14 and SEQ ID NO:15. In some preferred embodiments, apoptosis is induced in at least one cell selected from the group consisting of hepatic cells, heart cells, lung cells, kidney cells, ocular cells, neural cells, muscle cells, epithelial cells, endothelial cells, mesenchymal cells, and skin cells. In some preferred embodiments, the cell(s) is/are within a subject. In further embodiments, the subject is a mammal. In some particularly preferred embodiments, the mammal is a human. In additional embodiments, the human is suffering from a fibrosis-related disease, wherein the fibrosis-related disease is selected from the group consisting of hepatic disease, brain damage, myocardial infarction, arteriosclerosis, ocular fibrosis, fibrotic skin conditions, and fibrotic pulmonary disease.

The present invention also provides methods for inducing fibrosis comprising the administration of at least a portion of a modified CCAAT/Enhancer binding protein to at least one tissue, wherein the modified CCAAT/Enhancer binding protein is selected from the group consisting of modified murine, modified rat and modified human CCAAT/Enhancer binding proteins. In some preferred embodiments, prior to the administration of CCAAT/Enhancer binding protein, at least one tissue exhibits impaired wound healing. In some embodiments, the induction of fibrosis provides improved wound healing in at least one tissue. In some particularly preferred embodiments, the modified CCAAT/Enhancer binding protein is the amino acid sequence set forth in SEQ ID NO:4.

Definitions

To facilitate understanding of the invention that follows, a number of terms and phrases are defined below.

As used herein, the term "mesenchyme" refers to the embryonic tissue that is the origin of connective tissue, as well as muscle, blood cells and vessels, epithelium, and some glands.

As used herein, the term "gene" means the deoxyribonucleotide sequences comprising the coding region of a structural gene and including sequences located adjacent to the coding region on both the 5' and 3' ends for a distance of several kb on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. A genomic form or clone of a gene contains coding sequences, termed exons, alternating with non-coding sequences termed "introns" or "intervening regions" or "intervening sequences." Introns are segments of a gene which are transcribed into heterogenous nuclear RNA (hnRNA); introns may contain regulatory elements such as enhancers. Introns are removed or "spliced out" from the nuclear or primary transcript; introns therefore are absent in the messenger RNA (mRNA) transcript. In addition to containing introns, genomic forms of a gene may also include sequences located on both the 5' and 3' end of the sequences which are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers which control or influence the transcription of the gene. The 3' flanking region may contain sequences which direct the termination of transcription, posttranscriptional cleavage and polyadenylation.

As used herein the term "coding region" when used in reference to a structural gene refers to the nucleotide sequences which encode the amino acids found in the nascent polypeptide as a result of translation of an mRNA molecule. The coding region is bounded, in eukaryotes, on the 5' side by the nucleotide triplet "ATG" which encodes the initiator methionine and on the 3' side by one of the three triplets which specify stop codons (i.e., TAA, TAG, TGA).

As used herein, the term "structural gene" refers to a DNA sequence coding for RNA or a protein. In contrast, "regulatory genes" are structural genes which encode products (e.g., transcription factors) which control the expression of other genes.

As used herein, the term "regulatory element" refers to a genetic element which controls some aspect of the expression of nucleic acid sequences. For example, a promoter is a regulatory element which facilitates the initiation of transcription of an operably linked coding region. Other regulatory elements are splicing signals, polyadenylation signals, termination signals, enhancer elements, etc. Promoters and enhancers consist of short arrays of DNA sequences that interact specifically with cellular proteins involved in transcription (Maniatis et al., Science 236:1237 [1987]). Promoter and enhancer elements have been isolated from a variety of eukaryotic sources including genes in yeast, insect and mammalian cells and viruses (analogous control elements [i.e., promoters], are also found in prokaryotes). The selection of a particular promoter and enhancer depends on what cell type is to be used to express the protein of interest. Some eukaryotic promoters and enhancers have a broad host range while others are functional in a limited subset of cell types (for review see Voss, et al., Trends Biochem. Sci., 11:287 [1986]; and Maniatis, et al., Science 236:1237 [1987]). For example, the SV40 early gene enhancer is very active in a wide variety of cell types from many mammalian species and has been widely used for the expression of proteins in mammalian cells (Dijkema, et al., EMBO J. 4:761 [1985]). Other examples of promoter/enhancer elements active in a broad range of mammalian cell types are those from the human elongation factor 1α gene (Uetsuki et al., J. Biol. Chem., 264:5791 [1989]; Kim et al., Gene 91:217 [1990]; and Mizushima and Nagata, Nucl. Acids. Res., 18:5322 ([990]) and the long terminal repeats of the Rous sarcoma virus (Gorman et al., Proc. Natl. Acad. Sci. USA 79:6777 [1982]) and the human cytomegalovirus (Boshart et al., Cell 41:521 [1985]).

The terms "promoter element" or "promoter" as used herein refer to a DNA sequence that is located at the 5' end of (i.e., precedes) a gene in a DNA polymer and provides a site for initiation of the transcription of the gene into mRNA.

The terms "gene of interest" and "nucleotide sequence of interest" refer to any gene or nucleotide sequence, respectively, the manipulation of which may be deemed desirable for any reason by one of ordinary skill in the art.

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes include a promoter, optionally an operator sequence, a ribosome binding site and possibly other sequences. Eukaryotic cells are known to utilize promoters, enhancers, and termination and polyadenylation signals.

A "modification" as used herein in reference to a nucleic acid sequence refers to any change in the structure of the nucleic acid sequence. Changes in the structure of a nucleic acid sequence include changes in the covalent and non-covalent bonds in the nucleic acid sequence. Illustrative of these changes are mutations, mismatches, strand breaks, as well as covalent and non-covalent interactions between a nucleic acid sequence (which contains unmodified and/or modified nucleic acids) and other molecules. Illustrative of a covalent interaction between a nucleic acid sequence and another molecule are changes to a nucleotide base (e.g., formation of thymine glycol) and covalent cross-links between double-stranded DNA sequences which are introduced by, for example, ultraviolet radiation or by cis-platinum. Yet another example of a covalent interaction between a nucleic acid sequence and another molecule includes covalent binding of two nucleic acid sequences to psoralen following ultraviolet irradiation. Non-covalent interactions between a nucleic acid sequence and another molecule include non-covalent interactions of a nucleic acid sequence with a molecule other than a nucleic acid sequence and other than a polypeptide sequence. Non-covalent interactions between a nucleic acid sequence with a molecule other than a nucleic acid sequence and other than a polypeptide sequence are illustrated by non-covalent intercalation of ethidium bromide or of psoralen between the two strands of a double-stranded deoxyribonucleic acid sequence. The present invention contemplates modifications which cause changes in a functional property (or properties), such changes manifesting themselves at a variety of time points.

The term "allelic series" when made in reference to a gene refers to wild-type sequences of the gene. An "allelic series of modifications" as used herein in reference to a gene refers to two or more nucleic acid sequences of the gene, where each of the two or more nucleic acid sequences of the gene contains at least one modification when compared to the wild-type sequences of the gene.

As used herein, the term "mutation" refers to a deletion, insertion, or substitution. A "deletion" is defined as a change in a nucleic acid sequence in which one or more nucleotides is absent. An "insertion" or "addition" is that change in a nucleic acid sequence which has resulted in the addition of one or more nucleotides. A "substitution" results from the replacement of one or more nucleotides by a molecule which is a different molecule from the replaced one or more nucleotides. For example, a nucleic acid may be replaced by a different nucleic acid as exemplified by replacement of a thymine by a cytosine, adenine, guanine, or uridine. Alternatively, a nucleic acid may be replaced by a modified nucleic acid as exemplified by replacement of a thymine by thymine glycol.

The term "mismatch" refers to a non-covalent interaction between two nucleic acids, each nucleic acid residing on a different polynucleic acid sequence, which does not follow the base-pairing rules. For example, for the partially complementary sequences 5'-AGT-3' and 5'-AAT-3', a G-A mismatch is present.

The terms "nucleic acid" and "unmodified nucleic acid" as used herein refer to any one of the known four deoxyribonucleic acid bases (i.e., guanine, adenine, cytosine, and thymine). The term "modified nucleic acid" refers to a nucleic acid whose structure is altered relative to the structure of the unmodified nucleic acid. Illustrative of such modifications would be replacement covalent modifications of the bases, such as alkylation of amino and ring nitrogens as well as saturation of double bonds.

The term "modified cell" refers to a cell which contains at least one modification in the cell's genomic sequence.

The term "nucleic acid sequence-modifying agent" refers to an agent which is capable of introducing at least one modification into a nucleic acid sequence. Nucleic acid sequence-modifying agents include, but are not limited to, chemical compounds (e.g., N-ethyl-N-nitrosurea (ENU), methylnitrosourea (MNU), procarbazine hydrochloride (PRC), triethylene melamine (TEM), acrylamide monomer (AA), chlorambucil (CHL), melphalan (MLP), cyclophosphamide (CPP), diethyl sulfate (DES), ethyl methane sulfonate (EMS), methyl methane sulfonate (MMS), 6-mercaptopurine (6 MP), mitomycin-C (MMC), procarbazine (PRC), N-methyl-N'-nitro-N-nitrosoguanidine (MNNG), $^3H_2O$, and urethane (UR)), and electromagnetic radiation (e.g., X-ray radiation, gamma-radiation, ultraviolet light).

The term "wild-type" when made in reference to a gene refers to a gene which has the characteristics of that gene when isolated from a naturally occurring source. A wild-type gene is that which is most frequently observed in a population and is thus arbitrarily designated the "normal" or "wild-type" form of the gene. In contrast, the term "modified" or "mutant" refers to a gene or gene product which displays modifications in sequence and/or functional properties (i.e., altered characteristics) when compared to the wild-type gene or gene product. It is noted that naturally-occurring mutants can be isolated; these are identified by the fact that they have altered characteristics when compared to the wild-type gene or gene product. Indeed, in some preferred embodiments of the present invention, the modified gene products (i.e., peptides and proteins) induce apoptosis or fibrosis. Thus, in some particularly preferred embodiments, the modified C/EBPβs of the present invention are suitable for the induction of apoptosis in fibrotic tissue, such that the detrimental effects of fibrosis are prevented, reduced, or eliminated. In further embodiments, the modified C/EBPβs of the present invention find use in the induction of fibrosis, such that processes that depend upon fibrosis (e.g., wound healing) are promoted.

A "variant of C/EBPβ" is defined as an amino acid sequence which differs by one or more amino acids from the C/EBPβ wild-type sequence. Variant C/EBPβs also comprise "modified C/EBPβ" proteins and peptides. In some embodiments, variant peptides (i.e., modified) may have "conservative" changes, wherein a substituted amino acid has similar structural or chemical properties (e.g., replacement of leucine with isoleucine). More rarely, a variant (i.e., modified) peptide has "nonconservative" changes (e.g., replacement of a glycine with a tryptophan). Similar minor variations also include amino acid deletions or insertions (i.e., additions), or both. Guidance in determining which and how many amino acid residues may be substituted, inserted or deleted without abolishing biological or immunological activity may be found using computer programs well known in the art, for example, DNAStar software. In some particularly preferred embodiments, the threonine in position 217 of the wild-type murine C/EBPβ is substituted with an alanine or glutamic acid. In still further embodiments, the serine in position 105 of the wild-type rat C/EBPβ is substituted with an alanine or aspartic acid. In yet further embodiments, the threonine in position 266 of the wild-type human C/EBPβ is substituted with either an alanine or glutamic acid.

As used herein, the term "biological agent" refers to an agent that is useful for diagnosing or imaging or that can act on a cell, organ or organism, including but not limited to drugs (e.g., pharmaceuticals) to create a change in the functioning of the cell, organ or organism.

As used herein, the term "sample" is used in its broadest sense. In one sense it can refer to a composition comprising a therapeutic agent. In another sense, it is Qmeant to include a specimen or culture obtained from any source. Biological samples may be obtained from animals (including humans) and encompass tissues (e.g., biopsy samples), fluids, solids, tissues, and gases. Biological samples also include blood products, such as plasma, serum and the like. These examples are not to be construed as limiting the sample types applicable to the present invention.

As used herein, the term "chemotherapeutic agent" refers to an agent that inhibits the growth or decreases the survival of neoplastic or pathogenic microbial cells or inhibits the propagation (which includes without limitation replication, viral assembly or cellular infection) of a virus. It is intended that the definitions encompass compounds purified from the natural source, as well as compounds prepared synthetically or by semisynthesis. Thus, it is not intended that the present invention be limited to these compounds produced in by a particular method or from any specific source.

The term "compound" refers to any chemical entity, pharmaceutical, drug, and the like that can be used to treat or prevent a disease, illness, sickness, or disorder of bodily function. Compounds comprise both known and potential therapeutic compounds. A compound can be determined to be therapeutic by screening using the screening methods of the present invention. A "known therapeutic compound" refers to a therapeutic compound that has been shown (e.g., through animal trials or prior experience with administration to humans) to be effective in such treatment. In other words, a known therapeutic compound is not limited to a compound efficacious in the treatment of cancer.

The term "test compound" refers to any chemical entity, pharmaceutical, drug, and the like that can be used to treat or prevent a disease, illness, sickness, or disorder of bodily function. Test compounds comprise both known and potential therapeutic compounds. A test compound can be determined to be therapeutic by screening using the screening methods of the present invention. A "known therapeutic compound" refers to a therapeutic compound that has been shown (e.g., through animal trials or prior experience with administration to humans) to be effective in such treatment or prevention. In other words, a known therapeutic compound is not limited to a compound efficacious in the treatment of fibrosis.

A compound is said to be "in a form suitable for administration to the mammal" when the compound may be administered to a mammal by any desired route (e.g., oral, intravenous, subcutaneous, intramuscular, etc.) and the compound or its active metabolites appears in the blood of the mammal. Administration of a compound to a pregnant female may result in delivery of the compound to the fetuses of the pregnant animal.

A "composition comprising a given polynucleotide sequence" as used herein refers broadly to any composition containing the given polynucleotide sequence. The composition may comprise an aqueous solution. Compositions comprising polynucleotide sequences encoding human, mouse, and/or rat C/EBPβ or fragments thereof may be employed as hybridization probes. In this case, the CEBPβ-encoding polynucleotide sequences are typically employed in an aqueous solution containing salts (e.g., NaCl), detergents (e.g., SDS) and other components (e.g., Denhardt's solution, dry milk, salmon sperm DNA, etc.).

As used herein, the term "pharmaceutical composition" refers to any composition or compound suitable for administration to a subject for treatment and/or prevention of disease. It is contemplated that such compositions encompass drugs that are effective in reducing or eliminating signs and symptoms of disease. It is not intended that the present invention be limited to any particular dosage or administration strategy. It is also intended that the term encompass various regimens, including, but not limited to regimens in which a combination of pharmaceutical compositions are provided in separate vehicles (e.g., separate tablets, pills, liquids, etc.).

As used herein, the term "therapeutically effective amount" refers an amount of a therapeutic agent that inhibits the growth or decreases the survival of neoplastic cells.

As used herein, the terms "subtherapeutic amount" and "subtherapeutic concentration" refer to an amount of a therapeutic that is administered at a concentration that would not be expected to exhibit complete destruction of cells.

As used herein, the term "anti-proliferative" refers to a therapeutic agent that suppresses or inhibits the growth of abnormal cells, but does not necessarily kill the cells.

As used herein, the term "cytotoxic" drug or agent refers to a therapeutic agent useful in treating disease that results in the death of cells. In some preferred embodiments, cytotoxic drugs are particularly effective against rapidly dividing cells.

As used herein, the term "$IC_{50}$" refers to the concentration at which 50% cytotoxicity is obtained. Cytotoxicity can be measured by the method of Alley et al., Cancer Res. 48: 589-601, 1988 or Scudiero et al., Cancer Res., 48:4827, 1988, or by any other suitable method known in the art. In one embodiment, cytotoxicity can be measured based on the drug concentration at which a 50% reduction in the activity of mitochondrial enzymes is observed.

As used herein, the term "subject" refers to a human or other animal of interest. In some preferred embodiments, the subject is any living animal that is capable of being treated with a pharmaceutical composition.

As used herein, the term "hepatitis C" refers to subjects infected with the hepatitis C virus, a single-stranded RNA virus that possesses a lipid-containing envelope and is thought to be a member of the flavivirus family. The term encompasses all forms of hepatitis C, including acute hepatitis C and all forms of chronic hepatitis C (e.g., chronic active hepatitis and chronic persistent hepatitis).

As used herein, the phrase "symptoms of hepatitis C" refers broadly to clinical manifestations, laboratory and imaging results, as well as liver morphology and histology exhibited by subjects which suggest the presence of hepatitis C. Clinical manifestations may include, but are not limited to, abdominal pain, jaundice, hepatosplenomegaly, and ascites. Laboratory and imaging results may include, but are not limited to, elevated serum aminotransferase, bilirubin, and gamma-globulin levels, as well as an enlarged liver on computed tomography, magnetic resonance imaging, and hepatic ultrasonography. Hepatic morphological and histological indicators of hepatitis C may include, but are not limited to, deposition of fibrotic tissue evident through liver biopsy.

As used herein, the term "fibrosis" refers to the formation of fibrous tissue as a reparative or reactive process, such as that which occurs during the development of scar tissue which replaces normal tissue following injury, inflammation, and/or infection. In some embodiments, the term refers to the replacement of normal smooth muscle or other normal tissue with fibrous connective tissue. Fibrosis can occur in any tissue and involve localized or more widespread effects. Localized fibrosis may be complicated by infarctions, abscesses, bronchiectasis, and/or other pathologies.

As used herein, the term "apoptosis" refers to cell death. In particular, apoptosis refers to programmed cell death which is distinct from the necrotic process. During apoptosis, cells undergo various changes that result in the eventual lysis of the cell into apoptotic bodies which are then typically phagocytosed by other cells.

As used herein, the phrases "symptoms indicating fibrosis," refer to the morphological and histological indicators of fibrosis in any tissue. In particularly preferred embodiments, the term "hepatic fibrosis" refers to morphological and histological indicators of fibrosis involving the liver. Such indicators may include, but are not limited to, deposition of fibrotic tissue evident through liver biopsy and activation of the fibrogenesis cascade as evidenced by increased MDA-adducts, stellate cell activation, and enhanced expression of c-myb and collagen α1(I) mRNA in stellate cells.

As used herein, the term "diminished" means that there has been a reduction in the extent of the symptoms of fibrosis, etc. In general, such a reduction is demonstrated by objective indicators. For example, comparison of liver biopsy samples taken before and after administration of a therapeutic agent may indicate a reduction in hepatic fibrosis. In addition, reduction of symptoms may also be demonstrated by subjective indicators, such as a reduction in abdominal pain.

As used herein, the term "therapeutic composition" refers to a composition that includes a compound in a pharmaceutically acceptable form that prevents and/or reduces fibrosis, including but not limited to hepatic fibrosis. The characteristics of the form of the therapeutic composition will depend on a number of factors, including the mode of administration. The therapeutic composition may contain diluents, adjuvants and excipients, among other things.

As used herein, the term "parenterally" refers to administration to a subject through some means other than through the gastrointestinal tract or the lungs. Common modes of parenteral administration include, but are not limited to, intravenous, intramuscular, and subcutaneous administration.

As used herein, the terms "therapeutic amount," "effective amount," and the like, refer to that amount of a compound or preparation that successfully prevents the symptoms of fibrosis and/or reduces the severity of symptoms. The effective amount of a therapeutic composition may depend on a number of factors, including the age, immune status, race, and sex of the subject and the severity of the fibrotic condition and other factors responsible for biologic variability.

The "non-human animals having a genetically engineered genotype" of the invention are preferably produced by experimental manipulation of the genome of the germline of the non-human animal. These genetically engineered non-human animals may be produced by several methods including the introduction of a "transgene" comprising nucleic acid (usually DNA) into an embryonal target cell or integration into a chromosome of the somatic and/or germ line cells of a non-human animal by way of human intervention, such as by the methods described herein. Non-human animals which contain a transgene are referred to as "transgenic non-human animals". A transgenic animal is an animal whose genome has been altered by the introduction of a transgene.

As used herein, the term "transgene" refers to a foreign gene that is placed into an organism by introducing the foreign gene into newly fertilized eggs or early embryos. The term "foreign gene" refers to any nucleic acid (e.g., gene sequence) which is introduced into the genome of an animal by experimental manipulations and may include gene sequences found in that animal so long as the introduced gene does not reside in the same location as does the naturally-occurring gene.

As used herein, "non-human mammal expressing mutant C/EBP protein" is a mammal which expresses a C/EBP protein that is different from that found in a wild-type mammal. A mammal that "lacks the ability to produce functional C/EBP" is a mammal that produces undetectable levels of C/EBP (i.e., a level which is not statistically above background levels in the assay employed). A functional C/EBP protein is a C/EBP, which has the same properties as does the wild-type C/EBP including molecular weight. A functionally active fragment of human C/EBP is capable of functioning in vitro and/or in vivo in a manner that is similar or the same as full-length C/EBP. "Functional activity" also encompasses such activities normally associated with C/EBP proteins.

DESCRIPTION OF THE DRAWINGS

FIG. 8 provides the nucleotide sequence (SEQ ID NO:1) and amino acid sequence (SEQ ID NO:2) of wild-type mouse C/EBPβ.

FIG. 9 provides the amino acid sequence of modified mouse C/EBPβ in which the threonine present in wild-type murine C/EBPβ at position 217 (SEQ ID NO:2) is replaced with alanine (SEQ ID NO:3), as well as the amino acid sequence of modified mouse C/EBPβ in which the threonine present in wild-type murine C/EBPβ at position 217 (SEQ ID NO:2) is replaced with glutamic acid (SEQ ID NO:4).

FIG. 10 provides the nucleotide sequence (SEQ ID NO:5) and amino acid sequence (SEQ ID NO:6) of wild-type human C/EBP.delta., which corresponds to Genbank Accession No. M83667.

FIG. 11 provides the amino acid sequence of modified human C/EBP.delta., in which the threonine at position 265 is replaced with alanine (SEQ ID NO:7), as well as the amino acid sequence of modified human C/EBP.delta., in which the threonine at position 265 is replaced with glutamic acid (SEQ ID NO:8).

FIG. 12 provides the amino acid sequence (SEQ ID NO:9) of human c/EBP.beta., as well as the amino acid sequence of modified human C/EBP.beta., in which the threonine at position 266 of human C/EBP.beta. (SEQ ID NO:9) is replaced with alanine (SEQ ID NO:10), and the amino acid sequence of modified human C/EBP.beta., in which the threonine at position 266 of human C/EBP.beta. (SEQ ID NO:9) is replaced with glutamic acid (SEQ ID NO:11).

FIG. 13 provides the nucleotide sequence (SEQ ID NO:18) and amino acid sequence (SEQ ID NO:19) of wild-type human C/EBPβ that corresponds to Genbank Accession No. X52560.

FIG. 14 provides the amino acid sequence of modified human C/EBPβ, in which the threonine at position 266 of the wild-type human C/EBPβ (SEQ ID NO:19) is replaced with alanine (SEQ ID NO:20), as well as the amino acid sequence of modified human C/EBPβ, in which the threonine at position 266 of the wild-type human C/EBPβ (SEQ ID NO:19) is replaced with glutamic acid (SEQ ID NO:21).

FIG. 15 provides the nucleotide sequence (SEQ ID NO:22) and amino acid sequence (SEQ ID NO:23) of wild-type human C/EBPβ that corresponds to Genbank Accession No. NM_005194.

FIG. 16 provides the amino acid sequence of modified human C/EBPβ, in which the threonine at position 266 of the wild-type human C/EBPβ (SEQ ID NO:23) is replaced with alanine (SEQ ID NO:24), as well as the amino acid sequence of modified human C/EBPβ, in which the threonine at position 266 of the wild-type human C/EBPβ (SEQ ID NO:23) is replaced with glutamic acid (SEQ ID NO:25).

FIG. 17 provides the nucleotide sequence (SEQ ID NO:12) and amino acid sequence (SEQ ID NO:13) of wild-type rat c/EBPβ.

FIG. 18 provides the amino acid sequence of modified rat C/EBPβ in which the serine at position 105 of the wild-type rat C/EBPβ (SEQ ID NO:13) is replaced with alanine (SEQ ID NO:14), as well as the amino acid sequence of modified rat C/EBPβ in which the serine at position 105 of the wild-type rat C/EBPβ (SEQ ID NO:13) is replaced with aspartic acid (SEQ ID NO:15).

DESCRIPTION OF THE INVENTION

Figure 1:
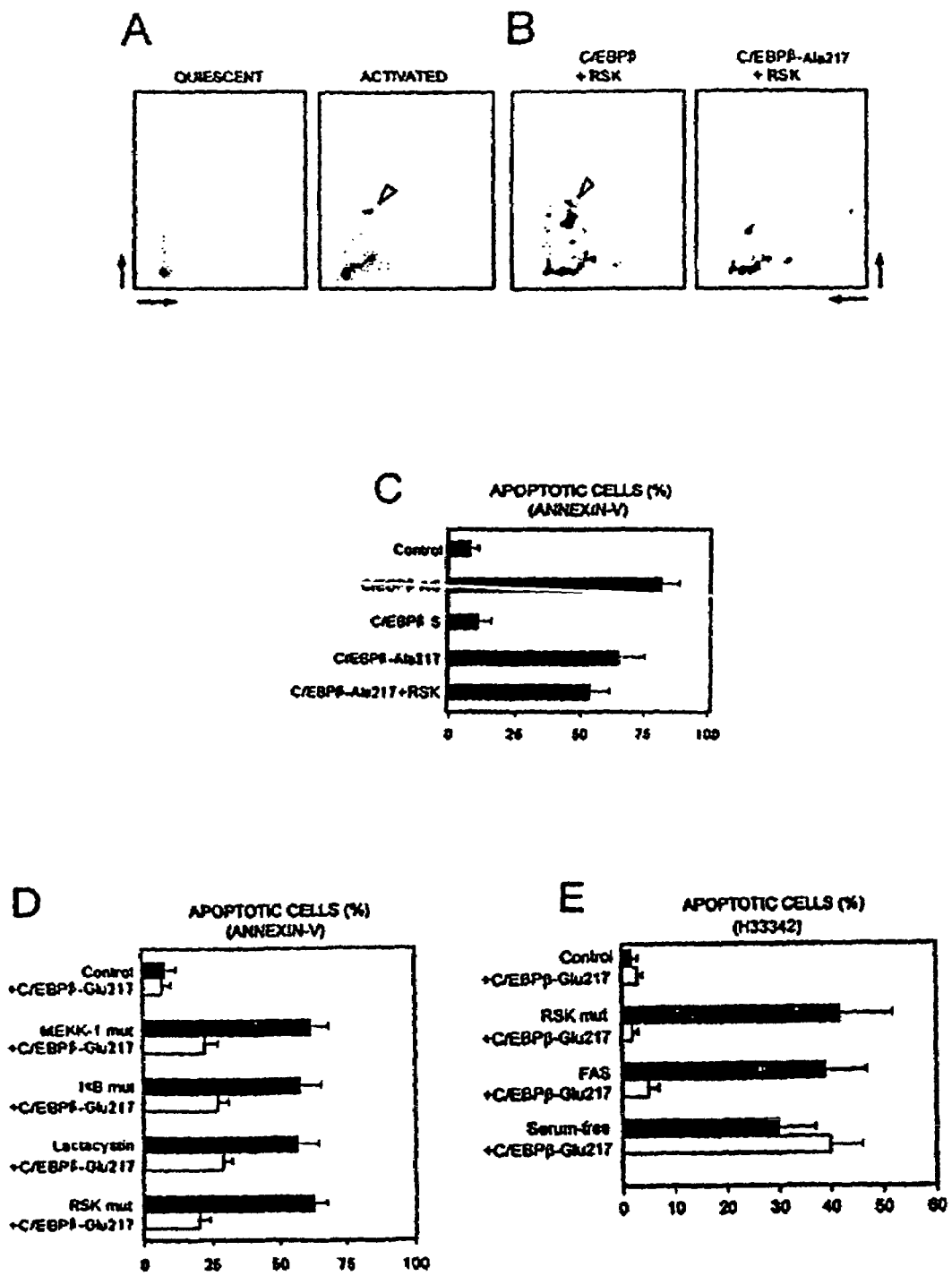
FIG. 1 provides data showing that phosphorylation of C/EBPβ on Thr$^{217}$ is required for hepatic stellate cell survival. Panel A provides phosphopeptide maps of in vivo labeled endogenous C/EBPβ in day-4 quiescent and activated primary mouse stellate cells cultured from the time of isolation on EHS or collagen type I matrix, respectively. The arrow indicates the peptide containing Phospho-Thr$^{217}$ in activated cells. These results indicate that collagen type I induces phosphorylation of C/EBPβ on Thr$^{217}$. Panel B provides phosphopeptide maps of in vitro labeled C/EPBβ. Active p90RSK phosphorylated C/EPBβ, but not C/EBPβ-Ala$^{217}$ on Thr$^{217}$ in vitro (arrowheads). Panel C provides results for cells cultured on collagen type I transfected with MSV-C/EBPβ antisense (AS), MSV-C/EBPβ sense (S), or MSV-C/EBPβ-Ala$^{217}$ together with CMV-GFP (green fluorescent protein) and p90RSK (1 μg each), as indicated in the Figure. Four hours after transfection, annexin-V-PE binding to plasma membranes was determined. The values presented are the percentage of transfected cells (green) that were annexin-V-PE (+) (red) ($P<0.05$ for C/EBPβ AS, and C/EBPβ-Ala$^{217}$). Panel D provides results for cells transfected as in Panel A with vectors expressing dominant negative mutants for MEKK1, IκBα, or p90RSK, or treated with the proteasome inhibitor lactacystin (10 μM) (closed bars), and co-transfected with MSV-C/EBPβ-Glu$^{217}$ (1 μg each) (open bars) as indicated. Annexin-V-PE binding was determined as described for Panel A ($P<0.05$ for C/EBPβ-Glu$^{217}$). Panel E provides results for cells transfected as described for Panel C, with a dominant-negative p90RSK, treated with FAS (100 nM for 6 hours) or cultured in a serum-free medium for 6 hours (closed bars), and co-transfected with MSV-C/EBPβ-Glu$^{217}$ (1 μg each) (open bars), as indicated. Cell death was determined by nuclear staining with Hoechst 33342 ($P<0.05$ for C/EBPβ-Glu$^{217}$ in RSK mut and FAS-treated cells).

The present invention relates generally to the treatment and prevention of diseases characterized by excess cell proliferation and/or activation. In particular, the present invention provides compositions and methods to suppress the activation and/or proliferation of various cells. In preferred embodiments, the present invention provides compositions and methods to suppress the activation and/or proliferation of mesenchymally derived cells (including, but not limited to hepatic stellate cells), as well as cells with abnormal growth characteristics. In particularly preferred embodiments, the present invention provides compositions and methods to inhibit or eliminate fibrosis. In alternative preferred embodiments, the present invention provides compositions and methods to induce fibrosis.

The CCAAT/Enhancer Binding Protein β (C/EBPβ) (Descombes et al., Genes Dev., 4:1541-1551 [1990]; and Akira et al., EMBO J., 9:1897-1906 [1990]) mediates the proliferative effects of oxidative stress and of ribosomal protein S-6 kinase (RSK) activated by transforming growth factor (TGF) α in colonic cancer cells (Chinery et al., Nat. Med., 3:1233-1241 [1997]) and primary mouse hepatocytes (Buck et al., Mol. Cell., 4:1087-1092 [1999]), respectively. However, the mechanisms linking C/EBPβ (LAP, NF-IL6) to cell proliferation are unknown. Indeed, an understanding of these mechanisms is not necessary in order to use the present invention.

Activation of the ERK/MAPK signal transduction pathway promotes cell proliferation through several mechanisms, including stimulation of nucleotide synthesis, gene expression, protein synthesis and cell growth (Whitmarsh and Davis, J. Mol. Med., 74:589-607 [2000]). Many of these MAPK's roles in cell growth are mediated by p90RSK (Nebreda and Gavin, Science 286:1309-1310 [1999]). RSK phosphorylates and inactivates the pro-apoptotic protein BAD (Bonni et al., Science 286:1358-1362 [1999]); up-regulates transcription of the anti-apoptotic gene Bcl-2 through phosphorylation and activation of CREB (Bonni et al., supra); and facilitates gene expression by inducing chromatin remodeling via phosphorylation of histone H3 (Sassone-Corsi et al., Science 285:886-891 [1999]).

In response to epidermal growth factor, the ERK/MAPK cascade regulates the de novo synthesis of pyrimidine nucleotides by activating carbamoyl phosphate synthetase II (Graves et al., Nature 403:328-332 [2000]). Other mechanisms by which the ERK/MAPK signaling pathway modulates cell survival and the cell cycle (Whitmarsh and Davis, J. Mol. Med., 403:255-256 [1996]) include: a) activation of transcription by phosphorylation of transcriptional factors (Whitmarsh and Davis, J. Mol. Med., 74:589-607 [1996]; Bhatt and Ferrell, Science 286:1362-1365 [1999]) and histone H3 and HMG-14 (Sassone-Corsi et al., supra; and Thomson et al., EMBO J., 17:4779-4793 [1999]); b) stimulation of translation through phosphorylation of initiation factor 4E (eIF-4E) (Pyronnet et al., EMBO J., 18:270-279 [1999]); and c) promotion of DNA replication by increasing expression of cyclin D1 (Lavoie et al., J. Biol. Chem., 271:206086-20616 [1996]). RSK, which is activated by ERK/MAPK phosphorylation, plays an essential role in the ERK/MAPK signaling pathway regulating cell survival and the cell cycle (Bonni et al., supra; Bhatt and Ferrell, supra; Gross et al., Science 286:1365-1367 [1999]; and Sassone-Corsi et al., supra). Thus, the function of C/EBPβ in cell survival mediated by RSK was of interest in the development of the present invention.

Primary mouse hepatic stellate cells were used during the development of the present invention, as overproduction of fibrous tissue by these cells (Friedman et al., Proc. Natl. Acad. Sci. USA 82:8681-8685 [1985]; and Ankoma-Sey and Friedman, in Strain and Diehl (eds), Liver Growth and Repair, Chapman & Hall, London, pages 512-537 [1998]) is a critical step in the development of liver cirrhosis following liver injury (Chojkier, in Strain and Diehl (eds.) Liver Growth and Repair, supra, at pages 430-450). Furthermore, these cells remain quiescent, as in the normal liver (Lee et al., J. Clin. Invest., 96:2461-2468 [1995]; and Ankoma-Sey and Friedman, supra), when cultured on an EHS (Matrigel) matrix but are rapidly activated and proliferate with the induction of oxidative stress by either collagen type I or TGFα in culture (Lee et al., supra; and Friedman et al., J. Biol. Chem., 264: 10756-10762), which also modulate C/EBPβ's effects on cell growth (Chinery et al., supra; and Buck et al., [1999], supra). Similarly, stellate cell activation follows the stimulation of oxidative stress both in experimental liver injury with $CCl_4$ (Houglum et al., J. Clin. Invest., 96:2269-2276 [1995]) and in human liver diseases induced by alcohol, genetic hemochromatosis, porphyria and viral hepatitis (Chojkier, supra). However, until the development of the present invention, it was unknown that the survival dependency of activated hepatic stellate cells requires phosphorylation of C/EBPβ (e.g., mouse C/EBPβ; (m) C/EBPβ) on $Thr^{217}$ by RSK. As described in greater detail herein, the hepatotoxin $CCl_4$ induced activation of RSK, phosphorylation of C/EBPβ on $Thr^{217}$ and proliferation of stellate cells in normal mice, but caused apoptosis of these cells in $C/EBPβ^{-/-}$ and C/EBPβ-$Ala^{217}$ (a dominant negative non-phosphorylatable mutant) transgenic mice. In other words, following the induction of hepatic oxidative stress with $CCl_4$, stellate cells from $C/EBPβ^{-/-}$ or C/EBPβ-$Ala^{217}$ (a non-phosphorylatable mutant) transgenic, but not $C/EBPβ^{+/+}$, mice developed apoptosis. Furthermore, both C/EBPβ-$PThr^{217}$ and the phosphorylation mimic C/EBPβ-$Glu^{217}$, but not C/EBPβ-$Ala^{217}$, were found to associate with procaspases 1 and 8 in vitro and in vivo, and inhibit their activation. The data obtained during the development of the present invention indicate that C/EBPβ phosphorylation of $Thr^{217}$ creates a functional XEXD caspase substrate/inhibitor box (KPhospho-$T^{217}$VD) that is mimicked by C/EBPβ-$Glu^{217}$ ($KE^{217}VD$). Consistent with this observation, $C/EBPβ^{-/-}$ and C/EBP-$Ala^{217}$ stellate cells were rescued from apoptosis by either the cell permeant $KE^{217}VD$ tetrapeptide or C/EBPβ-$Glu^{217}$, as described in greater detail herein.

Results obtained during the development of the present invention and described in further detail herein, indicate that there is a novel C/EBPβ mechanism for cell survival downstream of RSK, preventing activation of procaspases 1 and 8 (Thornberry and Lazebnik, Science 281:1312-1316 [1998]). These caspases activate downstream effector procaspases (Earnshaw et al., Ann. Rev. Biochem., 68:383-424 [1999]). Physiologically relevant signaling pathways in stellate cells, such as $CCl_4$ in mice and collagen type I in culture (Friedman et al., J. Biol. Chem., 264:10756-10762 [1989]; and Rudolph et al., Science 287:1253-1258 [2000]), result in the activation of RSK and phosphorylation of endogenous C/EBPβ on Thr$^{217}$. C/EBPβ-PThr$^{217}$, but not unphosphorylated C/EBPβ, associates with procaspases 1 and 8 (as detected by immunofluorescence, co-immunoprecipitation and direct in vitro association of recombinant proteins) and inhibits their processing, which blocks the apoptotic cascades and allows survival of stellate cells. Thus, the present data provide the first demonstration that phosphorylation of a transcription factor by the ERK/MAPK/RSK pathway stimulates its association with procaspases, preventing their activation. Although it is possible that phosphorylation of C/EBPβ on Thr$^{217}$ to create a functional XEXD caspase substrate/inhibitor box (Thornberry et al., J. Biol. Chem., 272:17907-17911 [1997]; and Blanchard et al., J. Mol. Biol., 302:9-16 [2000]) explains the anti-apoptotic role of C/EBPβ, structural analysis is required to elucidate the exact mechanism. Regardless, an understanding of the mechanisms is not necessary in order to use the present invention.

The inhibition of procaspase 1 and 8 activation by C/EBPβ-PThr$^{217}$ occurs under conditions in which C/EBPβ expression is physiologically induced, such as activation of normal stellate cells either in mice treated with the hepatotoxin $CCl_4$ or in culture on a collagen type I matrix. Moreover, apoptosis is induced under these conditions in stellate cells from C/EBPβ$^{-/-}$ mice. These experiments indicate that the findings are not the spurious result of overexpressing C/EBPβ. Expression of C/EBPβ-Ala$^{217}$ in transgenic mice also induced apoptosis of stellate cells upon exposure to growth stimuli ($CCl_4$ in mice and collagen in culture). In contrast, the phosphorylation mimic C/EBPβ-Glu$^{217}$ mutant rescued cells from apoptosis induced either by expressing MEKK1, IKBα or RSK dominant negative mutants or by treating the cells with the proteasome inhibitor lactacystin (Chen et al., Nature 374:386-388 [1995b]; Nakajima et al., Cell 86:465-474 [1996]; and Lee et al., Cell 88:213-222 [1997]). Expression of C/EBPβ-Glu$^{217}$ in stellate cells also prevented FAS-induced apoptosis, which is mediated by activation of procaspase 8 (Ashkenazi and Dixit, Science 281: 1305-1208 [1998]), but not apoptosis induced by serum deprivation, which is mediated by activation of procaspase 9 (Joza et al., Nature 410:549-554 [2001]). These results indicate selective effects of C/EBPβ-PThr$^{217}$ on apoptosis. C/EBPβ's activation and dimerization domains are not necessary for its association with or inhibition of procaspases 1 and 8. Furthermore, preliminary experiments in stellate cells using reporter genes, which contain C/EBPβ binding domains (Descombes et al. supra; and Houglum et al., J. Clin. Invest., 94:808-814 [1994]), did not show differences in transcription activation between C/EBPβ wild type and the phosphorylation or Ala$^{219}$ mutants.

C/EBPβ-PThr$^{217}$ is mimicked by C/EBPβ-Glu$^{217}$ (KE$^{217}$VD) and therefore, conforms to the current knowledge about the structural requirements for caspase inhibitory/substrate tetrapeptides. These tetrapeptides require an aspartic acid (D) residue at the P1 position (Thornberry and Lazebnik, supra), which is also present in C/EBPβ at amino acid D$^{219}$ (Cao et al., Genes Develop., 5:1538-1552 [1991]). Using a positional scanning substrate library, it has been shown that the optimal sequence for caspase 8 is I/L/V (P4 position) EXD, although I, V, W, T, P and D are also acceptable at the P4 position, by virtue of being downstream cleavage sites in the apoptotic cascade (Thornberry et al., supra). These findings have been recently corroborated by crystallographic studies of caspase 8. (Blanchard et al., supra). Although group III caspases (including caspase 8) have a preference for small hydrophobic residues at P4, kinetic and crystallographic studies have shown that DEVD, a specific group II inhibitor, containing a hydrophilic residue at this position, interacts favorably with the enzyme in subsite S4, and it is an almost equally potent inhibitor as the specific group III inhibitor IETD (Blanchard et al., supra). The K$^{216}$ in C/EBPβ has a similar hydrophobicity as D (Boyle et al., Meth. Enzymol., 201:110-149 [1991]). In addition, Blanchard et al. argue that subsite S3 of caspase 8, which interacts with position P3 (but not with P4) of the tetrapeptide, is crucial for determining the specificity, and that the original classification of caspases need to be revised, especially for caspase 8 (Blanchard et al., supra). Like the selective effects of C/EBPβ-PThr$^{217}$ observed during the development of the present invention, CrmA inhibits procaspases 1 and 8 selectively compared to procaspases 3, 6 and 7 (Zhou et al., J. Biol. Chem., 272:7797-7800 [1997]). However, other reports have suggested that CrmA also inhibits caspases 4, 5, 9 and 10 (Garcia-Calvo et al., J. Biol. Chem., 273:32608-32613 [1998]). In addition, the baculovirus p35 is a potent, albeit less selective, inhibitor of procaspases 1, 3, 6, 8, and 10 (Andrade et al., Immun., 8:451-460 [1998]). In addition, experiments conducted during the development of the present invention have shown that the sequence K-Phospho-T$^{217}$VD (or KE$^{217}$VD) within C/EBPβ is effective in associating with procaspases 1 and 8 and blocking their activation.

The experiments with C/EBPβ$^{-/-}$ cells and with dominant negative Ala$^{217}$ and dominant positive Glu$^{217}$ mutants, including C/EBPβ-Ala$^{217}$ transgenic mice, strongly support the present invention. The C/EBPβ-Ala$^{217}$ mutant associates with RSK and acts as a dominant negative, following proliferation of stellate cells in animals and in culture induced by $CCl_4$ and collagen type I, respectively. The synthetic Ac-KA$^{217}$VD-CHO peptide stimulates apoptosis of stellate cells, resembling the dominant negative effects of C/EBPβ-Ala$^{217}$ and C/EBPβ216-253-Ala$^{217}$. These effects could result from the inhibition of RSK and/or the facilitation of procaspases 1 and 8 activation, possibly by impeding the binding of C/EBPβ-PThr$^{217}$ to procaspases 1 and 8, while allowing their self-cleavage. Nonetheless, an understanding of the mechanisms is not necessary in order to use the present invention.

Although rC/EBPβ has a naturally occurring Ala for Thr substitution at position 217, rC/EBPβ also has a Ser for Ala substitution at position 105 (Buck et al., [1999], supra). It was also observed that endogenous rC/EBPβ is phosphorylated on Ser$^{105}$ (the RSK rat phosphoacceptor homologue). Expression of the dominant positive rC/EBPβ-Asp$^{105}$ was sufficient to rescue cells from apoptosis induced by expressing a dominant negative mutant RSK or by treatment with a proteasome inhibitor. Activation of the PKCα or MAPK signaling pathways results in phosphorylation of rC/EBPβ on Ser$^{105}$ (Trautwein et al., Nature 364:544-547 [1993]; and Buck et al. [1999], supra). Moreover, stellate cells isolated from rC/EBPβ-Asp$^{105}$ transgenic mice were refractory to the induction of apoptosis by lactacystin. As described for C/EBPβ, rC/EBPβ peptides containing either P-Ser$^{105}$ or its phosphorylation mimic Asp$^{105}$, associated with procaspases 1 and 8 in rat stellate cells. The Ac-KKPD$^{105}$-CHO tetrapeptide also inhibited activation of procaspase 8. These data indicate that although C/EBPβ or rC/EBPβ are phosphorylated on different amino acid residues, both phosphorylated proteins are sufficient to rescue cells from apoptosis mediated by caspase 8.

In contrast, the non-phosphorylatable rC/EBPβ-Ala$^{105}$ mutant behaves as a dominant negative (comparable to the C/EBPβ-Ala$^{217}$ mutant), inducing apoptosis of both mouse and rat stellate cells. The rC/EBPβ-PSer$^{105}$ sequence is mimicked by KKPD[105], which contains the indispensable D at the P1 position and the highly preferred P at the P2 position as a substrate/inhibitor (XXPD) for granzyme B, as determined by using synthetic substrate libraries (Harris et al., J. Biol. Chem., 273:27364-27373 [1998]). The initiator caspases, caspase 8 and granzyme B, share the tetrapeptide IETD sequence of procaspase 3 as a substrate/inhibitor (Thornberry et al., 1997, supra; Harris et al., supra), indicating that caspase 8 may also recognize the XXPD substrate. This was confirmed by the experimental data obtained during the development of the present invention. The tetrapeptide Ac-KKPD[105]-CHO (rC/EBPβ) significantly inhibited apoptosis of stellate cells from C/EBPβ$^{-/-}$ mice.

The data obtained during the development of the present invention are relevant to diseases that result from the activation of mesenchymal cells, which leads to excessive tissue repair mechanisms (e.g., brain gliosis, liver cirrhosis, and lung and kidney fibrosis). The results described herein indicate that the nonphosphorylatable tetrapeptides of the C/EBPβ RSK phosphoacceptor are suitable for therapeutic uses, as they induce apoptosis of various cells following their activation. Thus, for hepatic stellate cells, these tetrapeptides find use in the prevention of the development of liver fibrosis and cirrhosis. Indeed, C/EBPβ-Ala$^{217}$ transgenic mice are refractory to the induction of liver fibrosis and cirrhosis following the chronic administration of $CCl_4$. In addition, because IL-1 has been implicated in the pathogenesis of acute neurodegeneration (Rothwell et al., J. Clin. Invest., 100: 2648-2652 ([1997]), inhibition of caspase 1 activation and its processing of the IL-1 precursor is contemplated to ameliorate diseases associated with fibrosis and/or apoptosis.

The creation of a functional XEXD caspase inhibitory box by phosphorylation reported herein, may be a prevalent biological mechanism through evolution. Indeed, potential functional XEXD boxes that would be created upon phosphorylation of threonine (Phospho-TVD, analogous to EVD) were identified in more than 22,000 sites and of serine (EV-Phospho-S, analogous to EVD) in more than 27,000 sites in a database containing ~350,000 proteins. If only 1% of these sequences is phosphorylated in vivo, this would generate functional XEXD caspase inhibitory boxes in ~500 proteins. However, as indicated herein, an understanding of the mechanisms involved is not necessary in order to use the present invention.

As discussed in greater detail herein, in one embodiment of the present invention, polynucleotide sequences or fragments thereof which encode C/EBPβ or fusion proteins or functional equivalents thereof, may be used in recombinant DNA molecules to direct expression of C/EBPβ in appropriate host cells. Due to the inherent degeneracy of the genetic code, other DNA sequences which encode substantially the same or a functionally equivalent amino acid sequence may be produced and these sequences may be used to clone and express C/EBPβ.

As will be understood by those of skill in the art, it may be advantageous to produce C/EBPβ nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life which is longer than that of a transcript generated from the naturally occurring sequence.

The nucleotide sequences of the present invention can be engineered using methods generally known in the art in order to alter C/EBPβ-encoding sequences for a variety of reasons, including but not limited to, alterations which modify the cloning, processing, and/or expression of the gene product.

DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, produce splice variants, or introduce mutations, and so forth. In another embodiment of the present invention, natural, modified, or recombinant nucleic acid sequences encoding C/EBPβ may be ligated to a heterologous sequence to encode a fusion protein. For example, to screen peptide libraries for inhibitors of human C/EBPβ activity, it may be useful to encode a chimeric (e.g., human) C/EBPβ protein that can be recognized by a commercially available antibody. A fusion protein may also be engineered to contain a cleavage site located between the C/EBPβ encoding sequence and the heterologous protein sequence, so that the C/EBPβ may be cleaved and purified away from the heterologous moiety.

In another embodiment of the present invention, sequences encoding C/EBPβ may be synthesized, in whole or in part, using chemical methods well known in the art (See e.g., Caruthers et al. Nucl. Acids Res. Symp. Ser., 215-223 [1980]; and Horn et al., Nucl. Acids Res. Symp. Ser., 225-232 [1980]). Alternatively, the protein itself may be produced using chemical methods to synthesize the amino acid sequence of C/EBPβ, or a portion thereof. For example, peptide synthesis can be performed using various solid-phase techniques (Roberge et al., Science 269:202-204 [1995]) and automated synthesis may be achieved, for example, using commercially available synthesizers. These synthesized peptide may be substantially purified by preparative high performance liquid chromatography (HPLC), using any suitable method known in the art. The composition of the synthetic peptides may be confirmed by amino acid analysis or sequencing (e.g., the Edman degradation procedure). Additionally, the amino acid sequence of C/EBPβ or any part thereof, may be altered during direct synthesis and/or combined using chemical methods with sequences from other proteins, or any part thereof, to produce a variant polypeptide.

As described herein in greater detail, in order to express a biologically active C/EBPβ the nucleotide sequences encoding C/EBPβ or functional equivalents, may be inserted into appropriate expression vector (i.e., a vector which contains the necessary elements for the transcription and translation of the inserted coding sequence). Methods well known to those skilled in the art find use in the construction of expression vectors containing sequences encoding C/EBPβ and appropriate transcriptional and translational control elements. These methods include in vitro recombinant DNA techniques, synthetic techniques, and in vivo genetic recombination. A variety of expression vector/host systems may be utilized to contain and express sequences encoding C/EBPβ. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems. Control elements and regulatory sequences are also contemplated, as appropriate.

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells known in the art which have specific cellular machinery and characteristic mechanisms for such post-translational activities, may be chosen to ensure the correct modification and processing of the foreign protein.

For long-term, high-yield production of recombinant proteins, stable expression is preferred. For example, cell lines which stably express C/EBPβ may be transformed using expression vectors which may contain viral origins of replication and/or endogenous expression elements and a selectable marker gene on the same or on a separate vector. Following the introduction of the vector, cells may be allowed to grow for 1-2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type. Any number of selection systems may be used to recover transformed cell lines. These include, but are not limited to, the herpes simplex virus thymidine kinase, adenine phosphoribosyltransferase, and various other suitable systems known in the art. Also, anti-metabolite, antibiotic or herbicide resistance can be used as the basis for selection. Although the presence/absence of marker gene expression suggests that the gene of interest is also present, its presence and expression may need to be confirmed. For example, if the sequence encoding C/EBPβ is inserted within a marker gene sequence, recombinant cells containing sequences encoding human C/EBPβ can be identified by the absence of marker gene function. Alternatively, a marker gene can be placed in tandem with a sequence encoding C/EBPβ under the control of a single promoter. Expression of the marker gene in response to induction or selection usually indicates expression of the tandem gene as well.

Alternatively, host cells which contain the nucleic acid sequence encoding and express C/EBPβ may be identified by a variety of procedures known to those of skill in the art. These procedures include, but are not limited to, DNA-DNA or DNA-RNA hybridizations and protein bioassay or immunoassay techniques which include membrane, solution, or chip-based technologies for the detection and/or quantification of nucleic acid or protein.

A variety of protocols for detecting and measuring the expression of human C/EBPβ, using either polyclonal or monoclonal antibodies specific for the protein known in the art find use in the present invention. Examples include enzyme-linked immunosorbant assay (ELISA), radioimmunoassay (RIA), and fluorescence activated cell sorting (FACS).

A wide variety of labels and conjugation techniques are known by those skilled in the art and may be used in various nucleic acid and amino acid assays. Means for producing labeled hybridization or PCR probes for detecting sequences related to polynucleotides encoding C/EBPβ include oligo-labeling, nick translation, end-labeling or PCR amplification using a labeled nucleotide. Alternatively, the sequences encoding C/EBPβ or any portions thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kit. Suitable reporter molecules or labels, which may be used, include radionuclides, enzymes, fluorescent, chemiluminescent, or chromogenic agents as well as substrates, cofactors, inhibitors, magnetic particles, and the like.

Host cells transformed with nucleotide sequences encoding C/EBPβ may be cultured under conditions suitable for the expression and recovery of the protein from cell culture. The protein produced by a recombinant cell may be secreted or contained intracellularly depending on the sequence and/or the vector used. As will be understood by those of skill in the art, expression vectors containing polynucleotides which encode C/EBPβ may be designed to contain signal sequences which direct secretion of portions of C/EBPβ through a prokaryotic or eukaryotic cell membrane. Other recombinant constructions may be used to join sequences encoding C/EBPβ to nucleotide sequences encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (Invitrogen, San Diego, Calif.) between the purification domain and human C/EBPβ may be used to facilitate purification.

In addition to recombinant production, fragments of C/EBPβ may be produced by direct peptide synthesis using solid-phase techniques that are well known in the art (See e.g., Merrifield, J. Am. Chem. Soc., 85:2149-2154 [1963]). Protein synthesis may be performed using manual techniques or by automation. Automated synthesis may be achieved by any commercially available synthesizer suitable for the project. In addition, various fragments of C/EBPβ may be chemically synthesized separately and combined using chemical methods to produce the full length molecule.

DETAILED DESCRIPTION OF THE PRESENT INVENTION

The present invention relates generally to the treatment and prevention of diseases characterized by excess cell proliferation and/or activation. In particular, the present invention provides compositions and methods to suppress the activation and/or proliferation of various cells. In preferred embodiments, the present invention provides compositions and methods to suppress the activation and/or proliferation of mesenchymally derived cells (including, but not limited to hepatic stellate cells), as well as cells with abnormal growth characteristics. In particularly preferred embodiments, the present invention provides compositions and methods to inhibit or eliminate fibrosis. In alternative preferred embodiments, the present invention provides compositions and methods to induce fibrosis.

Phosphorylation of C/EBPβ on Thr$^{217}$ is Required for Hepatic Cell Survival

To test whether collagen type I matrix induces C/EBPβ phosphorylation, primary mouse hepatic stellate cells were labeled for 12 hr with $^{32}$P-orthophosphate and cultured either on EHS (Matrigel) (quiescent cells) or collagen type I (activated cells), as described in Example 5. Phosphopeptide mapping of immunoprecipitated C/EBPβ showed that the collagen type I matrix induced a site-specific phosphorylation of endogenous C/EBPβ on Thr$^{217}$, a p90RSK phosphoacceptor domain (Buck et al., [1999], supra), and on another, yet unidentified, phosphoacceptor site (See, FIG. 1, Panels A and B).

C/EBPβ phosphorylation was negligible in quiescent mouse stellate cells cultured on an EHS matrix (See, FIG. 1, Panel A).

Next, the functional relevance of C/EBPβ and its phosphorylation on $Thr^{217}$ were ascertained. Activated primary mouse hepatic stellate cells were transfected with either wild-type (sense) or antisense C/EBPβ expressing vectors. Stellate cells expressing C/EBPβ antisense, but not sense, RNA (Buck et al., EMBO J., 13:851-860 [1994]) lacked detectable C/EBPβ protein and did not proliferate, as detected by the expression of proliferating cell nuclear antigen (Bravo et al., Nature 326:515-517 [1987]; Buck et al., [1994], supra; and Buck et al., [1999], supra). However, these cells displayed increased annexin-V binding to phosphatidylserine in plasma membranes, an early indicator of apoptosis (Rudel and Bokoch, supra) (See, FIG. 1, Panel C).

To determine whether phosphorylation of mouse C/EBPβ on $Thr^{217}$ (i.e., C/EBPβ-$PThr^{217}$) is critical for survival, mouse stellate cells were transfected with a MSV expression vector for the nonphosphorylatable C/EBPβ-$Ala^{217}$ mutant. Transfected cells were identified by the expression of the co-transfected CMV-GFP (green fluorescent protein) using triple-channel fluorescence microscopy, as described in Example 2. Cells expressing the C/EBPβ-$Ala^{217}$ mutant (Buck et al., [1999], supra) did not proliferate and became apoptotic as determined by live microscopy (See, FIG. 1, Panel C) and cell sorting analysis (FACS) for the transfection indicator green fluorescent protein and annexin-V. Cell death was confirmed by nuclear staining with Hoechst 33342. Co-expression of RSK was unable to rescue apoptosis induced by C/EBPβ-$Ala^{217}$ (See, FIG. 1, Panel C).

Conversely, induction of apoptosis in hepatic stellate cells by blocking activation of the antiapoptotic NFκB (Beg and Baltimore, Science 274:782-784 [1996]; and Wang et al., Science 274:784-787 [1996]) or RSK (Buck et al., [1999], supra; Bonni et al., supra; Bhatt and Ferrell, supra; Gross et al., supra; and Sassone-Corsi et al., supra) activity was rescued by the phosphorylation mimic C/EBPβ-$Glu^{217}$ mutant (Buck et al., [1999], supra) (See, FIG. 1, Panel D).

MEK kinase 1 (MEKK1) activates NFRB through phosphorylation of IκB kinases α and β leading to phosphorylation of IκB (Lee et al., Cell 88:213-222 [1997]), which undergoes rapid proteolysis via the ubiquitin-proteasome pathway (Chen et al., Genes Dev., 9:1586-1597 [1995a]). Therefore, stellate cells were transfected with expression vectors for the dominant negative mutants for MEKK1, IκBα and RSK, or treated cells with lactacystin (a proteasome inhibitor) to induce apoptosis. In each case, stellate cell apoptosis was partially inhibited by the C/EBPβ-$Glu^{217}$ mutant (See, FIG. 1, Panel D), indicating that in the absence of active NFκB or RSK, phosphorylation of C/EBPβ on $Thr^{217}$ promotes cell survival. In addition, expression of C/EBPβ-$Glu^{217}$ prevented stellate cell apoptosis induced by the RSK mutant or FAS ligand, but not by serum deprivation (See, FIG. 1, Panel E), indicating that it has a selective effect on caspase activation pathways.

Figure 2:
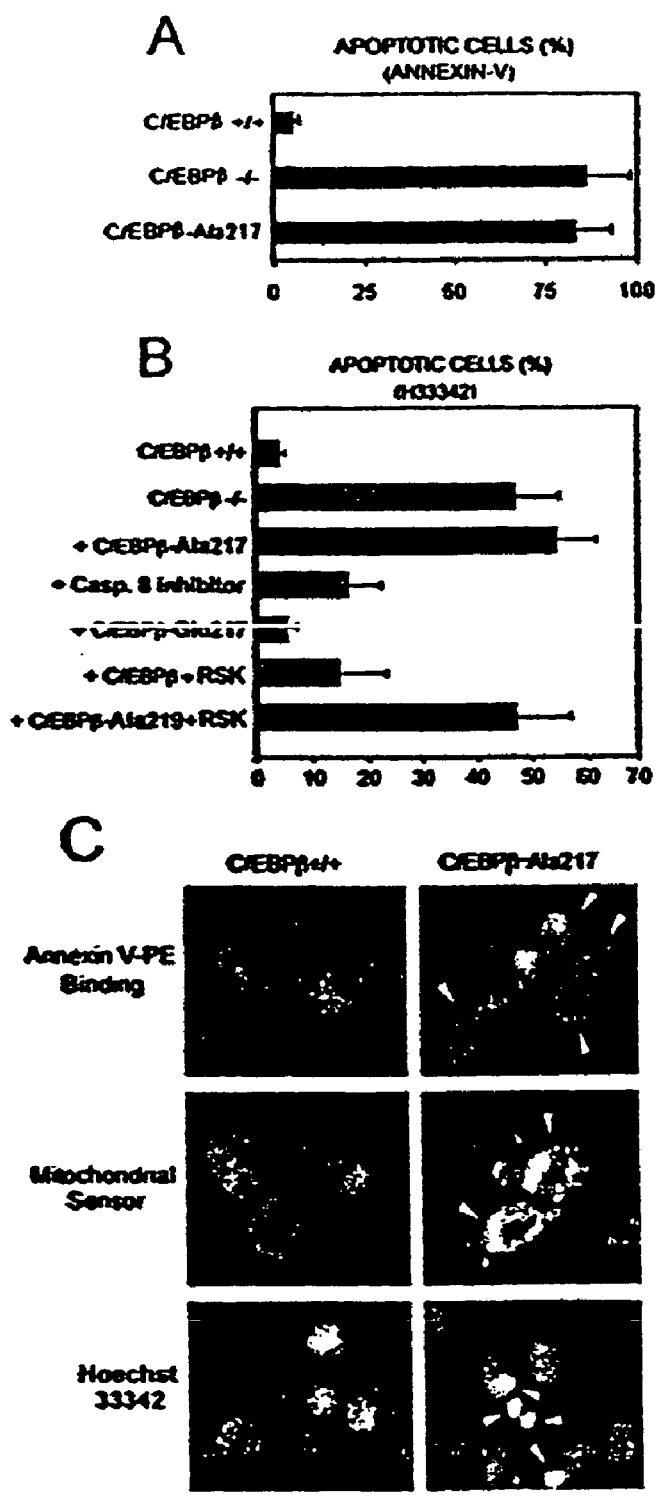
FIG. 2 provides results showing increased apoptosis in hepatic stellate cells from C/EBPβ$^{-/-}$ and C/EBPβ-Ala$^{217}$ transgenic mice. Panel A shows results from primary stellate cells isolated from C/EBPβ$^{+/+}$, C/EBPβ$^{-/-}$ and C/EBPβ-Ala$^{217}$ mice and cultured on a collagen type I matrix. Six hours after cultivation, an annexin-V-PE binding assay was performed ($P<0.05$ for C/EBPβ$^{-/-}$ and C/EBPβ-Ala$^{217}$). Panel B shows results for nuclear staining of cells described above (Panel A) with Hoechst 33342. In addition, cells from C/EBPβ-Ala$^{217}$ mice were treated with a cell permeant caspase 8 inhibitor (IETD) (1.05 nM) or transfected with MSV-C/EBPβ, C/EBPβ-Ala$^{217}$, C/EBPβ-Ala$^{210}$, or RSK (1 μg each), as indicated ($P<0.05$ for C/EBPβ$^{-/-}$, C/EBPβ-Ala$^{217}$, C/EBPβ-Ala$^{217}$+RSK+C/EBPβ-Ala$^{210}$. Panel C provides data showing representative examples of annexin-V and mitochondrial sensor and Hoechst 33342 assays in primary stellate cells described above for Panels A and B. As indicated, stellate cells from C/EBPβ-Ala$^{217}$ mice displayed increased annexin-V-PE binding and altered mitochondrial sensor assay results, and loss of nuclear integrity. Apoptotic cells are indicated with arrowheads.

Hepatic Stellate Cells From C/EBPβ$^{-/-}$ and C/EPBβ-$Ala^{217}$ Transgenic Mice Display Increased Apoptosis Following $CCl_4$ Treatment To ascertain the functional relevance of mouse C/EBPβ, and its phosphorylation on $Thr^{217}$, the survival of primary hepatic stellate cells isolated from mice with a targeted deletion of C/EBPβ (Buck et al., [1999], supra) was analyzed. C/EBPβ$^{-/-}$, but not C/EBPβ$^{+/+}$, cells became rapidly apoptotic on collagen type I as determined by annexin-V binding using live microscopy (FIG. 2, Panel A). To study the role of C/EBPβ-$PThr^{217}$ on stellate cell survival, mice expressing a nonphosphorylatable dominant negative C/EBPβ-$Ala^{217}$ mutant transgene were developed. Although C/EBPβ-$Ala^{217}$ transgenic mice were developmentally normal, hepatic stellate cells isolated from these animals consistently failed to survive when activated by collagen type I (See, FIG. 2). The apoptotic phenotype of stellate cells isolated from C/EBPβ$^{-/-}$ and C/EBPβ-$Ala^{217}$ transgenic mice was corroborated by using a mitochondrial sensor assay (Green and Reed, Science 281:1309-1312 [1998]), which showed that they had an altered mitochondrial membrane permeability (FIG. 2, Panel C), and by their pycnotic nuclear staining pattern (See, FIG. 2, Panels B and C). Apoptosis of C/EBPβ-$Ala^{217}$ stellate cells was blocked by a cell permeant caspase 8 inhibitor (IETD) or by expression of C/EBPβ-$Glu^{217}$ (See, FIG. 2, Panel B).

Next, the determination was made whether hepatic stellate cell activation is stimulated by $CCl_4$, a hepatotoxin that induces hepatic oxidative stress and liver fibrogenesis (Houglum et al., supra; and Chojkier, supra). Hepatic stellate cells, identified by their glial fibrillary acidic protein and vimentin staining (Ankoma-Sey and Friedman, supra), were induced to proliferate in the liver of C/EBPβ$^{+/+}$ mice following treatment with a single dose of $CCl_4$. In contrast, $CCl_4$ induced stellate cell apoptosis in the livers of C/EBPβ$^{-/-}$ and C/EBPβ-$Ala^{217}$ transgenic mice (See, FIG. 3), as determined by the presence of an active effector caspase 3. Because activated p90RSK is able to phosphorylate C/EBPβ on $Thr^{217}$ (Buck et al., [1999], supra) in vitro, the determination of whether RSK was associated with C/EBPβ in these animals was made.

Figure 3:
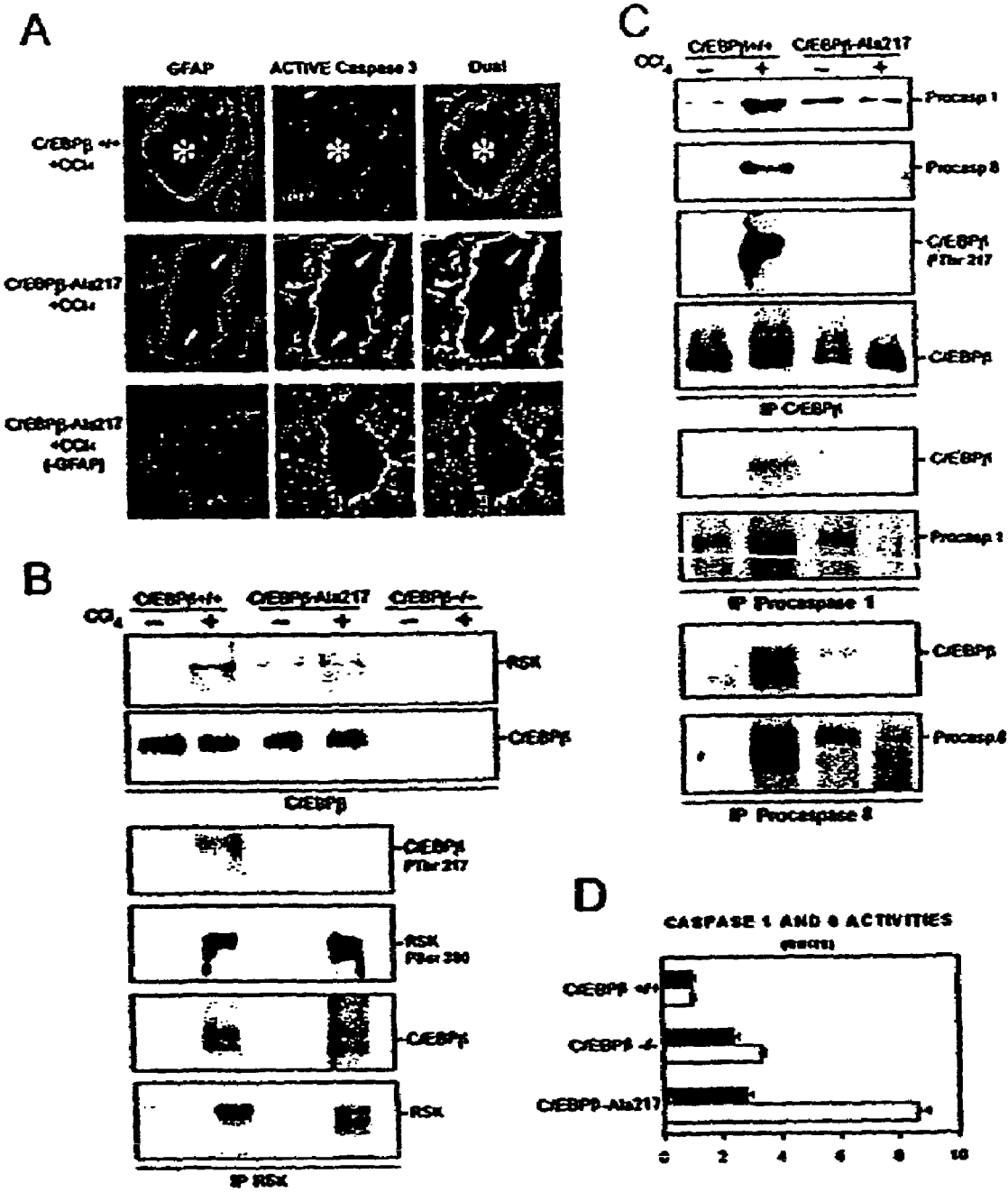
FIG. 3 provides results showing that C/EBPβ-Thr$^{217}$ associates with procaspases 1 and 8. Panel A provides results showing that stellate cells, identified by confocal microscopy with glial fibrillary acidic protein (GFAP) displayed active caspase 3 in livers from C/EBPβ-Ala$^{217}$, but not C/EBPβ$^{+/+}$, mice 12 h after treatment with CCl$_4$. Colocalization of GFAP and active caspase 3 is indicated by the arrows. Asterisks indicate sinusoidal lumens in C/EBPβ$^{+/+}$ mice. Only background (i.e., red) staining was observed when the GFAP antibody was omitted. Mineral oil induced no changes. Panel B provides data showing increased p90RSK association with C/EBPβ. These results are for an RSK immunoblot performed on C/EBPβ$^{+/+}$, C/EBPβ-Ala$^{217}$, and C/EBPβ$^{-/-}$ (control) immunoprecipitates from protein lysates (500 μg) from samples described for Panel A. RSK association was increased in stellate cells isolated from C/EBPβ$^{+/+}$ and C/EBPβ-Ala$^{217}$ mice treated with CCl$_4$. C/EBPβ-PThr$^{217}$ association with RSK and active RSK-PSer$^{380}$ (in RSK immunoprecipitates) was increased in C/EBPβ$^{+/+}$ and C/EBPβ-Ala$^{217}$ mice treated with CCl$_4$. Panel C provides results showing that association of procaspases 1 and 8 with C/EBPβ and C/EBPβ-PThr$^{217}$ (in C/EBPβ immunoprecipitates) was increased in C/EBPβ$^{+/+}$ mice treated with CCl$_4$. Reciprocal immunoprecipitates confirmed these associations. Panel D provides results showing that the activities of caspases 1 and 8 are increased in stellate cell lysates from C/EBPβ$^{-/-}$ and C/EBPβ-Ala$^{217}$, but not C/EBPβ$^{+/+}$ mice treated with CCl$_4$, as described above for Panel A. Caspase activity was determined by the release of the chromogenic substrate using 5×10$^6$ cells per point. The values are presented as the mean±one half of the range of duplicates for caspase 1 (empty bars) and caspase 8 (closed bars) activities in CCl$_4$-treated animals (corrected for the basal activities in untreated animals).

$CCl_4$ Treatment Induces Activated RSK, C/EBP-β$Thr^{217}$ and its Association with Procaspases 1 and 8 in Hepatic Stellate Cells of Normal Mice Because activated p90RSK is able to phosphorylate C/EBPβ on $Thr^{217}$ in vitro (FIG. 1, Panel B) (Buck et al., [1999] supra), analyses were conducted to determine whether RSK was associated with C/EBPβ. The results indicated that there was an increased RSK associated with C/EBPβ in stellate cells from C/EBPβ$^{+/+}$ and C/EBPβ-$Ala^{217}$ transgenic mice treated with $CCl_4$ (FIG. 3, Panel B). Conversely, when RSK was immunoprecipitated with specific antibodies, the level of co-precipitated C/EBPβ was consistently increased in C/EBPβ$^{+/+}$ and C/EBPβ-$Ala^{217}$ transgenic mice treated with $CCl_4$ (FIG. 3, Panel B). $CCl_4$ increased the expression and the activity of RSK, as determined with a specific antibody against RSK-$PSer^{380}$ (FIG. 3, Panel B). In C/EBPβ$^{+/+}$ mice, $CCl_4$ also induced phosphorylation of endogenous C/EBPβ on $Thr^{217}$, as detected with a newly developed affinity purified antibody specific for this phosphorylated epitope (FIG. 3, Panel B). These findings indicate that phosphorylation of C/EBPβ on $Thr^{217}$ by RSK is indispensable for stellate cell survival. Given that the $Thr^{217}$ phosphoacceptor in C/EBPβ contains a $KT^{217}VVD$ sequence (identical to human C/EBPβ) that upon phosphorylation by RSK can be functionally mimicked by the C/EBPβ-$Glu^{217}$ sequence $KE^{217}VD$ (Buck et al., [1999], supra), and that the latter is similar to a XEXD box found in inhibitors and substrates of caspases (Thornberry et al., J. Biol. Chem., 272:17907-17911 [1997]; and Blanchard et al., J. Mol. Biol., 302:9-16 [2000]), experiments were conducted to investigate whether C/EBPβ-$PThr^{217}$ associates with procaspases. The results indicated that procaspases 1 and 8 (FIG. 3, Panel C), but not procaspases 3, 7 or 9 (data not shown), in C/EBPβ immunoprecipitates (containing C/EBPβ-$PThr^{217}$) of stellate cells isolated from C/EBPβ$^{+/+}$ mice, following treatment with $CCl_4$. The levels of procaspases 1 and 8 from C/EBPβ$^{+/+}$ mice treated with $CCl_4$ were increased, and their immunoprecipitates contained C/EBPβ (FIG. 3, Panel C). The association of C/EBPβ with procaspases 1 and 8 remained baseline in cells of C/EBPβ-Ala$^{217}$ transgenic mice treated with CCl$_4$ (FIG. 3, Panel C) and in cells of C/EBPβ$^{+/+}$ mice treated with control mineral oil vehicle. In addition, the enzymatic activities of caspases 1 and 8 (FIG. 3, Panel D), and that of the effector caspase 3 (FIG. 3, Panel A), were increased in stellate cells of C/EBPβ$^{-/-}$ or C/EBPβ-Ala$^{217}$, but not of C/EBPβ$^{+/+}$, mice following treatment with CCl$_4$. These results indicate that phosphorylation of C/EBPβ on Thr$^{217}$ with the creation of a functional XEXD box (or expression of the phosphorylation mimic C/EBPβ-Glu$^{217}$ mutant) is required for C/EBPβ to associate with procaspases 1 and 8. These data also indicate that phosphorylation of C/EBPβ may prevent processing and activation of procaspases 1 and 8, since neither K-Phospho-T$^{217}$VD nor KE$^{217}$VD are the preferred substrates for caspases 1 or 8 (Wilson et al., Nature 370:270-275 [1994]; Margolin et al., J. Biol. Chem., 272:7223-7228 [1997]; Earnshaw et al., Ann. Rev. Biochem., 68:383-424 [1999]), and C/EBPβ does not appear to be cleaved by caspase 1 or 8 (data not shown). In addition, apoptosis of C/EBPβ-Ala$^{217}$ cells was rescued by expressing RSK and C/EBPβ, but not RSK and C/EBPβ-Ala$^{219}$, containing a mutation of the critical P1 Asp residue of the XEXD box (Thornberry and Lazebnik, supra) (See, FIG. 2, Panel B).

Figure 4:
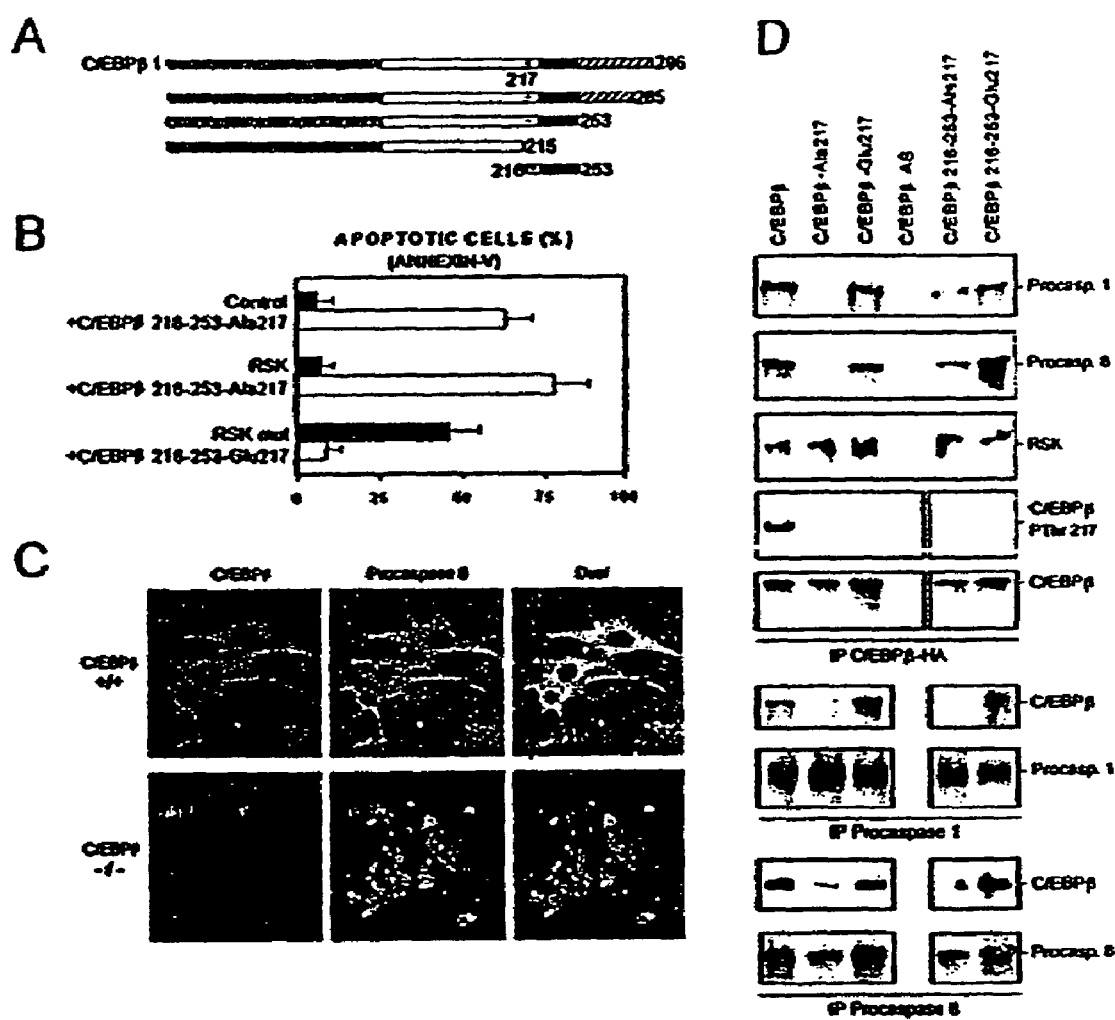
FIG. 4 provides results showing that C/EBPβ PThr$^{217}$ associates with procaspases 1 and 8, and inhibits their activation. Panel A provides schematic representations of C/EBPβ peptides. The activation (dotted bars), DNA binding (solid bars) and dimerization (hatched bars) domains are shown. Panel B shows results for stellate cells transfected with the indicated plasmids together with CMV-GFP (0.3 μg each) and cultured on a collagen type I matrix ($P<0.05$ for C/EBPβ 216-256-Ala$^{217}$ and RSK mutant). Panel C provides results showing that C/EBPβ and procaspase 8 were detected in activated stellate cells isolated from C/EBPβ+/+ mice by confocal microscopy using specific antibodies (Santa Cruz Biotechnology). Control C/EBPβ−/− stellate cells were negative for C/EBPβ, positive for procaspase 8, and apoptotic. Panel D provides immunoblot results for MSV vectors expressing C/EBPβ-HA (hemagglutinin protein) peptides (0.3 μg) transfected into activated stellate cells. The expressed peptides were immunoprecipitated with anti-HA antibodies. C/EBPβ-PThr$^{217}$ was detected using a specific antibody, only in cells expressing wild-type C/EBPβ. Immunoblots showed a greater association of procaspases 1 and 8 with C/EBPβ-PThr$^{217}$ and C/EBPβ peptides containing Glu$^{217}$ than C/EBPβ peptides containing Ala$^{217}$. RSK was associated with all C/EBPβ peptides. Neither C/EBPβ nor procaspases 1 and 8 were detected in C/EBPβ immunoprecipitates from cells expressing C/EBPβ AS. Reciprocal immunoprecipitations of procaspases and RSK confirmed these associations.

C/EBPβ-PThr$^{217}$, Lacking the Activation and Dimerization Domains is Sufficient for Stellate Cell Survival on Collagen Type I Expression of C/EBPβ 1-253, with a deletion of the dimerization domain (Descombes et al., [1990], supra) (FIG. 4, Panel A) and containing Thr$^{217}$ or Glu$^{217}$, but not Ala$^{217}$, was found to be compatible with cell survival. C/EBPβ 1-215 lacking the DNA binding and dimerization domains and the KT$^{217}$VD phosphoacceptor (FIG. 4, Panel A) had no effect on cell survival. In contrast, C/EBPβ 216-253-Ala$^{217}$, but not Glu$^{217}$, lacking the activation and dimerization domains (FIG. 4, Panel A), induced apoptosis in control cells even when wild type RSK was expressed (FIG. 4, Panel B). In addition, expression of C/EBPβ216-253-Glu$^{217}$ was sufficient to rescue cells from apoptosis induced by a catalytically inactive RSK mutant (RSK N'C'), (Nakajima et al., Cell 86:465-474 [1996]) (FIG. 4, Panel B). In agreement with previous reports (Mao et al., J. Biol. Chem., 273:23621-23624 [1998]; and Ritter et al., Eur. J. Cell Biol., 79:358-364 [2000]), procaspases 1 and 8 were detected predominantly in the cytoplasm of activated stellate cells, which colocalized with C/EBPβ (FIG. 4, Panel C).

Immunoprecipitation of C/EBPβ-HA and C/EBPβ216-253-HA from stellate cells showed that both the P-Thr$^{217}$ and the phosphorylation mimic Glu$^{217}$, co-precipitated with procaspases 1 and 8 more efficiently than the nonphosphorylatable Ala$^{217}$ (FIG. 4, Panel D). Similar results were obtained when the reciprocal immunoprecipitation was performed with procaspases 1 and 8 antibodies. Therefore, neither the activation nor the dimerization domain of C/EBPβ is required for stellate cell survival.

Figure 5:
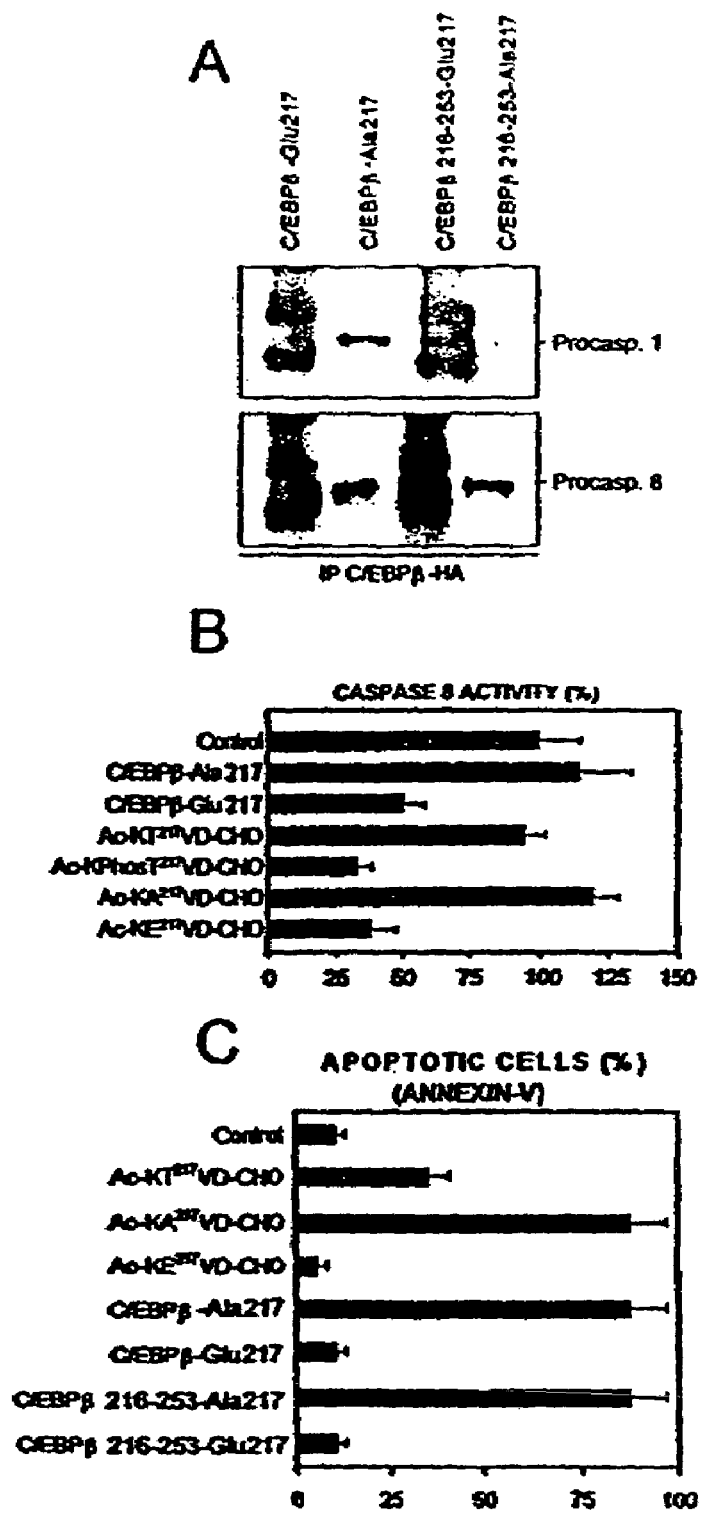
FIG. 5 provides results showing the direct association of C/EBPβ-Glu$^{217}$ with procaspases 1 and 8. Panel A provides an immunoblot showing results indicating that purified recombinant C/EBPβ-Glu$^{217}$ and C/EBPβ 216-253-Glu$^{217}$ (200 μM) co-immunoprecipitated purified recombinant procaspases 1 (0.6 U) and 8 (0.12 μg) 7- and 12-fold more than C/EBPβ-HA-Ala$^{217}$ and C/EBPβ 216-253-HA-Ala$^{217}$, as quantitated by densitometry. Panel B provides results showing that purified C/EBPβ-HA-Glu$^{217}$ and C/EBPβ 216-219-PThr$^{217}$ and -Glu$^{217}$ synthetic tetrapeptides inhibited the in vitro self-activation of caspases 1 and 8. Enzyme activity was measured in the absence (control) or presence of C/EBPβ peptides (200 μM) for 2 h, using a procaspases 1 (1U) (not shown) and 8 (0.2 μg) activity assay. Values are presented as the mean±one half the range of duplicates. Panel C provides results for cells cultured on a collagen type I matrix and incubated with the indicated cell permeant, purified synthetic N-acetyl, C-aldehyde C/EBPβ tetra-peptides (10 μM) or with recombinant C/EBPβ-HA peptides as indicated, together with the Chariot reagent (Active Motif) for 4 h. Control cells were incubated without peptides (P<0.05 for all peptides containing Ala$^{217}$).

C/EBPβ-PThr$^{217}$ Peptides Associate with Procaspases 1 and 8 and Inhibit Their Activation In addition, the effect of purified recombinant C/EBPβ peptides on the self-activation of recombinant caspases 1 and 8 in vitro was determined. Consistent with the in vivo results described above, C/EBPβ-HA-Glu$^{217}$ and C/EBPβ216-253-HA-Glu$^{217}$ peptides directly associated with caspases 1 and 8 about 7- and 12-fold more effectively than C/EBPβ-HA-Ala$^{217}$ (FIG. 5, Panel A). Moreover, recombinant C/EBPβ-Glu$^{217}$, and the synthetic tetrapeptides Ac-K-Phospho-T$^{217}$VD-CHO and Ac-KEE$^{217}$VD-CHO directly inhibited the in vitro self-activation of recombinant caspases 1 and 8 (FIG. 5, Panel B). The dominant negative cell permeant peptides Ac-KA$^{217}$VD-CHO consistently induced apoptosis to a degree comparable to C/EBPβ-Ala$^{217}$ and C/EBPβ 216-253-Ala$^{217}$ (FIG. 5, Panel C). In contrast, wild type and Glu$^{217}$ C/EBPβ peptides did not induce apoptosis (FIG. 5, Panel C).

Figure 6:
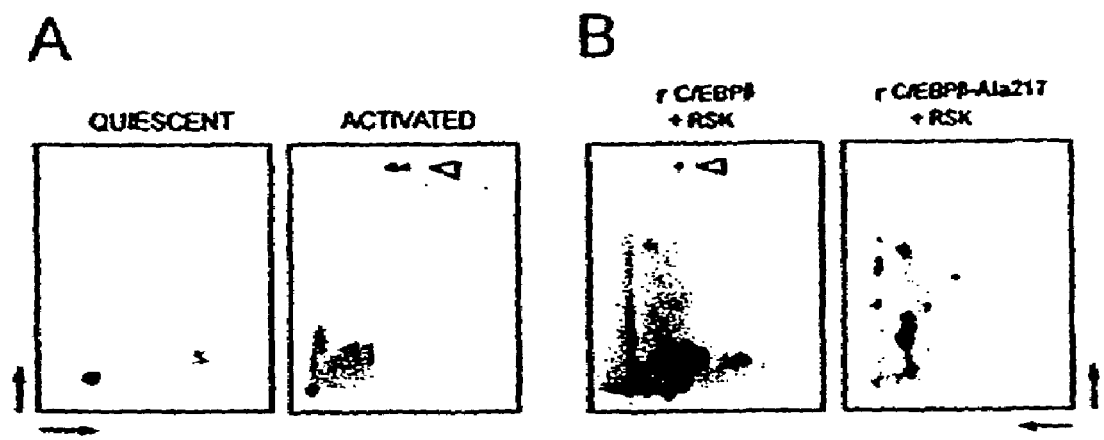
FIG. 6 provides results showing endogenous C/EBPβ is phosphorylated on Ser$^{105}$ in rat stellate cells. Panel A provides phosphopeptide maps performed in day-4 quiescent and activated primary rat hepatic stellate cells cultured as described above for FIG. 1. These results show that collagen type I induces phosphorylation of rat C/EBPβ on Ser$^{105}$. The arrow indicates the peptide containing Phospho-Ser$^{105}$ in activated cells. Panel B provides phosphopeptide maps of in vitro labelled rC/EBPβ. Active p90RSK phosphorylated rC/EBPβ in vitro, but not rC/EBPβ-Ala$^{105}$ on Ser$^{105}$ (indicated by arrowheads).

Rat C/EBPβ-PSer$^{105}$, the Functional Homologue of Mouse C/EBPβ-PThr$^{217}$, Associates with Procaspases 1 and 8 In Vivo and In Vitro and Inhibit their Activation Although the C/EBPβ-Thr$^{217}$ phosphoacceptor is highly conserved through evolution, rat (r) C/EBPβ has evolved with a double change, lacking the Thr$^{217}$ phosphoacceptor but having a compensatory Ser$^{105}$ RSK phosphoacceptor (Descombes et al., supra). The presence of C/EBPβ-PThr$^{217}$ or rC/EBPβ-PSer$^{105}$ in mouse and rat cells, respectively, is critical for the induction of hepatocyte proliferation by TGFα (Buck et al., [1999], supra). Collagen type I induced phosphorylation of endogenous rC/EBPβ on Ser$^{105}$ and on other sites in proliferating rat hepatic stellate cells (FIG. 6, Panel A). rC/EBPβ phosphorylation was negligible in quiescent rat stellate cells cultured on an EHS matrix (FIG. 6, Panel A). The phosphopeptide induced by collagen type I had the same mobility as the previously described PSer$^{105}$ peptide, a p90RSK phosphoacceptor (Trautwein et al., Nature 364:544-547 [1993]; Buck et al., [1999], supra). Tryptic phosphopeptide analysis of rC/EBPβ demonstrated that p90RSK can phosphorylate C/EBPβ on Ser$^{105}$ (FIG. 6, Panel B), as well as other sites; phosphorylation of the rC/EBPβ-Ala$^{105}$ mutant did not yield this phosphopeptide (FIG. 6, Panel B), suggesting that this peptide contains Ser$^{105}$. Phosphorylation of endogenous rC/EBPβ on Ser$^{105}$ was confirmed using specific antibodies against this epitope, as described below.

Additional experiments were conducted to determine whether rC/EBPβ-PSer$^{105}$ rescues cells from apoptosis. Stellate cells were induced to develop apoptosis by expressing the dominant negative RSK mutant (Nakajima et al., supra) or by treatment with lactacystin. Expression of the phosphorylation mimic rC/EBPβ-Asp$^{105}$ rescued mouse (FIG. 7, Panel A) and rat (data not shown) stellate cells from apoptosis. The nonphosphorylatable rC/EBPβ-Ala$^{105}$ mutant, like C/EBPβ-Ala$^{217}$, induced apoptosis of stellate cells (data not shown), since neither mutant has a RSK phosphoacceptor site. These results indicate that rC/EBPβ-PSer$^{105}$ (or its phosphorylation mimic rC/EBPβ-Asp$^{105}$) is able to block the apoptotic pathway as effectively as C/EBPβ-PThr$^{217}$ (or its phosphorylation mimic C/EBPβ-Glu$^{217}$) (FIG. 1).

Figure 7:
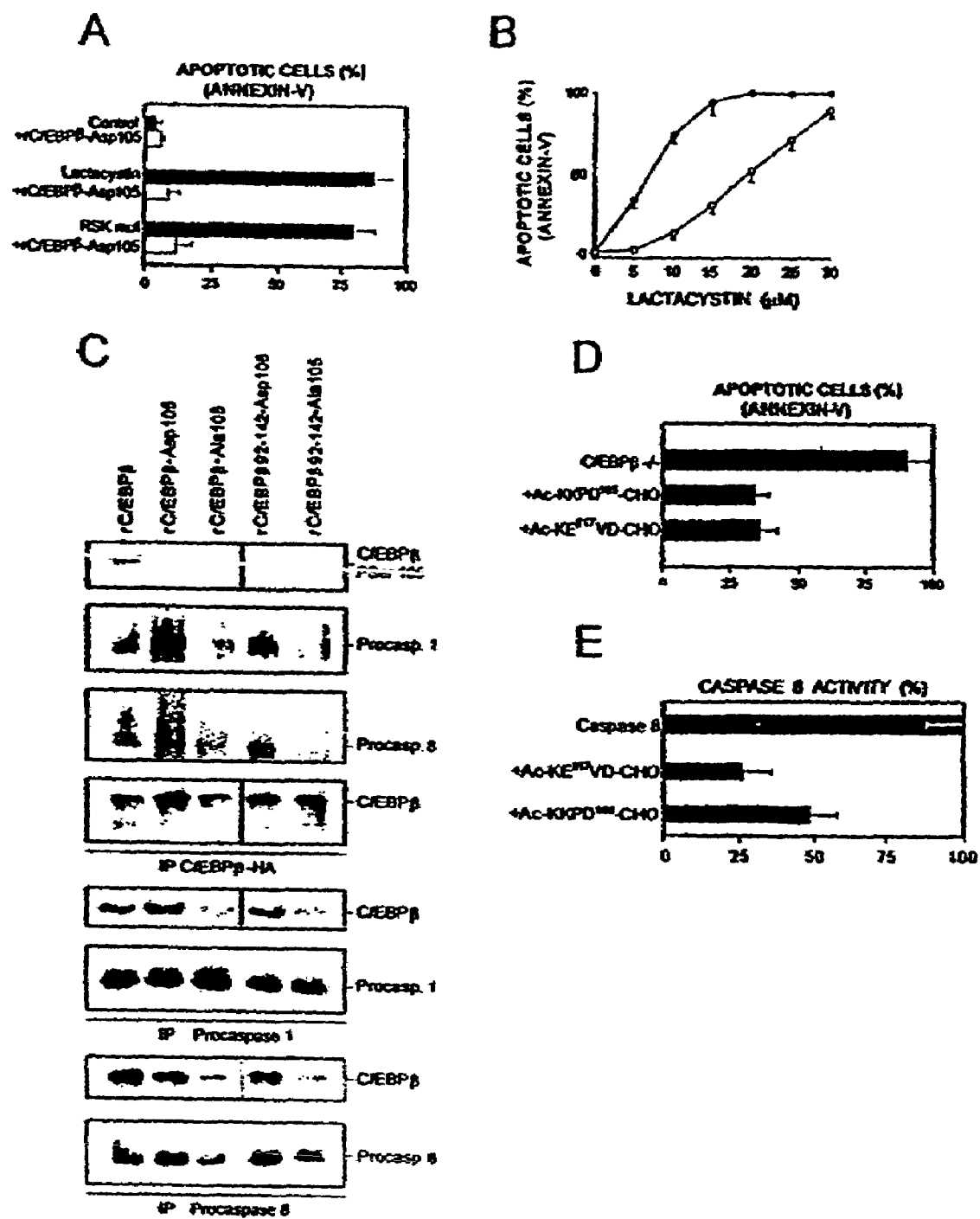
FIG. 7 provides data showing that phosphorylation of rat C/EBPβ on Ser$^{105}$ prevents stellate cell apoptosis. Panel A provides results for mouse stellate cells transfected as described herein (See, FIG. 2), with mutant p90RSK or treated with lactacystin (10 μM) (closed bars), and co-transfected with CMV-rC/EBPβ-Asp$^{105}$ (1 μg each) (open bars) as indicated. Annexin-V-PE binding was determined as described for FIG. 2 (P<0.05 for rC/EBPβ-Asp$^{105}$). Panel B provides results of an annexin-V-PE assay for stellate cells from C/EBPβ+/+ (closed circles) and rC/EBPβ-Asp$^{105}$ transgenic (open circles) mice treated with lactacystin (0-30 μM). The annexin-V-PE assay was performed 6 hours after treatment began (P<0.05 for rC/EBPβ-Asp$^{105}$ transgenic mice for 5-25 μM lactacystin). Panel C provides results for rC/EBPβ-HA constructs (0.3 μg) transfected into rat stellate cells. The expressed peptides were immunoprecipitated with anti-HA antibodies. Using a specific antibody, rCEBPβ-PSer$^{105}$ was detected only in cells that expressed wild-type rC/EBPβ. An immunoblot for procaspases 1 and 8 showed a greater association with C/EBPβ-PSer$^{105}$ and rC/EBPβ-Asp$^{105}$ than with C/EBPβ-Ala$^{105}$ peptides. Reciprocal immunoprecipitations confirmed these associations. Panel D provides results for stellate cells isolated from C/EBPβ−/− mice incubated with the indicated cell permeant, purified synthetic N-acetyl-C-aldehyde C/EBPβ tetrapeptides (10 μM) for 4 hours together with the Chariot reagent. Control cells were incubated without peptides (P<0.05, for both tetrapeptides). Panel E provides results for Ac-KE$^{217}$VD-CHO and Ac-KKPD$^{105}$-CHO synthetic tetrapeptides (200 μM). These results indicated that these tetrapeptides inhibited the in vitro self-activation of caspase 8. Enzyme activity was measured using a colorimetric substrate as described in the Examples. Baseline caspase 8 activity was 4.7 U (100%). Values are presented as the mean±one half of the range of duplicates.

Because the rC/EBPβ-Asp$^{105}$ mutant behaves as a phosphorylation mimic of rC/EBPβ-PSer$^{105}$ in rescuing cells from apoptosis (FIG. 7, Panel A), mice expressing a rC/EBPβ-Asp$^{105}$ transgene were developed. Although rC/EBPβ-Asp$^{105}$ transgenic mice were developmentally normal, stellate cells isolated from these animals were resistant to the induction of apoptosis by lactacystin (FIG. 7, Panel B). Lactacystin induced a significant and rapid increase in C/EBPβ +/+ stellate cell apoptosis (FIG. 7, Panel B). rC/EBPβ-HA and rC/EBPβ 92-142-HA showed that P-Ser$^{105}$ and the phosphorylation mimic Asp$^{105}$ coimmunoprecipitated from rat stellate cells with procaspases 1 and 8 more efficiently than the nonphosphorylatable Ala$^{105}$ (FIG. 7, Panel C). rC/EBPβ-Asp$^{105}$ was not associated with active caspases 1 or 8 (data not shown). Similar to the effects of rC/EBPβ-PSer$^{105}$ and rC/EBPβ-Asp$^{105}$ on cell survival, treatment of freshly isolated stellate cells from C/EBPβ −/− mice with cell permeant tetrapeptides that include the phosphorylation mimic domain of C/EBPβ (Ac-KE$^{217}$VD-CHO) or rC/EBPβ (Ac-KKPD$^{105}$-

CHO), rescued these cells from apoptosis following their activation by collagen type I (FIG. 7, Panel D). In addition, it was determined that the synthetic tetrapeptide Ac-KKPD$^{105}$-CHO, like Ac-KE$^{217}$VD-CHO, inhibited the in vitro self-activation of recombinant caspase 8 (FIG. 7, Panel E).

The results obtained during the development of the present invention indicate that the present invention provides a novel means for cell survival. However, an understanding of the mechanisms involved is not necessary in order to use the present invention. Nonetheless, signaling pathways that activate RSK result in the phosphorylation of C/EBPβ on Thr$^{217}$. C/EBPβ-PThr$^{217}$ associates with the initiator procaspases 1 and 8 and inhibits their processing, which blocks the apoptotic cascade and allows the survival of hepatic stellate cell upon activation. This is believed to be the first demonstration that phosphorylation of a transcription factor by the ERK/MAPK/RSK pathway stimulates its association with procaspases, preventing their activation. Phosphorylation of C/EBPβ on Thr$^{217}$ with the creation of a pseudo XEXD box (Thornberry et al., [1997], supra; and Blanchard et al., supra) provides the most likely explanation of this newly described anti-apoptotic role of this transcription factor. Although C/EBPβ Thr$^{217}$ associated with the initiator procaspases 1 and 8 (inhibiting their processing and activation), but not with the effector procaspases 3, 7 or 9 (Earnshaw et al., supra; Thornberry and Lazebnik, supra; and Ashkenazi and Dixit, supra), it effectively blocked the apoptotic cascade, as indicated by the lack of active caspase 3 in hepatic stellate cells from C/EBPβ$^{+/+}$, but not from the nonphosphorylatable dominant negative C/EBPβ-Ala$^{217}$ transgenic, mice. Moreover, the phosphorylation mimic C/EBPβ-Glu$^{217}$ mutant rescued activated stellate cells from apoptosis induced either by expressing MEKK1, IκBα or RSK dominant negative mutants or by treating the cells with the proteasome inhibitor lactacystin (Chen et al., Nature 374:386-388 [1995b]; Lee et al., [1997], supra; and Nakajima et al., supra).

Neither the activation nor dimerization domains of C/EBPβ are indispensable for associating with procaspases 1 and 8 and inhibiting their processing. More importantly, the mouse Thr$^{217}$ phosphoacceptor is virtually identical in bovine and human C/EBPβ (Akira et al., supra; Cao et al., supra; and Yamaoka et al., supra). C/EBPβ-PThr$^{217}$ is mimicked by C/EBPβ-Glu$^{217}$ (KE$^{217}$VD) (Buck et al., [1999] supra) and therefore, conforms to the current knowledge about the structural requirements for caspase inhibitory tetrapeptides. These tetrapeptides require an aspartic acid (D) residue at the P1 position (Thornberry and Lazebnik, 1998), which is also present in C/EBPβ at amino acid D$^{219}$ (Cao et al., supra; and Buck et al., [1999], supra).

Using a positional scanning substrate library, Thornberry and coworkers (Thornberry et al., J. Biol. Chem., [1997]) have shown that although the optimal sequence for caspase 8 is I/L/V (P4 position) EXD, I, V, W, T, P and D are also acceptable at the P4 position, by virtue of being downstream cleavage sites in the apoptotic cascade. These findings have been recently corroborated by crystallography (Blanchard et al., supra). Group III caspases (including caspase 8) have a preference for small hydrophobic residues at P4, such as D used in these studies (Blanchard et al., supra), which has a comparable hydrophobicity to the K$^{216}$ in C/EBPβ (Boyle et al., Meth. Enzymol., 201:110-149 [1991]). In addition, these authors argue that subsite S3 of caspase 8, which interacts with position P3 (but not with P4) of the tetrapeptide, is crucial for determining the specificity, and that the original classification of caspases need to be revised, especially for caspase 8 (Blanchard et al., supra). Similarly to the selective effects of C/EBPβ PThr$^{217}$ shown herein, CrmA inhibits procaspases 1 and 8 selectively ($K_i$=0.01 and 0.95 nM, respectively) compared to procaspases 3, 6 and 7 (Zhou et al., J. Biol. Chem., 272:7797-7800 [1997]). However, other investigators have suggested that CrmA also inhibits caspases 4, 5, 9 and 10 (Garcia-Calvo et al., J. Biol. Chem., 273:32608-32613 [1998]). In addition, the baculovirus p35 is a potent, albeit less selective, inhibitor of procaspases 1, 3, 6, 8, and 10 ($K_i$=0.1 nM) (Andrade et al., Immunity 8:451-460 [1998]). Moreover, DEVD-CHO, which effectively inhibits procaspases 1 and 8 ($K_i$=17 and 12 nM) (Earnshaw et al., supra), is an equally potent inhibitor of caspase 8 as its classical inhibitor IETD (Blanchard et al., supra).

Additional support for the present invention is provided by the experimental data obtained during the development of the present invention and discussed herein. As indicated herein, the sequence KPhospho-T$^{217}$VD (or KE$^{217}$VD) within C/EBPβ is effective in associating with procaspases 1 and 8 and blocking their activation. Activation of hepatic stellate cells has been induced by treating animals with the hepatotoxin CCl$_4$, or by culturing these cells on a collagen type I matrix. The experiments with C/EBPβ -/- cells and with dominant negative Ala$^{217}$ and dominant positive Glu$^{217}$ mutants, including new C/EBPβ-Ala$^{217}$ transgenic mice, strongly support the present invention.

However, rat C/EBPβ contains a double mutation (mouse Thr-217->rat Ala-217 and mouse Ala-104->rat Ser-105) with a creation of a cell growth compensatory Ser105 phosphoacceptor (Buck et al., [1999], supra). Therefore, experiments were conducted in order to determine whether rat C/EBPβ-PSer$^{105}$ could play a comparable role to that of mouse C/EBPβ-PThr$^{217}$ on cell survival. Expression of the phosphorylation mimic rat C/EBPβ-Asp$^{105}$ (Trautwein et al., supra; and Buck et al., [1999], supra) was sufficient to rescue activated stellate from apoptosis induced by expressing a catalytically inactive dominant negative mutant RSK vector (Nakajima et al., supra; and Buck et al., [1999], supra), or by treating the cells with a proteasome inhibitor. Activation of the PKCα (Trautwein et al., supra) or MAPK (Nebreda and Gavin, supra; and Whitmarsh and Davis, [2000] supra) signaling pathways would result in phosphorylation of rC/EBPβ on Ser$^{105}$ (Trautwein et al., supra; and Buck et al., [1999], supra). It was found that the rat C/EBPβ-Ala$^{105}$ mutant behaves as a dominant negative, inducing apoptosis of activated mouse hepatic stellate cells.

The present invention, supported by experiments conducted on hepatic stellate cells are relevant to human diseases such as liver cirrhosis. In addition, it is contemplated that the present invention will find use in treatment of diseases related to tissue repair mechanisms, due to the activation of other mesenchymal cells (including, but not limited to brain, lung and kidney cells). For example, it is contemplated that the present invention will find use in treatment of such diseases as lung fibrosis (e.g., emphysema), brain gliosis (e.g., Alzheimer's disease), and kidney fibrosis (e.g., glomerulonephritis). However, it is not intended that the present invention be so limited. It is further contemplated that the creation of a pseudo XEXD box by phosphorylation, is a highly prevalent biological mechanism maintained through evolution. This is supported by the observation of potential pseudo XEXD boxes upon phosphorylation of threonine (Phospho-TVD, analogous to EVD) in more than 22,000 sites and of serine (EVPhospho-S, analogous to EVD) in more than 27,000 sites in a database containing ~350,000 proteins. Thus, if only 1% of these sequences is phosphorylated in vivo it would generate pseudo XEXD boxes in ~500 proteins.

Therapeutics

As discussed herein, it is contemplated that the C/EBPβ peptides of the present invention (e.g., mutant mouse, human and rat peptides) will find use in the therapy and prevention of diseases associated with abnormal fibrosis. Indeed, the modified C/EBPβs (referred to herein as "C/EBPβ") find use in various settings involving the production of fibrosis. In one embodiment, C/EBPβ peptides are administered in combination with other conventional pharmaceutical agents. The combination of therapeutic agents having different mechanisms of action is contemplated to provide synergistic effects allowing for the use of lower effective doses of each agent and lessening side effects. In another embodiment, a vector expressing the polynucleotide encoding C/EBPβ may be administered to a subject to treat or prevent fibrosis. In still another embodiment, a vector expressing antisense of the polynucleotide encoding C/EBPβ may be administered to a subject to stimulate fibrosis (e.g., wound healing).

Expression vectors derived from retroviruses, adenovirus, herpes or vaccinia viruses, or from various bacterial plasmids may be used for delivery of nucleotide sequences to the targeted organ, tissue or cell population. In addition to the methods described elsewhere herein, methods which are well known to those skilled in the art can be used to construct recombinant vectors which will express C/EBPβ.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection and by liposome injections may be achieved using methods which are well known in the art.

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical composition, in conjunction with a pharmaceutically acceptable carrier, for any of the therapeutic effects discussed above. Such pharmaceutical compositions may consist of C/EBPβ, antibodies to C/EBPβ, mimetics, agonists, antagonists, or inhibitors of C/EBPβ. The compositions may be administered alone or in combination with at least one other agent, such as stabilizing compound, which may be administered in any sterile, biocompatible pharmaceutical carrier, including, but not limited to, saline, buffered saline, dextrose, and water. The compositions may be administered to a patient alone, or in combination with other agents, drugs or hormones. As indicated herein, the pharmaceutical compositions utilized in this invention may be administered by any number of suitable routes.

In addition to the active ingredients, these pharmaceutical compositions may contain suitable pharmaceutically-acceptable carriers comprising excipients and auxiliaries which facilitate processing of the active compounds into preparations which can be used pharmaceutically, as known in the art.

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient. Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethyl-cellulose, or sodium carboxymethylcellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Pharmaceutical formulations suitable for parenteral administration may be formulated in aqueous solutions, preferably in physiologically compatible buffers such as Hanks's solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are known to those in the art.

The pharmaceutical compositions of the present invention may be manufactured in a manner that is known in the art (e.g., by means of conventional mixing, dissolving, granulating, dragee-making, levigating, emulsifying, encapsulating, entrapping, or lyophilizing processes).

The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation may be a lyophilized powder which may contain any or all of the following: 1-50 mM histidine, 0.1%-2% sucrose, and 2-7% mannitol, at a pH range of 4.5 to 5.5, that is combined with buffer prior to use.

After pharmaceutical compositions have been prepared, they can be placed in an appropriate container and labeled for treatment of an indicated condition. For administration of C/EBPβ such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays and/or in animal models. The animal model may also be used to determine the appropriate concentration range and route of administration. Such information is then be used to determine useful doses and routes for administration in humans. A therapeutically effective dose refers to that amount of active ingredient which ameliorates the symptoms or condition. Therapeutic efficacy and toxicity may be determined by standard pharmaceutical procedures in cell cultures or experimental animals (e.g., the ED50—the dose therapeutically effective in 50% of the population) and LD50 (the dose lethal to 50% of the population). The dose ratio between therapeutic and toxic effects is the therapeutic index, and it can be expressed as the ratio, LD50/ED50.

Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active moiety or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

Normal dosage amounts may vary depending upon the subject and the route of administration. Guidance as to particular dosages and methods of delivery is provided in the literature and generally available to those skilled in the art. Those skilled in the art will employ different formulations for nucleotides than for proteins or their inhibitors. Similarly, delivery of polynucleotides or polypeptides will be specific to particular cells, conditions, locations, etc.

Diagnosis

In another embodiment, antibodies which specifically bind C/EBPβ find use in the diagnosis of conditions or diseases characterized by increased or decreased fibrosis, or in assays to monitor patients being treated with C/EBPβ (e.g., the modified C/EBPβs of the present invention).

For the production of antibodies, various hosts including goats, rabbits, rats, mice, humans, and others, may be immunized by injection with C/EBPβ or any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, BCG (bacilli Calmette-Guerin) and *Corynebacterium parvum* are especially preferable.

Monoclonal antibodies to C/EBPβ may be prepared using any technique which provides for the production of antibody molecules by continuous cell lines in culture, including but not limited to the hybridoma technique, the human B-cell hybridoma technique, and the EBV-hybridoma technique.

In addition, techniques developed for the production of "chimeric antibodies", the splicing of mouse antibody genes to human antibody genes to obtain a molecule with appropriate antigen specificity and biological activity can be used, as known in the art. Alternatively, techniques described for the production of single chain antibodies may be adapted, using methods known in the art, to produce C/EBPβ single chain antibodies. Antibodies with related specificity, but of distinct idiotypic composition, may be generated by chain shuffling from random combinatorial immunoglobin libraries, as known in the art. Antibodies may also be produced by inducing in vivo production in the lymphocyte population or by screening recombinant immunoglobulin libraries or panels of highly specific binding reagents as known in the art.

Antibody fragments which contain specific binding sites for C/EBPβ may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity, as known in the art.

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between C/EBPβ and its specific antibody.

Diagnostic assays for C/EBPβ include methods which utilize the antibody and a label to detect C/EBPβ in cells or tissues. The antibodies may be used with or without modification, and may be labeled by joining them, either covalently or non-covalently, with a reporter molecule. A wide variety of reporter molecules which are known in the art may be used, several of which are described above. A variety of protocols including ELISA, RIA, IFA, and FACS for measuring C/EBPβ are known in the art and provide one basis for monitoring levels of C/EBPβ expression.

In another embodiment of the invention, the polynucleotides encoding C/EBPβ are used for diagnostic purposes. The polynucleotides which may be used include oligonucleotide sequences, antisense RNA and DNA molecules, and PNAs. The polynucleotides may be used to detect and quantitate gene expression in biopsied tissues in which expression of C/EBPβ may be correlated with disease and/or disease amelioration. The diagnostic assay may be used to distinguish between absence, presence, and excess expression of C/EBPβ, and to monitor regulation of C/EBPβ levels during therapeutic intervention.

In one aspect, hybridization with PCR probes which are capable of detecting polynucleotide sequences, including genomic sequences, encoding C/EBPβ or closely related molecules, may be used to identify nucleic acid sequences which encode C/EBPβ. The specificity of the probe, whether it is made from a highly specific region and the stringency of the hybridization or amplification (maximal, high, intermediate, or low) will determine whether the probe identifies only naturally occurring sequences encoding C/EBPβ alleles, or related sequences (e.g., the modified C/EBPβs of the present invention).

EXPERIMENTAL

The following examples serve to illustrate certain preferred embodiments and aspects of the present invention and are not to be construed as limiting the scope thereof.

In the experimental disclosure which follows, the following abbreviations apply: eq (equivalents); M (Molar); mM (millimolar); μM (micromolar); N (Normal); mol (moles); mmol (millimoles); μmol (micromoles); nmol (nanomoles); g (grams); mg (milligrams); μg (micrograms); Kg (kilograms); L (liters); mL (milliliters); μL (microliters); cm (centimeters); mm (millimeters); μm (micrometers); nm (nanometers); h and hr (hours); min. (minutes); s and sec. (seconds); ° C. (degrees Centigrade); v/v (volume/volume); w/v (weight/volume), μCi (microcuries); FDA (United States Food and Drug Administration); DME (Dulbecco's Modified Eagles Medium); LDL (low-density lipoprotein); DMF (N,N-dimethylformamide); α-SMA (α-smooth muscle actin); MDA (malondialdehyde); 4-HNE (4-hydroxynonenal); PBS (phosphate buffered saline); FBS (fetal bovine serum); $K_2CO_3$ (potassium carbonate); $NaHCO_3$ (sodium bicarbonate); $MgCl_2$ (magnesium chloride); NaOH (sodium hydroxide); $FeSO_4$ (ferrous sulfate); $MgSO_4$ (magnesium sulfate); SD or S.D. (standard deviation); SEM (standard error of the mean); Accurate Chemical & Scientific Corp. (Westbury, N.Y.); Becton Dickinson (Hunt Valley, Md.); Amersham (Arlington Heights, Ill.); Charles River Breeding Labs (Wilmington, Mass.); Clonetics (Clonetics Corp., San Diego, Calif.); Pharmingen (San Diego, Calif.); Collaborative Bio-medical Products (Bedford, Mass.); DuPont (DuPont Co., Wilmington, Del.); Hitachi (Hitachi Scientific Instruments, Mountain View, Calif.); Hoechst (Santa Cruz Biotechnology, Santa Cruz, Calif.); Sigma (Sigma Chemical Company, St. Louis, Mo.); Molecular Probes (Eugene, Oreg.); Upstate Biotechnology (Lake Placid, N.Y.); Vector Laboratories (Burlingame, Calif.); and Alexis (San Diego, Calif.).

Unless otherwise indicated below, the results are expressed as the mean (±SEM) of at least triplicates, unless stated otherwise. Either the Student t of the Fisher's exact test was used to evaluate the differences in the means between groups, with a P value of <0.05 considered to be significant.

Various protein databases were searched during the development of the present invention, including the Atlas Retrieval System protein databases PIR1, PIR2, PIR3 and PATX containing more than 347,000 proteins, including more than 22,000 TVD and 27,000 EVS sequences. The proapoptotic mutants include mouse—alanine 217, human—alanine 266, and rat—alanine 105.

Example 1

Cell Cultures and Transfections

Adult male Sprague-Dawley rats and adult male $C/EBP\beta^{+/+}$ and $C/EBP\beta^{-/-}$ (Screpanti et al., supra; and Buck et al., [1999], supra), $C/EBP\beta$-$Ala^{217}$ and $C/EBP\beta$-$Asp^{105}$ transgenic mice were used for the isolation of primary hepatic stellate cells (Houglum et al., supra). Primary hepatic stellate cells were isolated by collagenase/pronase perfusion and purified by a single step density Nycodenz gradient (Accurate Chemical & Scientific) as known in the art (See, Lee et al., [1995], supra). Cells were plated on type I collagen matrix (Becton Dickinson) or EHS matrix (Matrigel, Collaborative Biomedical Products). Cells were cultured with 10% fetal calf serum/10% fetal bovine serum and transfected with lipofectamine (GIBCO) for DNA vectors or with the Chariot reagent (Active Motif) for peptides (10 μM) as known in the art (See, Houglum et al., supra; and Morris et al., J. Biol. Chem., 274:24942-24946 [1999]).

Transgenic mice expressing rat $C/EBP\beta$-$Asp^{105}$ mutant or mouse $C/EBP\beta$-$Ala^{217}$ mutant were generated using methods known in the art (See, Houglum et al., supra; and Lee et al., [1995], supra) and back crossed to FVB mice. The presence of the neo gene was used to identify the transgenic mice by Southern blots. Endogenously expressed transfected proteins were visualized using antibodies specific for HA or $C/EBP\beta$ (Santa Cruz Biotechnology).

Expression of $C/EBP\beta$ 1-253, with a deletion of the dimerization domain (Descombes et al., supra; Akira et al., supra) (FIG. 4, Panel A) and containing $Thr^{217}$ or $Glu^{217}$, but not $Ala^{217}$, was compatible with cell growth and survival. $C/EBP\beta$ 1-215 lacking the DNA binding and dimerization domains and the $KT^{217}VD$ phosphoacceptor (See, FIG. 4, Panel A) had no effect on cell survival. In contrast, $C/EBP\beta$ 216-253-$Ala^{217}$, but not $T^{217}$ or $Glu^{217}$, lacking the activation and dimerization domains (See, FIG. 4, Panel A), stimulated apoptosis in control cells and following expression of wild type RSK (See, FIG. 4, Panel B). In addition, $C/EBP\beta$ 216-253-$Glu^{217}$ was sufficient to rescue cells from apoptosis induced by a catalytically inactive mutant RSK expression vector (RSK N'C'), containing point mutations in both ATP-binding domains (Nakajima et al., supra; and Buck et al., [1999], supra) (See, FIG. 4, Panel B). Using confocal microscopy, and in agreement with previous reports (Mao et al., supra; and Ritter et al., supra), procaspases 1 and 8 were detected in the nucleus and cytoplasm of activated stellate cells, which colocalized with $C/EBP\beta$ (See, FIG. 4, Panel C).

Immunoprecipitation of the $C/EBP\beta$-HA and $C/EBP\beta$ 216-253-HA, with antibodies against HA, from activated stellate cells, showed that both the phosphorylatable $Thr^{217}$ and the phosphorylation mimic $Glu^{217}$, co-immunoprecipitated with procaspases 1 and 8 more efficiently than the nonphosphorylatable $Ala^{217}$ (See, FIG. 4, Panel D). Therefore, the $C/EBP\beta$ activation and dimerization domains (Descombes et al., supra; and Akira et al., supra) are not required for stellate cell survival or association with procaspases 1 and 8.

Example 2

Fluorescence Microscopy Methods

Fluorescent labels were observed using a triple-channel fluorescence microscope. The fluorochromes utilized were FITC and Texas red (Molecular Probes). The number of annexin V (+) cells was determined by in vivo microscopy as known in the art (See, Rudel and Bokoch, supra) among all cells or those expressing the GFP indicator protein either co-transfected with $C/EBP\beta$ proteins, or alone. These values are reported herein as a percentage of annexin V (+) for cells expressing the transfected DNA. At least 1000 cells were analyzed per experimental point, including at least 100 cells expressing the transfected DNA (Buck and Chojkier. EMBO J., 15:1753-1765 [1996]; Buck et al., [1994], supra; and Buck et al., [1999], supra). The ApoAlert mitochondrial-sensor assay (Clontech) used in some experiments utilizes a cationic dye that fluoresces red when aggregated within the mitochondria in healthy cells and green when it remains in monomeric form in the cytosol of apoptotic cells due to altered mitochondrial membrane potential (Green and Reed, supra). Nuclear morphology was analyzed by staining cells with Hoechst 33342 (Molecular Probes). Confocal microscopy was performed in stellate cells using antibodies specific for $C/EBP\beta$ and procaspase 8 (Santa Cruz Biotechnology).

For example, in one set of experiments, investigations were conducted in order to determine whether phosphorylation of $Ser^{105}$ confers to $rC/EBP\beta$ the ability to rescue cells from apoptosis. Activated mouse hepatic stellate cells cultured on a collagen type I matrix were induced to develop apoptosis either by expressing the dominant negative RSK mutant (Nakajima et al., supra) or by treating them with lactacystin (a proteasome inhibitor). Transfection of the phosphorylation mimic $rC/EBP\beta$ $Asp^{105}$ (Trautwein et al., supra), together with the transfection indicator CMV-GFP, rescued hepatic stellate cells from apoptosis as determined by the incorporation of annexin-V-PE using in vivo fluorescence microscopy (See, FIG. 5, Panel B). $rC/EBP\beta$-$Ala^{105}$, like $C/EBP\beta$-$Ala^{217}$, induced apoptosis of activated primary mouse hepatic stellate cells, since neither mutant has a RSK phosphoacceptor domain (Buck et al., [1999], supra). These results suggest that $rC/EBP\beta$-$PSer^{105}$ (or $rC/EBP\beta$-$Asp^{105}$), at least under the experimental conditions described, is able to block the apoptotic pathway as effectively as C/EBPβ-PThr$^{217}$ (See, FIG. 1).

Example 3

Animal Procedures and Testing

As described herein, investigations were conducted to determine whether hepatic stellate cell activation is stimulated by CCl$_4$, a hepatotoxin that induces hepatic oxidative stress and liver fibrogenesis (Houglum et al., supra; and Chojkier, supra). Transgenic mice expressing rat C/EBPβ-Asp$^{105}$ or mouse C/EBPβ-Ala$^{217}$ were generated as described herein, using methods known in the art (See, Houglum et al. [1995]. supra; and Lee et al. [1995], supra) and back-crossed to FVB mice. The presence of the neo gene was used to identify these transgenic mice by Southern blotting.

C/EBPβ$^{+/+}$, C/EBPβ$^{-/-}$ and C/EBPβ-Ala$^{217}$ or C/EBPβ-Asp$^{105}$ transgenic mice (25 g) each received a single intraperitoneal injection of CCl$_4$, in mineral oil (1:1, vol/vol) (50 µl) or mineral oil only (25 µl) (Buck et al., [1999], supra). Twelve hours later, animals were sacrificed and immunofluorescence analyzed by confocal microscopy (Buck et al., [1994], supra). Stellate cells were identified using antibodies specific for glial fibrillary acidic protein and vimentin (Santa Cruz Biotechnology). Active caspase 3 was observed using specific antibodies (Pharmingen).

Hepatic stellate cells, identified by their glial fibrillary acidic protein and vimentin staining (Ankoma-Sey and Friedman, supra), were induced to proliferate in the liver of C/EBPβ$^{+/+}$ mice following treatment with a single dose of CCl$_4$. In contrast, CCl$_4$ induced stellate cell apoptosis in the livers of C/EBPβ$^{-/-}$ and C/EBPβ-Ala$^{217}$ transgenic mice (See, FIG. 3), as determined by the presence of an active effector caspase 3. Because activated p90RSK is able to causing the in vitro phosphorylation of C/EBPβ on Thr$^{217}$ (Buck et al., [1999], supra), it was of interest to determine whether RSK was associated with C/EBPβ in these animals, as described in Example 4.

Example 4

Immunoprecipitation and Immunoblotting

C/EBPβ, procaspases 1 and 8 and RSK were detected by immunoblotting in cell and liver lysates (Buck et al., [1994], supra) following a chemiluminescence protocol (DuPont) using purified IgG antibodies, specific for C/EBPβ and RSK (Santa Cruz Biotechnology) and for procaspases 1 and 8 (Pharmingen). The results were confirmed using rabbit anti-RSK-5 serum (kindly provided by J. Blenis) and anti-RSK R23820 (Transduction Laboratories).

Because activated p90RSK is able to cause the in vitro phosphorylation of C/EBPβ on Thr$^{217}$ (Buck et al., [1999], supra), it was of interest to determine whether RSK was associated with C/EBPβ in these animals. In these experiments, C/EBPβ was immunoprecipitated with specific antibodies from primary hepatic stellate cells freshly isolated from C/EBPβ$^{+/+}$ and C/EBPβ-Ala$^{217}$ mice treated with CCl$_4$. The results indicated that there was an increased RSK association with C/EBPβ in stellate cells isolated from C/EBPβ$^{+/+}$, but not C/EBPβ-Ala$^{217}$ mice treated with CCl$_4$, as indicated in FIG. 3. RSK was identified using specific antibodies against pp90RSK (Santa Cruz Biotechnology), which do not cross-react with p70 S6 kinase. These results were confirmed using two other specific antibodies, anti-RSK-5 (kindly provided by J. Blenis) and anti-RSK (Transduction Laboratories). When RSK protein was immunoprecipitated with specific antibodies, C/EBPβ was found to co-immunoprecipitate, and the level of coprecipitated C/EBPβ was consistently increased in C/EBPβ$^{+/+}$ mice treated with CCl$_4$. Control preimmune serum, anti-β-galactosidase, or purified IgG yielded immunoprecipitates containing undetectable levels of either RSK of C/EBPβ, confirming the specificity of the co-immunoprecipitation procedure. These findings strongly suggest that phosphorylation of C/EBPβ on Thr$^{217}$ by RSK is indispensable for hepatic stellate cell survival.

Example 5

Phosphorylation of C/EBPβ

Day-4 primary mouse or rat hepatic stellate cells cultured on an EHS (Matrigel; Becton-Dickinson) (quiescent cells) of collagen type I (Collaborative Research) (activated cells) were labeled with 30 mCi $^{32}$P-orthophosphate for 12 hours (cultured for the last 30 min with 20% fetal calf serum) and two-dimensional tryptic maps were performed as known in the art (See, Trautwein et al., supra; Buck et al., [1999], supra).

For RSK phosphorylation reactions in vitro, 3 µg of immunopurified C/EBPβ, C/EBPβ-Ala$^{217}$, rC/EBPβ and rC/EBPβ-Ala$^{105}$ were assayed as known in the art (See, Buck et al. [1999], supra). The identity of the phosphopeptides containing PThr$^{217}$ or PSer$^{105}$ was suggested by the migration of the putative peptide and confirmed with specific antibodies against the phosphorylated epitopes of human (KSKAKK-PhosphoT$^{266}$VDKHSD [SEQ ID NO:16]; homologous to mouse PThr$^{217}$) and rat (KPSKKP-PhosphoS$^{105}$DYGYVS [SEQ ID NO:17]) C/EBPβ.

In experiments to test whether collagen type I matrix induces C/EBPβ phosphorylation, primary mouse hepatic stellate cells were labeled for 12 hr with $^{32}$P-orthophosphate and cultured either on EHS (Matrigel) (quiescent cells) or collagen type I (activated cells). Phosphopeptide mapping of immunoprecipitated C/EBPβ showed that collagen type I matrix induced a site-specific phosphorylation of endogenous C/EBPβ on Thr$^{217}$, a p90RSK phosphoacceptor domain (Buck et al., [1999], supra), and on another, yet unidentified, phosphoacceptor site, as indicated by the results in FIG. 1. C/EBPβ phosphorylation was negligible in quiescent mouse stellate cells cultured on an EHS matrix (See, FIG. 1).

Although the C/EBPβ-Thr$^{217}$ phosphoacceptor is highly conserved through evolution including human C/EBPβ, (Cao et al., supra; Akira et al., supra; and Yamaoka et al., supra), rat (r)C/EBPβ has evolved with a double mutation, lacking the Thr phosphoacceptor but having a compensatory Ser$^{105}$ phosphoacceptor (Descombes et al., supra; and Poli et al., supra). C/EBPβ-PThr$^{217}$ or rC/EBPβ-PSer$^{105}$ are critical for extracellular factor-induced cell proliferation (Buck et al., [1999], supra). To test whether collagen type I matrix induces rC/EBPβ phosphorylation, primary rat hepatic stellate cells were labeled for 12 hr with $^{32}$P-orthophosphate and cultured either on EHS (Matrigel) (quiescent cells) or collagen type I (activated cells). Phosphopeptide mapping of immunoprecipitated C/EBPβ showed that collagen type I matrix induced phosphorylation of endogenous rC/EBPβ on Ser$^{105}$, a p90RSK phosphoacceptor domain (Buck et al., [1999], supra), and on other, yet unidentified phosphoacceptor sites (See, FIG. 6, Panel A). rC/EBPβ phosphorylation was negligible in quiescent rat stellate cells cultured on an EHS matrix (See, FIG. 6, Panel A).

Next, the functional relevance of C/EBPβ and its phosphorylation on Thr$^{217}$ was ascertained. Activated primary mouse hepatic stellate cells were transfected with either wild-type (sense) or antisense C/EBPβ expressing vectors. Stellate cells expressing C/EBPβ antisense, but not sense, RNA (Buck et al., [1994], supra) did not proliferate, as detected by the expression of proliferating cell nuclear antigen (Bravo et al., supra; Buck et al., [1994], supra; and Buck et al., [1999], supra), but displayed increased annexin-V binding to phosphatidylserine in plasma membranes, an early indicator of apoptosis (Rudel and Bokoch, supra) (See, FIG. 1, Panel C). To determine whether phosphorylation of mouse C/EBPβ on Thr$^{217}$ is critical for collagen type 1-induced proliferation of mouse hepatic stellate cells, cells were transfected with a MSV expression vector for the nonphosphorylatable C/EBPβ-Ala$^{217}$ mutant. Transfected cells were identified by the expression of the co-transfected CMV-GFP (green fluorescent protein) using triple-channel fluorescence microscopy. Cells expressing the C/EBPβ-Ala$^{217}$ mutant (Buck et al., [1999], supra) did not proliferate and became apoptotic as determined by live microscopy (FIG. 1, Panel C) and cell sorting for the transfection indicator GFP and annexin-V. Conversely, induction of apoptosis in hepatic stellate cells by blocking activation of the antiapoptotic NFκB (Beg and Baltimore, supra; and Wang et al., supra) or RSK (Buck et al., [1999], supra; Bonni et al., supra; Bhatt and Ferrell, supra; Gross et al., supra; and Sassone-Corsi et al., supra) was rescued by the phosphorylation mimic C/EBPβ-Glu$^{217}$ mutant (Buck et al., [1999], supra), as indicated in FIG. 1, Panel D.

MEK kinase 1 (MEKK1) activates NFκB through phosphorylation of IκB kinases α and β leading to phosphorylation of IκB (Lee et al., [1997], supra; Nakano et al., supra), which undergoes rapid proteolysis via the ubiquitin-proteasome pathway (Chen et al., [1995a], supra). Therefore, activated primary stellate cells were transfected with expression vectors for the dominant negative mutants for MEKK1, IκBα and RSK, or treated cells with lactacystin (a proteasome inhibitor) to induce apoptosis. In each case, stellate cell apoptosis was rescued by expressing C/EBPβ-Glu$^{217}$ (See, FIG. 1, Panel D), suggesting that in the absence of active NFκB or RSK, phosphorylation of C/EBPβ on Thr$^{217}$ is sufficient for hepatic stellate cell survival.

To ascertain the functional relevance of mouse C/EBPβ, and its phosphorylation on Thr$^{217}$, the survival of primary hepatic stellate cells isolated from mice with a targeted deletion of C/EBPβ (Screpanti et al., supra) was also investigated. C/EBPβ$^{-/-}$, but not C/EBPβ$^{+/+}$, stellate cells were refractory to growth stimulation by collagen type I and became apoptotic as determined by annexin-V binding using live microscopy (FIG. 2, Panels A and C). To study the role of C/EBPβ-PThr$^{217}$ on stellate cell survival, mice expressing a nonphosphorylatable dominant negative C/EBPβ-Ala$^{217}$ mutant transgene were developed. Although C/EBPβ-Ala$^{217}$ transgenic mice were developmentally normal, hepatic stellate cells isolated from these animals consistently failed to survive when activated by collagen type I (See, FIG. 2, Panels A and C). Apoptosis of stellate cells isolated from C/EBPβ$^{-/-}$ and C/EBPβ-Ala$^{217}$ mice was corroborated by an increase in mitochondrial membrane permeability, using a mitochondrial sensor assay (See, FIG. 2, Panel C).

Example 6

Induction of Mesenchymal Cell Apoptosis by C/EBPβ-Ala$^{217}$

In these experiments, C/EBPβ-Ala$^{217}$ was tested in two mesenchymal cell lines for its ability to induce apoptosis. Human mesenchymal cell lines 1321-N1 (glial cells; obtained from Dr. Joan Brown, at the University of California, San Diego), RD (skeletal muscle cells; ATCC Accession No. CCL-136), and human fibroblasts (98VA3N cells, obtained from Dr. Jerry VanderBerg, at the Veterans Administration Medical Center, San Diego, Calif.) were cultured in minimal essential medium supplemented with fetal bovine serum as known in the art (See e.g., Buck et al., EMBO J., 13:151-160 [1994]). As additional cell types find use in the present invention, it is not intended that the present invention be limited to these specific cell lines. Indeed, similar results have been obtained with other cell types (e.g., CCF-STTG1 cells [ATCC Accession No. CRL-1718]) (data not shown).

Cells were co-transfected with vectors expressing the indicator protein GFP and C/EBPβ-Ala$^{217}$ as known in the art (See, Buck et al., Mol. Cell., 4:1087-1092 [1999]). Control cells were only transfected with GFP. Four hours after transfection, cells were assayed for annexin-V binding to exposed phosphatidylserine in plasma membranes, an early indicator of apoptosis, using live microscopy as known in the art, using a commercially available apoptosis kit (R & D Systems) according to the manufacturer's instructions (See also, Rudel and Bokoch, Science 276:1571-1574 [1997]).

Expression of the non-phosphorylatable C/EBPβ-Ala$^{217}$ mutant induced apoptosis of these mesenchymal cell lines, as indicated in Table 1, below.

TABLE 1

Induction of Mesenchymal Cell Apoptosis by C/EBPβ-Ala$^{217}$

| Cell Line | Apoptosis (%) | |
|---|---|---|
|  | Control | C/ERPβ-Ala$^{217}$ |
| RD | 9 | 46* |
| 1321 NI | 4 | 56* |
| 98VA3N | 6 | 80* |

*P < 0.01

Thus, these data indicate that C/EBPβ-Ala$^{217}$ will find use as a therapeutic in the treatment of fibrosis in various tissues and cell types.

Example 7

Procaspase Activation and Caspase Activity

In these experiments, purified recombinant and synthetic C/EBPβ peptides were assayed for their ability to inhibit the activation of purified recombinant procaspases 1 and 8 (Alexis Biochemicals).

Purified recombinant C/EBPβ peptides, expressed as known in the art (See, Descombes et al., supra; and Buck et al. [1994], supra), and purified synthetic N-acetyl, C-aldehyde tetrapeptides (200 μM) (American Peptide Company) were assayed for their ability to inhibit the activity of purified human recombinant caspases 1 (catalogue #201-056) and 8 (catalogue #201-041-C005) (Alexis Biochemicals). The sequence of caspase 8 includes Ser217 through Asp479 cloned into an expression vector containing a 21 amino acid linker at the N-terminus. Thus, the prodomain (first 220 amino acids) is essentially missing. The fragment is cleaved at Asp385 and the active caspases are essentially identical to those identified in apoptotic cells (Stennicke and Salvesen, Meth. Enzymol., 322:91-100 [1997]). Caspase activity was determined by the release of the p-nitroanaline colorimetric (Alexis Biochemicals) substrate for caspase I (catalogue #260-026) or 8 (catalogue #260-045) within the linear part of the kinetic assay (Thornberry et al. [1997], supra; Stennicke and Salvesen, supra). Caspase 1 and 8 activity in cells was performed with colorimetric kits (catalogues #850-211-K and 850-221-K) as described by the manufacturer (Alexis) (See also, Thornberry et al. [1997], supra). The caspase 8 inhibitor IETD was from Calbiochem (Catalogue #218773).

Given that the $Thr^{217}$ phosphoacceptor in C/EBPβ contains a $KT^{217}VD$ sequence to bovine and human C/EBPβ (Buck et al., [1999], supra), that upon phosphorylation by RSK can be functionally mimicked by the C/EBPβ-$Glu^{217}$ sequence $KE^{217}VD$ (Buck et al., [1999], supra), and that the latter is similar to a XEXD box, found in inhibitors and substrates of caspases (Thornberry et al., supra; and Blanchard et al., supra), experiments were conducted to investigate whether C/EBPβ-$PThr^{217}$ associates with procaspases. C/EBPβ was immunoprecipitated using specific antibodies, from freshly isolated hepatic stellate cells from C/EBPβ$^{+/+}$ and C/EBPβ-$Ala^{217}$ transgenic mice. With the use of specific antibodies, the initiator procaspases 1 and 8 were identified (See, FIG. 3, Panel D) but not the effector procaspases 3, 7 or 9 (Thornberry and Lazebnik, supra; Ashkenazi and Dixit, supra; and Earnshaw et al., supra), in C/EBPβ but not in control IgG, immunoprecipitates of activated C/EBPβ$^{+/+}$ stellate cells, following treatment with $CCl_4$.

The association of C/EBPβ with procaspases 1 and 8 remained baseline in cells from C/EBPβ-$Ala^{217}$ mice treated with $CCl_4$ (FIG. 3), as well as in cells from C/EBPβ$^{+/+}$ mice treated with control mineral oil. In addition, the activities of the initiator caspases 1 and 8 (See, FIG. 3), as well as that of the effector caspase 3 (See, FIG. 3), were increased in stellate cells from C/EBPβ$^{-/-}$ or C/EBPβ-$Ala^{217}$, but not from C/EBPβ$^{+/+}$ mice following treatment of these animals with $CCl_4$. These results indicate that phosphorylation of C/EBPβ on $Thr^{217}$ or the phosphorylation mimic C/EBPβ-$Glu^{217}$ mutant are required for C/EBPβ to associate with procaspases 1 and 8, and suggest that they may prevent processing and activation of procaspases 1 and 8, since neither KPhospho-$T^{217}VD$ nor $KE^{217}VD$ are the preferred substrates for caspases 1 or 8 (Wilson et al., supra; Margolin et al., supra; and Earnshaw et al., supra).

To delineate the role of C/EBPβ on the activation of procaspases 1 and 8, the self-activation of recombinant procaspases 1 and 8 was induced in vitro (Wilson et al., supra; Margolin et al., supra; and Earnshaw et al., supra), and the effect of purified recombinant C/EBPβ peptides, produced as described previously (Descombes et al., supra; and Buck et al., [1994], supra) on this process was determined. Consistent with the in vivo results described above, C/EBPβ-HA-$Glu^{217}$ and C/EBPβ 216-253-HA-$Glu^{217}$, but not C/EBPβ-HA-$Ala^{217}$, peptides associated with procaspases 1 and 8 (See, FIG. 5, Panel A). Recombinant C/EBPβ-$Glu^{217}$, and the synthetic peptides Ac-KPhospho-$T^{217}$VD-CHO and Ac-$KE^{217}$VD-CHO inhibited activation of procaspases 1 and 8 (FIG. 5, Panel B). In addition, in activated hepatic stellate cells, the cell permeant peptide Ac-$KA^{217}$VD-CHO induced apoptosis (See, FIG. 5, Panel C).

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the art and/or related fields are intended to be within the scope of the following claims.

We claim:

1. A method for inducing apoptosis comprising administering a composition to hepatic stellate cells, wherein said composition comprises N-acetyl-KAVD-C-aldehyde peptide (Ac-KAVD-CHO) consisting of residues 216-219 of SEQ ID NO:3 or N-acetyl-KKPA-C-aldehyde peptide (Ac-KKPA-CHO) consisting of residues 102-105 of SEQ ID NO:14.

2. The method of claim 1, wherein said composition comprises said N-acetyl-KAVD-C-aldehyde peptide (Ac-KAVD-CHO) consisting of residues 216-219 of SEQ ID NO:3.

3. The method of claim 1, wherein said composition comprises said N-acetyl-KKPA-C-aldehyde peptide (Ac-KKPA-CHO) consisting of residues 102-105 of SEQ ID NO:14.

4. The method of claim 1, wherein said hepatic stellate cells are within a subject, and wherein said administering is under conditions such that the endogenous phosphopeptides of said subject inhibit the activation of at least one caspase of said subject.

5. The method of claim 4, wherein said subject is a mammal.

6. The method of claim 5, wherein said mammal is a human.

7. The method of claim 5, wherein said mammal is suffering from a fibrosis-related disease, wherein said fibrosis-related disease is hepatic disease.

8. The method of claim 7, wherein said administration diminishes fibrosis.

9. The method of claim 7, wherein said administration ameliorates fibrosis.

* * * * *